(12) United States Patent
Kerkis et al.

(10) Patent No.: US 11,207,352 B2
(45) Date of Patent: Dec. 28, 2021

(54) COMPOSITIONS COMPRISING STEM CELLS EXPRESSING MESENCHYMAL AND NEURONAL MARKERS AND USES THEREOF TO TREAT NEUROLOGICAL DISEASE

(71) Applicants: AVITA INTERNATIONAL LTD., Tortola (VG); FUNDAÇÃO BUTANTAN, São Paulo (BR)

(72) Inventors: Irina Kerkis, Sao Paulo (BR); Alexandre Kerkis, Sao Paulo (BR)

(73) Assignees: AVITA INTERNATIONAL LTD., Tortola (VG); FUNDAÇÃO BUTANTAN, Sao Paulo (BR)

(*) Notice: Subject to any disclaimer, the term of this patent is extended or adjusted under 35 U.S.C. 154(b) by 270 days.

(21) Appl. No.: 15/065,259

(22) Filed: Mar. 9, 2016

(65) Prior Publication Data
US 2016/0184366 A1 Jun. 30, 2016

Related U.S. Application Data

(63) Continuation-in-part of application No. 14/214,016, filed on Mar. 14, 2014, now Pat. No. 9,790,468.

(60) Provisional application No. 62/220,792, filed on Sep. 18, 2015, provisional application No. 62/130,593, filed on Mar. 9, 2015, provisional application No. 62/130,585, filed on Mar. 9, 2015, provisional application No. 61/791,594, filed on Mar. 15, 2013, provisional application No. 61/800,245, filed on Mar. 15, 2013.

(51) Int. Cl.
| | |
|---|---|
| *A61K 35/28* | (2015.01) |
| *A61K 9/00* | (2006.01) |
| *C12N 5/0775* | (2010.01) |
| *A61K 35/30* | (2015.01) |
| *C12N 5/0793* | (2010.01) |
| *C12N 5/0797* | (2010.01) |
| *C12N 5/071* | (2010.01) |
| *A61K 35/32* | (2015.01) |
| *C12N 5/079* | (2010.01) |

(52) U.S. Cl.
CPC ............ *A61K 35/28* (2013.01); *A61K 9/0019* (2013.01); *A61K 35/30* (2013.01); *A61K 35/32* (2013.01); *C12N 5/0619* (2013.01); *C12N 5/0621* (2013.01); *C12N 5/0623* (2013.01); *C12N 5/0664* (2013.01); *C12N 5/0678* (2013.01); *C12N 2500/25* (2013.01); *C12N 2500/38* (2013.01); *C12N 2500/84* (2013.01); *C12N 2500/90* (2013.01); *C12N 2501/385* (2013.01); *C12N 2501/39* (2013.01); *C12N 2501/392* (2013.01); *C12N 2501/395* (2013.01); *C12N 2506/1361* (2013.01); *C12N 2533/76* (2013.01)

(58) Field of Classification Search
CPC ..... A61K 35/28; A61K 9/0019; C12N 5/0623
See application file for complete search history.

(56) References Cited

U.S. PATENT DOCUMENTS

| | | |
|---|---|---|
| 2005/0214344 A1 | 9/2005 | Barrows et al. |
| 2009/0324555 A1 | 12/2009 | Thie et al. |
| 2010/0297094 A1 | 11/2010 | Harlan et al. |
| 2011/0002895 A1 | 1/2011 | Ueda et al. |
| 2011/0039388 A1 | 2/2011 | Yamanaka et al. |
| 2011/0059050 A1 | 3/2011 | Cetrulo et al. |
| 2011/0158962 A1 | 6/2011 | Ferro |
| 2012/0009601 A1 | 1/2012 | Moriguchi et al. |
| 2012/0219531 A1 | 8/2012 | Oh et al. |
| 2015/0050248 A1 | 2/2015 | Kerkis et al. |

FOREIGN PATENT DOCUMENTS

| | | |
|---|---|---|
| WO | 2007035843 A2 | 3/2007 |
| WO | 2008080200 A1 | 7/2008 |
| WO | 2012020687 A1 | 2/2012 |
| WO | 2015024089 A1 | 2/2015 |

OTHER PUBLICATIONS

Gioventu et al. "A novel method for banking dental pulp stem cells" (2012), Transfusion and Apheresis Science, vol. 47: 199-206 (Year: 2012).*
Carri et al. "Developmentally coordinated extrinsic signals drive human pluripotent stem cell differentiation toward authentic DARPP-32+ medium-sized spiny neurons", (Oct. 2013), Development and Stem Cells, vol. 140: 301-312. (Year: 2013).*
Spath et al. "Explant-derived human dental pulp stem cells enhance differentiation and proliferation potentials", 2010, J. Cell. Mol. Med., No. 68: 1635-1644 (Year: 2010).*
Sakai et al., "Human dental pulp-derived stem cells promote locomotor recovery after complete transection of the rat spinal cord by multiple neuro-regenerative mechanisms", The Journal of Clinical Investigation, 122(1):80-90 (Jan. 2012).
Ryan, Jennifer et al., "Mesenchymal stem cells avoid allogeneic rejection", Journal of Inflammation, 2(1):1-11 (2005).
Gomes et al., "Corneal Reconstruction with Tissue-Engineered Cell Sheets Composed of Human Immature Dental Pulp Stem Cells", Investigative Ophthalmology & Visual Science, 51(3):1408-1414 (Mar. 2010).
Kerkis et al., "Stem Cells in Dental Pulp of Deciduous Teeth", Tissue Engineering: Part B, 18(2):129-138 (2012).

(Continued)

*Primary Examiner* — Teresa E Knight
(74) *Attorney, Agent, or Firm* — Rodney J. Fuller; Booth Udall Fuller, PLC

(57) ABSTRACT

The invention provides pharmaceutical compositions comprising human immature dental pulp stem cells (hIDPSCs) wherein the hIDPSCs express CD44 and CD13. The invention also provides methods of treating a neurological disease or condition comprising systemically administering to a subject a pharmaceutical composition comprising hIDPSCs wherein the hIDPSCs express CD44 and CD13. For example, for treating neurological diseases or conditions including supporting the neuro-protective mechanism in subjects diagnosed with early HD or repairing lost DA neurons in subjects diagnosed with PD.

18 Claims, 37 Drawing Sheets

(56) References Cited

OTHER PUBLICATIONS

Martins de Almeida et al., "Human Dental Pulp Cells: A New Source of Cell Therapy in a Mouse Model of Compressive Spinal Cord Injury", Journal of Neurotrauma, 28:1939-1949 (Sep. 2011).

Monteiro et al., "Human immature dental pulp stem cells share key characteristic features with limbal stem cells", Cell Prolif., 42:587-594 (2009).

Kerkis et al., "Isolation and Characterization of a Population of Immature Dental Pulp Stem Cells Expressing OCT-4 and Other Embryonic Stem Cell Markers", Cells Tissues Organs, 184:105-116 (2006).

Hayashi et al., "Long-Term Culture of Mouse Embryonic Stem Cell-Derived Adherent Neurospheres and Functional Neurons", Tissue Engineering: Part C, 16(6):1493-1502 (Jun. 16, 2010).

Lizier et al., "Scaling-Up of Dental Pulp Stem Cells Isolated from Multiple Niches", PLoS One, 7(6), e39885, pp. 1-12 (Jun. 2012).

Huschtscha et al., "Enhanced isolation of fibroblasts from human skin explants", BioTechniques, 53(4):239-244 (Oct. 1, 2012).

Blurton-Jones et al., "Neural stem cells improve cognition via BDNF in a transgenic model of Alzheimer disease", PNAS, 106(32):13594-13599 (Aug. 11, 2009).

Karaoz et al., "Human dental pulp stem cells demonstrate better neural and epithelial stem cell properties than bone marrow-derived mesenchymal stem cells", Histochemistry and Cell Biology, 136(4):455-473 (Oct. 31, 2011).

Gronthos et al., "Stem Cell Properties of Human Dental Pulp Stem Cells", Journal of Dental Research, Internationa Association for Dental Research, US, 81(8):531-535 (Aug. 1, 2002).

Janebodin et al., "Isolation and Characterization of Neural Crest-Derived Stem Cells from Dental Pulp of Neonatal Mice", PLOS One, 6(11):e27526 (Nov. 8, 2011).

\* cited by examiner

FIG. 15
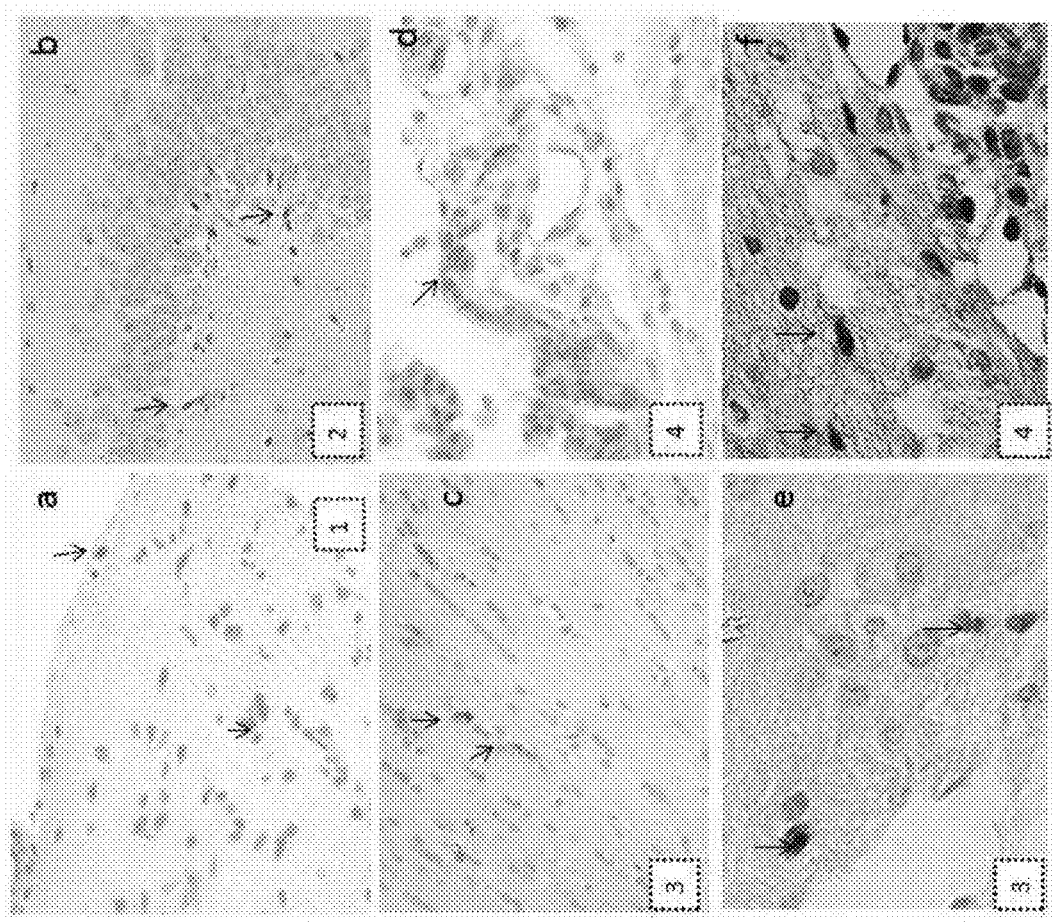
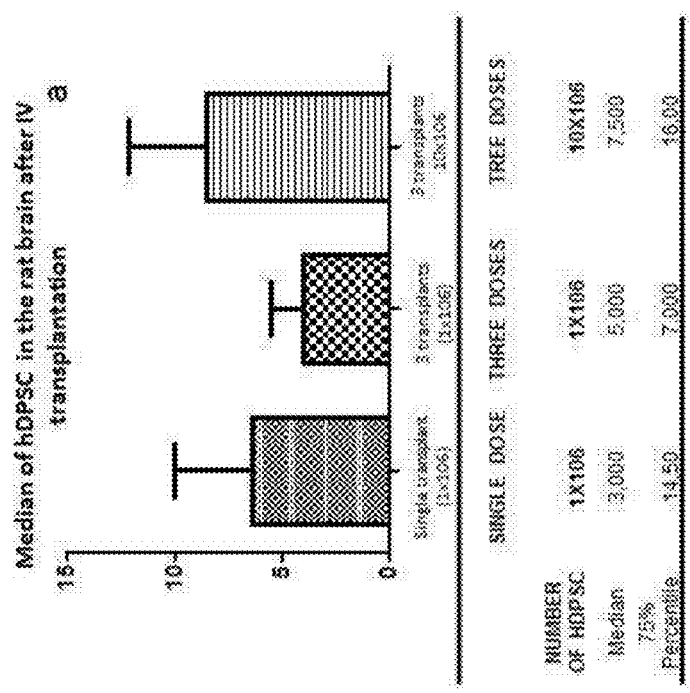
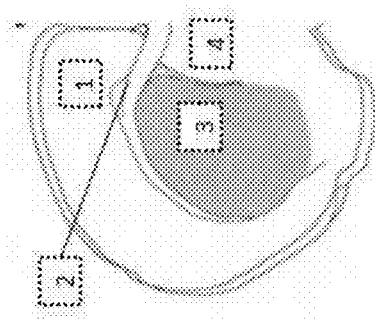

FIG. 28

| Pharmacological Efficacy or Disease Model Studies | Animal Models | Objectives | Results/Conclusions |
|---|---|---|---|
| Cells alone (CELLAVITA™) via IV Route | | | |
| Huntington's disease | 3-nitropropionic acid (3-NP) rat model of HD | Determine the safe and effective hIDPSC dose in an animal model. Evaluate the engraftment capacity and homing of hIDPSCs in the striatum and cortex after intravenous administration. Test the neuroprotective and neuroreparative effects of hIDPSCs in a 3-NP animal model of HD. Examine the motor ability of animals using the open field and Rotarod tests following hIDPSC administration. | hIDPSCs crossed the blood-brain barrier and were found in the striatum, cortex and subventricular zone (SVZ). Extensive growth of intrinsic neuronal cells was observed after hIDPSC-transplantation in comparison with animal which received placebo. In addition, hIDPSC showed neuroprotective and neuroreparative effects through the upregulation of expression of endogenous BDNF, DARPP32, and dopamine receptor D2. hIDPSC-treated animals ($1\times10^5$ and $1\times10^6$ per animal, which corresponds to $0.35\times10^4$ and to $3.5\times10^4$ per kg, respectively) showed significant ambulatory improvement but no statistically significant difference was observed in the Rotarod test due to animal model limitations described above. hIDPSC administration was safe and did not present signs of indisposition or queasiness. Animals, which received hIDPSCs showed no weight loss, suggesting cell's protective |

FIG. 28 (continued)

| Pharmacological Efficacy or Disease Model Studies | Animal Models | Objectives | Results/Conclusions |
|---|---|---|---|
| Duchenne muscular dystrophy (DMD) | Golden retriever muscular dystrophy (GRMD) dogs | Investigate the better dose regimen (IM or IV) for the treatment of Golden retriever muscular dystrophy (GRMD), the disease model for DMD. Safe of multiple (up to nine) monthly hDPSCs transplantations, starting from infancy. | Systemic delivery of hDPSCs is more effective than local injections, because migration ability is restricted to local muscle fibers at the site of administration. Multiple hDPSC transplantations showed to be safe, considering that animal, which received the cells monthly during 9 months in 2006 is still alive and feel well, as it can feel in the context of genetic disease. |
| Acute renal failure (ARF) | Immunocompetent Wistar rats with ARF induced by intramuscular glycerol injections | Investigate the therapeutic potential and homing of hDPSCs after intravenous (IV) or intraperitoneal (IP) injection in an animal model of acute tubular necrosis. Biodistribution of hDPSC after IV injection in several organs including lung, liver muscle, as well as in kidney. | hDPSCs accelerate tubular epithelial cell regeneration. Histological analysis revealed increased blood flow in capillaries of hDPSC-treated animals, which was more pronounced in IV animals. Significant quantity of hDPSCs migrates to the kidneys, and to a lesser extent to the liver, and very low migration was observed to muscle and lungs. After transplantation hDPSCs start vascular endothelial growth factor (VEGF), which was not expressed in undifferentiated cells and showed immunoprotective and anti-apoptotic properties, thus contributing to renal |

FIG. 28 (continued)

| Pharmacological Efficacy or Disease Model Studies | Animal Models | Objectives | Results/Conclusions |
|---|---|---|---|
| Atherosclerosis | New Zealand rabbits fed cholesterol diets | Evaluate the engraftment capacity of hIDPSCs in a rabbit model of atherosclerosis | tubule structure restoration. hIDPSCs played a regenerative role in the endothelial repair of atherosclerotic lesions and can therefore be used as an alternative therapy for the treatment and prevention of atherosclerosis (Ph.D. Dissertation). |
| Cells alone (CELLAVITA™) via Other Routes | | | |
| Ocular surface reconstruction | Total or partial limbal stem cell (LSC) deficiency rabbits | Evaluate ocular surface reconstruction. | Transplantation of a tissue-engineered hIDPSC sheet was successful for reconstruction of corneal epithelium in this animal model of TLSCD. |
| Spinal cord injury | Adult female mice subjected to laminectomy at T9 and compression of the spinal cord | Evaluate the effects of hIDPSC in an animal model of compressive spinal cord injury. | Transplanting hIDPSCs into the epicenter of the spinal cord lesion resulted in better tissue organization and white-matter preservation, increased release of trophic factors, and better functional outcome. Cell therapy using hIDPSCs may be a viable treatment for therapeutic intervention at the subacute and chronic phases of compressive spinal cord injury and CNS disorders. |
| Bone lesions — osteonecrosis | Sheep with osteonecrosis of the femoral head (ONF) induced by intraosseous injection of | Investigate the effects of hIDPSC in an animal model of ONFH. | Histological analysis showed better bone regeneration in the femoral head of hIDPSC-treated animals. hIDPSC transplantation is a promising |

FIG. 28 (continued)

| Pharmacological Efficacy or Disease Model Studies | Animal Model | Objective | Results/Conclusions |
|---|---|---|---|
| | ethanol | | conservative treatment for ONFH. |
| Cells alone (CELLAVITA™) Plus Biomaterials | | | |
| Ocular surface reconstruction | Total or partial limbal stem cell (LSC) deficiency rabbits | Investigate whether hDPSCs express specific LSC markers (in vitro study) and could be used for corneal surface reconstruction in an animal model of TLSCD (in vivo study). | hDPSCs and LSCs share similar characteristics with respect to genetic profile and differentiation capacity in corneal epithelium. hDPSCs can be used as an alternative source of LSCs and have therapeutic potential for corneal reconstruction. |
| Bone lesions—cranial bone defects | Four-month-old male Wistar rats with two full-thickness cranial defects (5 × 8 mm) on each parietal region | Evaluate the ability of hDPSCs to reconstruct large-sized cranial bone defects in rats. | hDPSCs are an additional cell source for reconstruction of bone tissues and a promising model for reconstruction of large cranial defects. |

FIG. 29

| Safety | Model | Objective | Conclusions |
|---|---|---|---|
| Teratoma formation | $5 \times 10^6$ hIDPSCs injected subcutaneously in mice (n=20) | Evaluate teratoma formation | The safety of investigational product Cellavita™ regarding teratoma formation and risk of immune rejection was established |
| *In vitro* proliferation and karyotype analysis | *In vitro* | Long-term *in vitro* proliferation to evaluate the teratogenic potential of hIDPSCs | No changes in growth pattern or karyotype morphology were observed during 25 passages. |
| Embryotoxicity | Mouse blastocysts and morulae | Analyze whether blastocysts would progress further into embryogenesis and develop human/mouse chimeras when implanted to the uterus of foster mice. | hIDPSCs survived, proliferated, and differentiated in mouse-developing blastocysts and produced human/mouse chimeras. |
| Proliferation and homing | Fetuses with gestational age ~45 days injected 1x106 GFP+ hIDPSCs intraperitoneally during ultrasound (US)-guided laparotomy | Evaluate the migration, proliferation, and homing potential of hIDPSCs during the third period of gestation in a canine model. | hIDPSCs showed high migration and proliferation potential in dog fetuses. hIDPSCs demonstrated homing, especially in fetal hematopoietic tissues (placenta, liver, and spleen), in the glandular epithelium of organs, and the perivascular niches of stem cells. Intrauterine transplantation of hIDPSCs is a viable, safe, and promising alternative for the treatment of genetic, congenital, hematological, and immunological diseases. |

COMPOSITIONS COMPRISING STEM CELLS EXPRESSING MESENCHYMAL AND NEURONAL MARKERS AND USES THEREOF TO TREAT NEUROLOGICAL DISEASE

CROSS-REFERENCE TO RELATED APPLICATIONS

The present application claims priority to and is a Continuation-In-Part of U.S. patent application Ser. No. 14/214,016 filed Mar. 4, 2014 (published as US20150050248), which claims priority to U.S. Provisional Patent Application No. 61/791,594 filed on Mar. 15, 2013 and to U.S. Provisional Patent Application No. 61/800,245 filed on Mar. 15, 2013. This application also claims priority to U.S. Provisional Applications Nos. 62/130,593, filed on Mar. 9, 2015; 62/130,585, filed on Mar. 9, 2015; and 62/220,792, filed on Sep. 18, 2015. Each of the foregoing applications is hereby incorporated by reference in its entirety.

TECHNICAL FIELD

This application relates to a composition of stem cells for the treatment of neurological diseases suitable for systemic administration.

BACKGROUND

Even though the genes responsible of neurodegenerative diseases and its protein have been identified, the mechanism of pathogenesis involved in these diseases is still unknown, which precludes the development of efficient therapeutic interventions. What is currently known is that although it is ubiquitously distributed, the mutant form of Huntington protein, for example, causes neurodegeneration and selective loss of medium spiny neurons, which preferentially occurs in the striatum and in the deeper layers of the cerebral cortex during the early phases of the disease. Thus, cell therapy has been investigated as an additional or alternative treatment which may contribute positively on the course of this disease and other similar neurodegenerative diseases. Stem cells are the essential building blocks of life, and play a crucial role in the genesis and development of all higher organisms. Due to neuronal cell death caused, for example, by accumulation of the mutated huntingtin (mHTT) protein, it is unlikely that such brain damage can be treated solely by drug-based therapies. Stem cell-based therapies are important in order to reconstruct morphological design and functional ability of neural tissue in damaged brain areas in patients. These therapies used to have a dual role: transplanted stem cells paracrine action (anti-apoptotic, anti-inflammatory, anti-scar, anti-bacterial and angiogenic actions), which stimulates local cell survival, inhibits inflammation and brain tissue regeneration through the production of bioactive molecules acting in favor of new neurons production from the intrinsic and likely from donor stem cells.

The brain-derived neurotrophic factor (BDNF) is a gene responsible for BDNF protein expression found in the brain and spinal cord. This protein promotes the survival of nerve cells (neurons) by playing a role in the growth, maturation (differentiation), and maintenance of these cells. In the brain, the BDNF protein is active at the connections between nerve cells (synapses) where cell-to-cell communication occurs. The BDNF protein helps regulate synaptic plasticity, which is important for learning and memory and is found to be expressed in regions of the brain that control eating, drinking, and body weight. Thus, BDNF has additional action in modulating all these functions. Increasing evidence suggests that synaptic dysfunction is a key pathophysiological hallmark in neurodegenerative disorders, including Alzheimer's disease. The deficits in BDNF signaling contribute to the pathogenesis of several major diseases and disorders such as Huntington's disease and depression. Thus, manipulating BDNF pathways represents a viable treatment approach to a variety of neurological and psychiatric disorders. Administration of BDNF alone offers a viable approach to treating neurodegenerative diseases. However, it is difficult to find an ideal dose for each patient because of genetic and individual polymorphism of neurodegenerative diseases manifestation. Overdoses of BDNF could induce tumor formation in the brain; on the other hand low BDNF doses could not provide an efficient treatment. Stem cells after transplantation are under the control of the patient biology, which can modulate BDNF secretion by the cells efficiently for each patient. Additionally, the studies investigating the benefits of stem cell transplantation for treating Alzheimer disease demonstrated that transplanted nerve stem cells (NSC) support the formation of new connections between host brain cells. These studies demonstrate that strengthening these connections can reverse memory losses in Alzheimer disease mouse models. It seems that BDNF, a factor naturally secreted by NSC, can replicate the effects produced by stem cell transplantation.

Once NSC is generally difficult to access and cannot be obtained in sufficient therapeutic quantities to be applied in stem cell therapy through intravenous (IV) injection. Typically, two strategies are used to increase BDNF secretion. First, is the addition of growth factors into culture medium of in vitro cultured stem cells in order to induce BDNF secretion. However, this strategy has great limitations due to the fact that stem cells produce this factor only under in vitro conditions. Consequently, when such cells are transplanted to a patient they rapidly spend the "stock" of BDNF, which prevents long term treatment of neurodegenerative disease. Another approach is to produce genetically manipulated stem cells which are suitably modified to overexpress BDNF. It is important to note that even NSC need to be genetically engineered to produce therapeutically sufficient levels of BDNF. However, gene modification has its roots in gene therapy—an approach that still has to be proven. Therefore, there is a great need for new cell types and cell culture methods which can lead to stem cells with elevated secretion of BDNF.

The subventricular zone (SVZ) is the unique brain area where new neurons are produced throughout life (Altman J and Das G D 1965) and in generating cells to function in repair through adulthood. Blood vessels immediately subjacent to the SVZ run parallel to the direction of tangential neuroblast migration, and guide migratory neuroblasts via BDNF signaling. It is now understood that the organization of the SVZ in the adult human brain differs significantly from that of any other studied vertebrates. Specifically, this region in the adult human brain contains a unique tape of astrocytes that proliferate in vivo and can function as NSC in vitro. Astrocytes in the central nervous system perform many important and diverse functions. They are involved in formation of the neuro-vascular unit which is composed of a neuron, an astrocyte and a blood vessel. Astrocyte processes extend to and interact with blood vessels. Astrocytic endfeet are in intimate contact with the basal lamina that is a component of the vessel wall and together with endothelial cells they form the blood-brain barrier (BBB). Isolation of stem cells, which have a capacity to migrate and home in a neurogenic niche as well as around blood vessels in the adult human brain, further being able to differentiate into neurons and glial cells, is a basis for the development of novel neurodegenerative cell therapies.

Dopamine (DA) is a major neurogenesis factor in the adult SVZ (Baker et al., 2004). The proximity of the SVZ with the striatum makes it a neurodegeneration therapy target for striatum-neurodegeneration associated disorders such as Huntington's disease (HD) and Parkinson's disease (PD). Both pathologies are characterized by different clinical symptoms of motor dysfunction, and both are thought to involve the SVZ—striatum DA micro-circuitry path through different mechanisms. The disease-generated DA innervation that occurs in HD is a natural protective feedback mechanism to compensate for the striatal internal neurons degeneration pathology caused by inherent genetic mutation (Parent M et al., 2013). Dysregulation of DA receptor D2 is a sensitive measure for Huntington disease pathology in model mice (Crook et al., 2012; Chen et al., 2013). In contrast, PD is associated with massive degeneration of DA neurons, due to impaired neurogenesis in the nigrostriatal area and is a major cause of the pathology (Hoglinger et. al., 2004).

The initial inflammatory response occurs in the body to limit the invasion of foreign bacteria or viruses or parasites and to defend tissues against molecular foes which are further removed from the organism by anti-inflammatory mechanisms. However, chronic inflammation (CI) is a double-edged sword. CI is long lasting event and it continuously harms and kills healthy cells as, for example, in rheumatoid arthritis where the inflammation becomes self-sustaining.

In neurodegenerative diseases several molecules of the protein are tightly aggregated together inside the cell, which pathologists call an "amyloid" structure, and they are apt to clog the brain. Such proteins were found in Alzheimer's disease—amyloid beta and tau; in Parkinson's disease—alpha synuclein, and in Huntington's disease—huntingtin. These aggregates often form large insoluble deposits in the brain. However, the truly toxic ones are considered the small, soluble aggregates of these proteins. Due to the accumulation of these aggregates in the brain, chronic inflammatory reactions remained in many age-related neurodegenerative disorders among which are aforementioned diseases (Nuzzo et al., 2014).

Degenerated tissue, the presence of damaged neurons and neurites, highly insoluble amyloid β peptide deposits, and neurofibrillary tangles in the brains of Alzheimer disease (AD) carriers provide obvious stimuli for inflammation (Zotova et al., 2010; Schott and Revesz, 2013).

Many studies have suggested that the chronic inflammation observed in AD accelerates the disease process and may even be a disease trigger. A history of head injury and systemic infections are factors, which typically cause brain inflammation and are known to be risk factors for AD. Excessive action of the brain's immune cells, which are glial cells, is another hallmark of Alzheimer's disease. Although it has been suggested that inflammation is associated with injury and toxicity to neurons, the relationship among glial cells, neurons and amyloid plaques still remains unclear. Inflammatory mediators released by glial cells can be extremely toxic to neurons. Thus, they have been considered as mediators of neurodegeneration.

Two closely related inflammation-promoting proteins, IL-12 and IL-23, are among those pumped out by microglia when the cells become immunologically active. The studies demonstrated that these proteins exist at elevated levels in the cerebrospinal fluid of AD patients. Blocking these inflammatory proteins in older Alzheimer's mice whose brains were already plaque-ridden reduced the levels of soluble, more toxic forms of amyloid beta and reversed the mice's cognitive deficits (Vom Berg et al., 2012; Griffin, 2013).

More recently, other anti-inflammatory approaches such as the blocking of a protein NLRP3 and microglial protein MRP14 have been described and also seem to work well in the same Alzheimer's mouse model. These approaches reduce brain inflammation, amyloid beta deposition, and cognitive impairments. In Alzheimer's mice that were genetically engineered to lack NLRP3, microglia were reversed back towards a non-inflammatory state in which they consume much more amyloid beta and secrete neuron beneficial proteins. In another study, a microglia protein MRP14 was targeted, which also helped to reverse microglia to a non-inflammatory state (Heneka et al., 2013; Zhang et al., 2012).

The other factor which is critical for AD is aging. Aging may help trigger Alzheimer's by worsening common age-related problems with neurons, which become functionally deficient and lose their ability to transport and appropriately place proteins. Inflammation worsens this problem by increasing the production of amyloid-beta in inflamed regions, stressing neurons, and hastening the age-related decline of their protein-transport and disposal systems. Inflammation reactivates microglia into an inflammatory state and thus reduces their ability to clear up the brain (Swindell et al., 2013).

Currently, it is assumed that inflammation helps to start the AD process by increasing the production of amyloid beta. The inflammation seems to be self-sustaining in AD because it reduces the ability of microglia to remove amyloid beta. Therefore, constant deposition of amyloid beta does not allow the inflammation to resolve, which gets worse in aged AD carriers (Akiyama et al., 2000; Vom Berg et al., 2012; Zang et al., 2012; Griffin, 2013; Heneka et al., 2013; Swindell et al., 2013; Schott and Revesz, 2013).

The contribution of inflammation to neurodegeneration in Huntington disease (HD) is strongly suggested; however it is less studied then in AD (Soulet and Cicchetti, 2011; Ellrichmann et al., 2013). Thus, an activation of the immune system in HD was clearly proven by the elevated expression of pro-inflammatory cytokines, which are crucial to the body's immune response, such as, IL-6 and TNF-alpha. These pro-inflammatory cytokines were significantly increased in the striatum, plasma and CSF in mouse models and in symptomatic as well as presymptomatic HD patients. Additionally, innate immune cell hyperactivity was detected through elevated IL-6 production in mutant mHTT expressing myeloid cells of the central (microglia) and peripheral innate immune system (monocytes and macrophages) both in HD patients and mouse models. It has also been reported that abnormally high levels of cytokines were present in the blood of people carrying the HD gene many years before the onset of symptoms (Bjorkqvist et al., 2008; Trager et al., 2014a, b). The composition of cytokines and levels of their expression, which can be measured in a blood of patients, could be useful to establish the need to initiate intervention for therapies as well as the timing of therapies.

Blood cells, due to the presence of the abnormal HD protein (huntingtin) inside the cells, were hyperactive in HD patients, as well as microglia in the brain, thus suggesting that abnormal immune activation could be one of the earliest abnormalities in HD. The patient's blood signature could provide a new insight into the effects of the HD in the brain as well as markers of HD severity. Anomalous immune activation could be a target for future treatments aimed at slowing down HD (Soulet and Cicchetti, 2011, Ellrichmann et al., 2013).

Parkinson's disease is characterized by a slow and progressive degeneration of dopaminergic neurons in the substantia nigra. Using animal models researchers have obtained consistent findings about involvement of both the peripheral and the central nervous system immune components in response to inflammation, which initiates an immune response in PD. The presence of continuing and increasing pro-inflammatory mechanisms results in a process whereby cellular protective mechanisms are overcome and the more susceptible cells, such as the dopaminergic neurons, enter into cell death pathways, which leads to a series of events that are a crucial for the progression of PD (Doursout et al., 2013). Inflammatory responses also manifested by glial reactions, T cell infiltration, and increased expression of inflammatory cytokines, as well as other toxic mediators derived from activated glial cells, are well known features of PD. More recent in vitro studies, however, proposed that activation of microglia and subsequently astrocytes via mediators released by injured dopaminergic neurons is involved, even though they are unlikely to be a primary cause for neuronal loss (Hirsch et al., 2003). In patients the epidemiological and genetic studies support a role of neuroinflammation in the pathophysiology of PD. Post mortem studies confirm the involvement of innate as well as adaptive immunity in the affected brain regions in patients with PD. Activated microglial cells and T lymphocytes have been detected in the substantia nigra of patients concomitantly with an increased expression of pro-inflammatory mediators (Tufekci et al., 2012; Hirsch et al., 2012). Another study, which enrolled 87 Parkinson's patients between 2008 and 2012, together with 37 healthy controls measured markers of inflammation such as C-reactive protein (CRP), interleukin-6, tumor necrosis factor-alpha, eotaxin, interferon gamma-induced protein-10, monocyte chemotactic protein-1 (MCP-1) and macrophage inflammatory protein 1-beta in routine blood tests. All participants underwent physical exams as well. This study demonstrated that the degree of neuroinflammation was significantly associated with more severe depression, fatigue, and cognitive impairment even after controlling for factors such as age, gender and disease duration (Lindqvist et al., 2013). Neuroinflammatory processes might represent a target for neuroprotection, and anti-inflammatory strategies may be one of the principal approaches in the treatment of PD.

Multiple approaches have been tested to repair neurodegeneration-associated CNS diseases, including clinical motor dysfunction diseases (Wernig M, et al., 2011). Stem cells sources used for neuro-regeneration cell therapy include mesenchymal stem cells (MSC), neural progenitor cells (NP), human fetal neuronal stem cells (huNSC), and pluripotent stem cells (both embryonic (ESCs) and induced (iPSC)). Most of the studies on cell therapy for neurological conditions used neuronal-like cells through major cellular manipulation and/or highly invasive methods of delivery. For example, WO 2008/132722 and US Patent Application Publication No. 2013/0344041 disclose genetically manipulated stem cells to induce stem cell traits or to release neurotrophic factors; WO 2009/144718 and US Patent Applications Publication Nos. 2014/0335059 and 2014/0154222 disclose inducing the release of neurotrophic factors at levels higher than at non-induced stage via exposure to biological, natural or chemical compounds in culture; and other studies use immortalized cell line of fetal stem cells that express early markers of neuronal differentiation. In spite of the studies on stem cell therapy, no data have shown that stem cell therapy through intravenous (IV) injection can result in direct neurogenesis via BDNF secretion or D2 expression in brain compartments suffering from neurodegenerative disease.

SUMMARY OF THE INVENTION

In one embodiment, the invention is directed to a pharmaceutical composition comprising stem cell, wherein the stem cells comprising late harvest enriched from tissue of neural crest origin. In some implementations, the tissue of neural crest origin is dental pulp. In some aspects, the stem cells enriched from tissue of neural crest origin are immature dental pulp stem cells (IDPSCs). Early harvest stem cells enriched from tissue of neural crest origin comprise IDPSCs of the first fifteen or the first 25 harvest cycles whereas late harvest stem cells comprise IDPSCs from the sixty or later or the 26th or later harvest cycle.

In some embodiments, the invention is directed to a pharmaceutical composition produced by a method comprising: extracting dental pulp (DP) from a tooth; culturing the DP in basal culture medium in a first container to establish a DP explant culture, wherein the DP explant culture is cultured without or with at least one extracellular matrix components selected from the group consisting of: fibronectin, collagen, laminin, vitronectin, polylysine, heparan sulfate proteoglycans, and enactin; mechanically transferring the DP to a second container to establish a second DP explant culture; repeating the step of mechanically transferring the DP until at least 15 DP explant cultures have been established; passaging the DP explant culture to produced a passaged DP culture; and combining the passaged DP culture of an early harvest population and an late harvest population to produce the pharmaceutical composition, wherein the early harvest population comprises passaged DP culture established from at least one of the first 15 DP explant cultures and the late harvest population comprises passaged DP culture established from at least one of the DP explant cultures after the 15th DP explant culture. In some implementations, the culturing step occurs under hypoxic conditions. In some implementations, the step of combining the passaged DP culture of the early harvest population and the late harvest population to produce the pharmaceutical composition comprises: simultaneously thawing the frozen stock of passaged DP cultures of the early harvest population and the late harvest population; and pooling the thawed passaged DP culture to produce the pharmaceutical composition.

For some embodiments of the pharmaceutical invention, culturing the DP in basal culture medium in the method of production persist for at least three days before the DP is mechanically transferred. In some implementations, the method of production further comprise creating a frozen stock of the passaged DP culture. In some aspects, the frozen stock of the passaged DP culture is created at the third passage of the DP explant culture.

In some embodiments, the invention is directed to a pharmaceutical composition produced by a method comprising: extracting dental pulp (DP) from a tooth; culturing the DP in basal culture medium in a first container to establish a DP explant culture, wherein the stem cells comprising late harvest enriched from tissue of neural crest origin are double positive for CD44 and CD13. In some aspects, the stem cells enriched from tissue of neural crest origin and double positive for CD44 and CD13 are immature dental pulp stem cells (IDPSCs).

In some embodiments, the invention is directed to a pharmaceutical composition produced by a method comprising: extracting dental pulp (DP) from a tooth; culturing the DP in basal culture medium in a first container to establish a DP explant culture, wherein the stem cells comprising late harvest enriched from tissue of neural crest origin demonstrated increasing level of secretion of endogenous BDNF and/or other neurotrophic factors (NF3, NF4 and NF5), when compared to stem cells obtained from early harvest. In some aspects, the stem cells enriched from tissue of neural crest origin and secreting high level of endogenous BDNF and/or other neurotrophic factors (NF3, NF4 and NF5) are immature dental pulp stem cells (IDPSCs).

The present invention relates to pharmaceutical compositions for systemic administration to a subject to treat a neurological condition. The neurological disease or condition may be a neurodegenerative disease or condition, autism, schizophrenia, epilepsy, stroke, ischemia, a motor disorder, or a convulsive disorder. Neurodegenerative disease or condition may be Parkinson's disease (PD), multiple sclerosis, epilepsy, amyotrophic lateral sclerosis (ALS), stroke, autoimmune encephalomyelitis, diabetic neuropathy, glaucomatous neuropathy, Alzheimer's disease, or Huntington's disease (HD).

In some implementations, the pharmaceutical compositions comprise stem cells from tissue of neural crest origin. Tissue of the neural crest origin may be dental pulp but not limited by this example.

In one embodiment, the pharmaceutical composition comprises stem cells expressing at least one safety markers selected from the group consisting of ATP-binding cassette sub-family G member 2 (ABCG2), p53, and inactive nanog. Inactive nanog is expressed nanog localizing predominantly in the cytoplasm of the stem cell. In some aspects, at least 75% of the stem cells express ABCG2, at least 75% of the stem cells express p53, or no more than 5% of the stem cells express inactive nanog. Some pharmaceutical compositions may comprise stem cells that further express the safety marker SOX2. In some such embodiments, no more than 30% of the stem cells express SOX2.

The stem cells of the pharmaceutical composition may further secrete at least one marker selected from the group consisting of brain-derived neurotrophic factor (BDNF), neutrotrophin-3 (NT3), neutrotrophin-4 (NT4), neutrotrophin-5 (NT5), and p75. In some such embodiments, the stem cells of the pharmaceutical composition express BDNF, NT3, NT4, NT5, and p75 (CD271).

In another embodiment, the pharmaceutical composition comprises stem cells expressing at least one neuroepithelial stem cell marker selected from the group consisting of BDNF, NT3, NT4, NT5, and p75. In some aspects, these pharmaceutical compositions comprise undifferentiated stem cells expressing BDNF, NT3, NT4, NT5, and p75. These pharmaceutical compositions may further express at least one safety markers selected from the group consisting of ABCG2, inactive nanog, p53, and SOX2. In some aspects, at least 75% of stem cells express the at least one marker when the at least one marker is ABCG2. In some aspects, at least 75% of the stem cells express p53. In some aspects, no more than 5% of the stem cells express inactive nanog. In some aspects, no more than 30% of the stem cells express SOX2.

In some aspects, the stem cells of the pharmaceutical composition are immature dental pulp stem cells (IDPSCs).

The present invention also relates to methods of using the pharmaceutical composition comprising systemically administering to a subject the pharmaceutical compositions of the invention. Such methods may be used for treating neurological diseases or conditions, for example by supporting the natural neuro-protective mechanism in subjects diagnosed with early HD or repairing lost DA neurons in subjects diagnosed with PD. The methods may also be used as a preventive therapy for subjects at risk of HD.

In some implementations, the methods further comprise measuring the amount of DA receptor in the subject. In some aspects, the DA receptor is receptor D2. In some embodiments, measuring the amount of DA receptor, for example receptor D2, in the subject comprises imaging the subject to detect presence of DA receptor.

In some aspects, the subject is administered a single administration or a first and second administrations of the pharmaceutical composition. The repetitive (from 1 to six) administrations of the pharmaceutical composition take place at least seven days, at least 14 days, at least 21 days, or at least 30 days after the first administration, as well as one time per year, or twice per year. In some implementations, administration of the pharmaceutical composition is through intravenous injection. In some implementations, the administration of the pharmaceutical composition may be repeated annually, for example, repeated three times.

In one embodiment of the methods, the neurological disease or condition is treated by the stem cells crossing the blood/brain barrier (BBB) and inducing neurogenesis. In some aspects, the stem cells are directly transplanted into the brain parenchyma, including striatum, following crossing of the BBB. In some embodiments, the induced neurogenesis is dopamine-associated. For example, dopamine-associated neurogenesis occurs through self-differentiation of the stem cells or activation of migration and differentiation of intrinsic stem cells by the extrinsic stem cells. In some aspects, massive dopamine-associated neurogenesis takes place in the subventricular zone (SVZ).

In some embodiments of the methods, the pharmaceutical composition provides neuroprotection. For example, systemic neuroprotection is provided with the high basal level of neurotrophic and immunoprotective factors expression and release pattern of the stem cells of the pharmaceutical composition. In some aspects, these stem cells of the pharmaceutical composition are IDPSCs.

In some implementations of the methods, the pharmaceutical composition comprises stem cells that are autologous to the subject. For example, the stem cells that are autologous to the subject are collected from the subject before disease manifestation from contingently "healthy cells", once these diseases are genetic and age dependent. In other implementations, the pharmaceutical composition comprises stem cells that are allogeneic to the subject regardless of whether the major histocompatibility complex expressed by the stem cells match the major histocompatibility complex expressed by subject. The pharmaceutical composition may also comprise a combination of stem cells that are autologous to the subject and stem cells that are allogeneic to the subject.

BRIEF DESCRIPTION OF THE DRAWINGS

FIG. 15 depicts immunohistochemical images showing positive anti-human nuclei (hNu) staining of hIDPSCs and their localization in rat brain tissue 30 days after hIDPSC administration. Note: a few hIDPSCs in the cortex (left) and a large number of hIDPSCs in the corpus striatum (right). Light microscopy. 90× magnification. Scale bars: 5 μm and 25 μm, respectively.

FIG. 28 depicts pharmacological efficacy studies of investigational product CELLAVITA™ (stem cells).

FIG. 29 depicts safety studies of investigational product CELLAVITA™ (stem cells).

DETAILED DESCRIPTION

Figure 1:
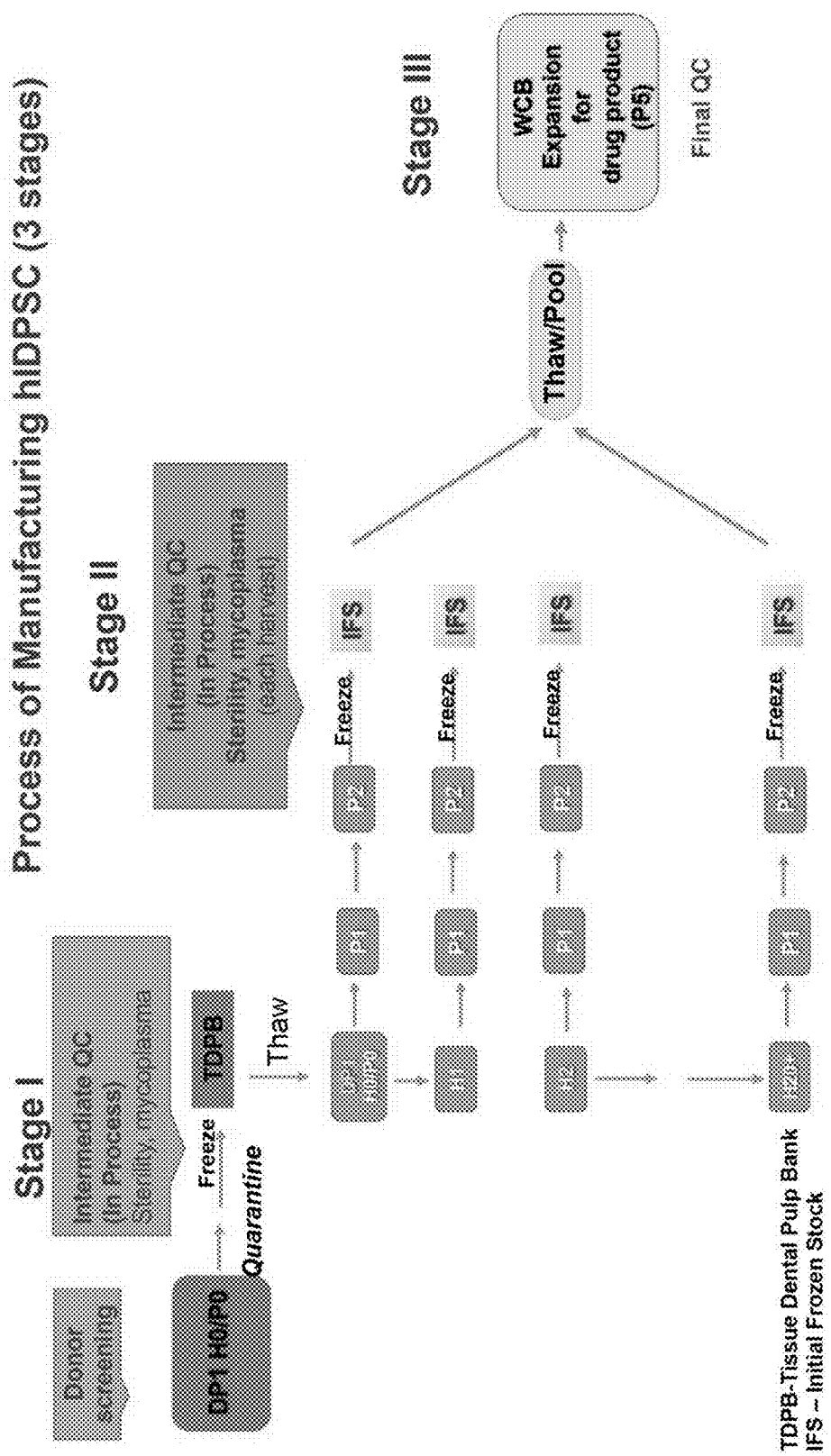
FIG. 1 depicts a scheme for the manufacturing process of compositions of IDPSCS comprising both early and late population IDPSC suitable for the treatment of neurological diseases and conditions.

As used herein, the verb "comprise" as is used in this description and in the claims and its conjugations are used in its non-limiting sense to mean that items following the word are included, but items not specifically mentioned are not excluded. In addition, reference to an element by the indefinite article "a" or "an" does not exclude the possibility that more than one of the elements are present, unless the context clearly requires that there is one and only one of the elements. The indefinite article "a" or "an" thus usually means "at least one".

As used herein, the term "high expression" in reference to the expression level (strongly immunopositive for antigen of interest) of a gene in a population of cells refers at least 75% of the population expressing the gene.

As used herein, the term "low expression" in reference to the expression level of a gene in a population of cells refers no more than 30% of the population expressing the gene. In preferred embodiments, low expression refers no more than 25% of the population expressing the gene.

As used herein, the term "no expression" in reference to the expression level of a gene in a population of cells refers no detectable cells that express the gene of interest in the population. No detectable expression includes an expression level that is within the realm of error for the method of measuring expression.

As used herein, the term "subject" or "patient" refers to any vertebrate including, without limitation, humans and other primates (e.g., chimpanzees and other apes and monkey species), farm animals (e.g., cattle, sheep, pigs, goats and horses), domestic mammals (e.g., dogs and cats), laboratory animals (e.g., rodents such as mice, rats, and guinea pigs), and birds (e.g., domestic, wild and game birds such as chickens, turkeys and other gallinaceous birds, ducks, geese, and the like). In some implementations, the subject may be a mammal. In other implementations, the subject may be a human.

As used herein, the term, "stem cell" refers immature, unspecialized cells that, under certain conditions, may differentiate into mature, functional cells.

As used herein, the term, "neural stem cell" or "NSC" refers to multipotent cells that self-renewable and able to terminally differentiate into neurons, astrocytes, and oligodendrocytes.

As used herein, the term "neural progenitor cells" refer to undifferentiated cells further along the stage of cell differentiation than neural stem cells. Thus these cells are derived from neural stem cells and can produce progeny that are capable of differentiating into more than one cell type of central nervous system (CNS) and peripheral nervous system (PNS).

As used herein, the term "neural precursor cell" or "NPC" refers to a mixed population of cells consisting of neural stem cells and all of its undifferentiated progeny. Therefore NPCs include both NPC and NSC. The NPCs can also be categorized into neuronal NPCs and glial NPCs, which produce neurons and glial cells, respectively.

As used herein, the term "harvest cycle" constitutes a transfer of the orgão (e.g. of neural crest origin like dental pulp) or tissue to a new cell culture container after adherence and outgrowth of the stems cells in the tissue followed by preservation (e.g. cryopreservation) and/or sub-culturing of the outgrowth of IDPSCs. Stem cells isolated from the first time from organ culture (dental pulp) using explant technology are early populations, thus stem cells isolated from the first harvest cycle (first transfer of organ culture) are early population cells. For example, of stem cells isolate from dental pulp tissue, stem cells from human exfoliated deciduous teeth (SHED) can not be divided in early and late population, as these cells are isolated using enzymatic method only once from dental pulp, which are descarted after SHED isolation. Thus, only one SHED cell population can be isolated. Further, following enzymatic digestion, SHED can be passed from one to other cell culture flask thus counting cell passages, which generally are performed when SHED reach semi-confluence.

In contrast to SHED for immature dental pulp stem cells (IPDSCs) enzymatic method is not used. IDPSCs can be isolated as from explant culture of the dental pulp after the first adherence of DP to plastic and cells outgrowth—early population cells. At this stage dental pulp is not descarted and used for subsequent explant dental pulp cultures—late populations. Thus, IDPSC isolated from the second or later harvest cycle are late population cells. For example, IPDSCs that are isolated from the second harvest cycle or later are late population undifferentiated stem cells. As used herein, the term "early passage" refers to the cells from the first five passages of an explant culture. As used herein, the term "late passage" refers to the cells from passages after the fifth passage, e.g. in the sixth passage or later, of an explant culture. Thus, the IDPSC may be from an early or late population and additionally categorized as an early or late passage.

The present invention relates to the discovery that a particular composition of IDPSC, the unique stem cells population, which composed by early and late stem cells populations, from tissue of neural crest origin can cross the blood/brain barrier (BBB) and induce neurogenesis. Tissue of neural crest origin include, for example, dental, periodontal, and hair follicular tissue. Hair follicular tissue includes follicular tissue of the vibrissa.

The hIDPSC was evaluated in the 3-NP (three nitropropionic acid) HD rat model. The hIDPSC showed engraftment into the rat brain after 1 month following intravenous injection of $1 \times 10^6$ and $1 \times 10^7$ cell/transplant ($3 \times 10^6$ cell/kg and $3 \times 10^7$ cell/kg) labeled with fluorescent protein (Vibrant), as well as, following immunohistochemistry analysis using specific anti-human antibody. Cell engraftment was observed in different brain compartments (cortex, striatum and Subventricular zone-SVZ).

The ability to cross the BBB enables systemic administration (e.g. IV administration) of stem cell therapy to treat neurological conditions, which provides a significant advantage over more localized methods of administration. In addition to systemically administration being less invasive, leaving stem cells to migrate to locations that require aid reduces the risk of harmful cell masses developing at the site of administration. For example, while intrathecal (IT) administration of stem cell therapy is commonly contemplated in preclinical and clinical studies, this method can have significant risk when the stem cells are MSCs. It has been reported that depending on cellular density, bone marrow-derived MSCs that were drawn into brain parenchyma (presumably in response to chemoattractant signals from this inflammation) via intracerebroventricular (ICV) formed cellular masses in 64% of severe experimental allergic encephalomyelitis animals. Karyotypically normal MSCs at early passages also induced masses in naïve animals (Grigoriadis et al., 2011). Therefore, MSCs implanted directly within the CNS may by themselves produce local pathology of yet unknown consequences (Snyder et al., 2011). The volume of these masses appeared to correlate with cellular density. Therefore cell number as well as number of application can be limited and risky factors for IT and ICV applications in contrast to IV.

The composition of IDPSC may be in the form of a pharmaceutical composition comprising stem cells expressing a mesenchymal and neuroepithelial stem cell immunophenotypes. In some implementations, expressing a mesenchymal and a neuroepithelial stem cell molecular profile is the expression of markers of MSC and neuroepithelial cells/progenitor cells and genes encoding neuro-protective and immunoprotective factors.

Cells expressing a MSC immunophenotype include expression of CD44. Prior animal models of multiple sclerosis found that NCS adhesion to inflamed endothelial cells and then trans-endothelial migration across the BBB into the inflamed CNS areas are sequentially mediated by the constitutive expression of functional cell adhesion molecules (CAM), especially CD44 (Rampon C et al., 2008). Although the exact mechanism of how hIDPSC are able to cross BBB is not clear, it is believed that these cells have this capacity because they have perycite-like characteristics (Barros et al., 2014). Perycites are known to play a critical role in the integration of endothelial and astrocyte functions at the neurovascular unit, and in the regulation of the BBB (Armulik et al., 2010; Liu et al., 2012). According to a previous study (Yilmaz et al., 2011), mesenchymal stem cells (MSC) can engraft into brain after systemic administration due to expression of CD44, which is a ligand of E and L blood vessel endothelial selectins (Dimitroff, et al., 2001). MSC present similar homing mechanisms as leukocytes. The first step of leukocyte migration involves capture of leukocytes flowing freely in the blood stream, mediated by glycoproteins known as selectins. P- and E-selectins are expressed by the vascular endothelium and are the principal mediators for the rolling response in leukocyte migration through blood vessels (Luster et al., 2005). MSC may use this or similar mechanisms to engraft in several organs (Sackstein et al., 2008) such as the brain. Thus, CD44 is considered a pivotal factor for MSC migration into the brain. Similarly to BM MSC, hIDPSC express CD44, which suggests that CD44 is also involved in hIDPSC migration towards several organs (Barros et al., 2014, Castanheira et al., 2013) including the brain after intravenous administration. Surprisingly, that, hIDPSC express also CD13, (aminopeptidase N) (Kerkis et al., 2006; Kerkis and Caplan, 2012), which is multifunctional protein and plays varying roles in cell migration, cell proliferation, cell differentiation (Taylor et al., 1993; Mina-Osorio et al., 2008a/b). CD13 participates in angiogenesis generating and modulating angiogenic signals, in the process of capillary tube formation, and as a marker of angiogenic vessels (Bhagwat et al., 2001). This suggests its possible role in hIDPSC capacity to migrate and to target brain vasculature. In the 3-NP rat study, hIDPSC demonstrated tight association with brain capillaries.

In some embodiments, the IDPSC lack expression of CD146, HLA-DR, and/or HLA-ABC. Lack of expression of these markers facilitates the use of hIDPSC as a safe, heterologous therapy. The endothelium plays an important role in the exchange of molecules, but also of immune cells between blood and the underlying tissue. The endothelial molecule S-Endo 1 antigen (CD146) is preferentially located at endothelial junctions and has been claimed to support endothelial integrity. Thus, in humans, MCAM (CD146) is expressed in T cells (3%) in the peripheral circulation of healthy individuals. MCAM positive T cells also demonstrate an increased ability to bind to endothelial monolayers and these cells could represent early components of the adaptive immune response (Dagur et al., 2015). Therefore, stem cells, which express this marker may bind to BBB and not cross BBB, as well as being immune reactive. The mesenchymal stem cell genotype pattern also includes low expression of pluripotent markers OCT3/4 and nanog. Interesting, the undifferentiated stem cells of pharmaceutical composition of the invention need not express c-Myc, KU-4, and REX-1. In fact, these stem cells may be negative for c-Myc, KU-4, and REX-1.

Stem cells expressing a neuroepithelial stem cell molecular profile express at least one, preferably two, more preferably more than two NPC- and NSC-biomarkers selected from the group consisting of vimentin, nestin, SOX2, p75, and other neurotrophic factors essential for neural cells development and survival. p75 is a neurotrophic receptor marker. In the recent works, it was hypothesized that normalization of p75NTR and/or TrkB expression or their signaling will improve BDNF (brain-derived neurotrophic factor) neuroprotective therapies in Huntington's disease (Brito et al., 2013).

Exemplary neurotrophic factors essential for neuronal development and survival include BDNF (brain-derived neurotrophic factor), GNDF (glial cell line-derived neurotrophic factor), NGF (nerve growth factor), and NTs (neurotrophins). BNDF plays a critical role in Huntington's disease (Gauthier et al.; Strand et al.) and Parkinson's disease (Mogi et al.), both of which are dopamine-associated neurodegenerative diseases. Several studies demonstrate that wild-type HD-overexpressed htt protein increases BDNF expression in CNS cells, whereas the mutated htt protein leads to down-regulation of BDNF, resulting in insufficient neurotrophic support and neuronal cell death (Zuccato et al., 2001). The brains of AD patients have reduced NGF levels (Calissano et al.); however, NGF administration can partially reduce cholinergic atrophy in aged rodents (Fischer W et. al). In some embodiments, the preferred NGF is NGF-β. NTs essential for neuronal development and survival include NT3, NT4, or NT5. NT4 and NT5 are known to promote sensory and motor axon growth.

In some implementations, the stem cells comprise cells autologous to a subject in need of the pharmaceutical composition. In other implementations, the stem cells comprise cells allogeneic to the subject in need of the pharmaceutical composition. In some implementations, stem cells comprise a combination of cells autologous to and allogeneic to the subject in need of the pharmaceutical composition.

In one embodiment, the composition of stem cells is isolated from tissue of neural crest origin selected from the group consisting of dental tissue, periodontal tissue, and hair follicular tissue. In preferred embodiments, the tissue of neural crest origin is dental pulp. In a most preferred embodiment, the stem cells are from immature dental pulp, for example, human immature dental pulp stem cells (IDPSCs) as disclosed in International Application no. PCT/IB14/59850 and U.S. patent application Ser. No. 14/214, 016. IDPSCs carry multiple neuronal markers and undergo robust differentiation into neurons. The novelty of IDPSC immunophenotype is unexpected expression of these markers and at the same time markers typical for MSC, presenting immunophenotype in accordance with the International Society for Cellular Therapy's minimal criteria for defining multipotent mesenchymal stromal cells (Dominici et al., 2006). This combination of expression by IDPSC of MSC and multiple neuronal markers is not typical for MSCs (Dominici et al., 2006) and which has not been disclosed for MSCs.

Pharmaceutical compositions contemplated in the invention are preferably isotonic. For intravenous injection, the population of immature stem cells should be between $10^4$-$10^{10}$ cells per injection, for example, $10^4$, $10^5$, $10^6$ and $10^7$ cells per kg of body weight. The pharmaceutical composition comprising a population of stem cells may be used in adjunction to other pharmaceutically active compounds or modalities. Thus in some embodiments, the pharmaceutical composition may further comprise another pharmaceutically active compound or therapeutic modality.

Mesenchymal Stem Cells

In the body, MSCs are found in bone marrow, umbilical cord tissue, dental pulp and fat pads. However, in bone marrow MSCs are relatively rare, comprising only one out of every 10,000 cells, while other sources are significantly richer in these cells. In organism MSCs are responsible for tissue regeneration in cases of disease, trauma or injury throughout human life. This function of MSCs is mediated by their capacities for self-renewal and plasticity (the capacity for differentiation—production of diverse cell types). MSCs can be isolated from aforementioned tissues and cultured easily in the laboratory. After obtaining a limited number of the cells from a patient, MSCs can be multiplied rapidly in vitro and cryopreserved for the future clinical applications.

MSCs are able to secrete a variety of bioactive molecules, such as cytokines, which provide "trophic activities" by structuring a regenerative microenvironment, and other molecules that contribute to immunomodulatory cell functions and even to transfer products as large as mitochondria to damaged cells that need help. When transplanted in vivo, MSCs in response to chemotactic stimuli, can migrate to the focal injury from both local and surrounding sites. Additionally, MSCs can act to reduce chronic inflammation, to inhibit apoptosis, to provide the appearance of myofibroblasts, to inhibit scar formation and to stimulate the mitosis of tissue-intrinsic progenitors, thus remodeling damaged tissue. That is why MSCs are also called "Medicinal Signaling Cells." They stimulate angiogenesis, the process of new blood vessel formation, which is closely linked to neurogenesis, the process by which new nerve cells are produced. Blood vessels play an important role as a framework for neuronal progenitor cells migration toward the damaged brain region The factors secreted by MSCs also reduce the destructive effects of oxidative harm. Using all these mechanisms of action MSCs can significantly improve lesioned microenvironment that leads to restoration of the damaged cells. Therefore, MSCs are believed to be "cellular paramedics".

When MSCs obtained from humans were labeled, in order to track them, and injected into mice that had some type of tissue damage, they migrated throughout the damaged tissues apparently evenly. These cells can or not to be present in the tissue for a substantial period of time, which depends on disease model. The continued presence of MSCs is important, but not essential, to therapeutic development because it indicates that potential positive long-term effects of a treatment might be capable of persisting.

It is important to understand, that temporary presence of MSCs is not a result of the host immune system action, because the experiment in injured mice, with or without functional immune systems yielded the same results. Further investigations demonstrated that MSCs suppress the immune system and reduce inflammation. In other words, MSCs can be transferred between organisms demonstrating very low immune rejection, which occurs when the immune system of the organism attacks the foreign tissue, receiving the transplant. This finding makes MSCs good candidates for transplantation or injection into a host because they can avoid rejection by the host's immune system (Le Blank, Ringden, 2006; English, 2012; Miguel et al., 2012; Griffin et al., 2012; Ankrum et al., 2014).

The crucial question of cellular therapies is a route of MSCs delivery into the brain, which has been approached in a number of different ways. Several approaches have been proposed to deliver MSCs into the brain such as, intrathecal, intravenous, an injection into the space surrounding the spinal cord and even a route through the nose. In early development, as a result of complex multicellular interactions between immature endothelial cells and neural progenitors, neurons, radial glia, and pericytes, which shared similar features with MSCs, the blood/brain barrier (BBB) is formed and it controls selective molecular or cells trafficking between the bloodstream and brain interstitial space. The BBB present significant problems for the delivery of therapeutic agents (drugs or cells) for treating brain malignancies and neurodegenerative disorders. Systemically-infused MSCs may treat acute injuries, inflammatory diseases, stroke of the central nervous system (CNS) and even brain tumors because of their regenerative capacity and ability to secrete trophic, immune modulatory, or other engineered therapeutic factors. However, whether MSCs possess the ability to migrate across the BBB in normal and pathological conditions remains unresolved (Liu et al., 2013).

Systemic infusion (e.g. IV) of MSCs expanded in vitro is minimally invasive and convenient procedure that is used in the large number of ongoing clinical trials. Therefore, it is essential to understand if transplanted MSCs can home and engraft at ischemic and injured sites in the brain to exert their therapeutic effects. No data has yet to suggest or disclosed that systemic delivery of minimally manipulated MSCs may result in direct transplantation of cells into the brain through the BBB.

The simplicity with which MSCs can be obtained, cultured, as well as their unique "trophic activities" and possibility of their transfer into a host without immune rejection are the reasons why stem cell therapy with MSCs is a promising avenue to for treating neurological diseases and conditions, for example neurodegeneration. According to recent publications, MSCs can support repair neurodegeneration by secreting trophic factors, which are proteins that stimulates differentiation and survival of cells. The effects of these factors allow nerve cells to carry out several processes that can support survival: axon extension, growth, and cells attachment. Although are evidences that MSCs can promote cell growth and repair in the brain, it is not yet definitively confirmed that MSCs can become mature nerve cells with the ability to signal, or communicate with, other nerve cells.

Previous studies have tested the potential of MSC therapy in HD animal models (chemical models where HD is induced by QA or 3-NP and transgenic mouse lines R6/2-J2, N171-82Q, and R6/2). However, while the authors called the cells tested MSCs, these cells were not confirmed as having the immunophenotype typical for MSCs as defined by the International Society for Cellular Therapy (Dominici et al., 2006). These pre-clinical studies used allogeneic and xenogeneic primary culture and immortalized cell lines from the bone marrow, adipose tissue, and umbilical cord blood grown under normal levels of oxygen (normoxia) or under low levels of oxygen (hypoxia), as well as, mononuclear cells. Thus these studies have not established that cells considered as MSCs by the International Society for Cellular Therapy may be successfully employed to treat neurological diseases without previous special manipulation in culture.

The number of cells used in these experiments varied from $10^5$, $2\times10^5$, $4\times10^5$, $5\times10^5$, and up to $10^6$ per hemisphere/striatum. The time of administering MSCs transplantation varied significantly across the studies with the time being 1-3 days, 2-4 weeks, and 8 weeks. These cells were found in the brain after direct grafting, but direct intrabrain delivery is a highly invasive and risky procedure. Thus these studies have not demonstrated that minimally invasion methods of administering stem cell therapy, such as systemic administration by IV injection, could be used.

All but one of the studies used the cells at passages no higher than 10. The exclude study used mouse umbilical cord blood-derived (mUBC-derived) MSCs at passages 40 and 50. Interestingly, the study observed that expression of marker of pluripotent stem cells, such as stage specific embryonic antigen-4 (SSEA4) increased with passaging and that transplantation of high-passage mUCB-derived MSCs confer significant motor benefits unlike transplantation with low-passage mUCB-derived MSCs. Unfortunately, potential pluripotent origin and high risk of karyotype mutation due to higher passage numbers put clinical applications at risk.

In contrast to these studies, the present invention provides a method of treating neurological diseases and condition that uses a unique population of IDPSC having the immunophenotype typical for MSCs as defined by the International Society for Cellular Therapy effective even with a minimally invasive administration, for example through classic IV route of delivery.

As demonstrated by these previous studies on treating HD with supposed MSCs, one hope for treating neurodegenerative diseases is using stem cells. Unfortunately, only treatment with administering fetal donor tissue to the striatum proceeded to clinical trial, and it was only a small trial.

Cell therapies in HD are intended to protect neuronal populations susceptible to disease and/or replace dysfunctional or dying neurons. Thus clinical progress in HD cell therapy has been centered on establishing protocols for transplanting fetal-derived cells into the diseased striatum. This strategy is helping the development for stem cell therapy in the clinic and provides a period of several years of improvements and stability, but not permanent cure for disease (Bachoud-Levi et al., 2006). The long-term follow up over a 3- to 10-year postoperative period of the patients concludes that fetal striatal allografting in HD is safe. However, no sustained functional benefit was seen, perhaps due to the small amount of cells that was grafted in this safety study compared with other reports of more successful transplants in patients with HD (Barker et al., 2013).

Use of stem cells therapies is inevitable since intracellular and cellular mechanisms are involved into HD phenotype. Stem cell therapy may also accelerate the process of brain tissue regeneration. Stem cells are an important therapy, which will help to rebuild an area of the brain that was most damaged in HD. Only drugs approach will not be able to reconstruct damaged brain areas especially in late stages of HD.

MSCs may be obtained from extracted human teeth, both permanent and deciduous, by enzymatic digestion (Gronthos et al. 2000; Miura et al., 2003), or by organ culture followed by explant (immature dental pulp stem cells, IDPSCs) technology as disclosed in International Application no. PCT/IB14/59850 and U.S. patent application Ser. No. 14/214,016. The IDPSCs are obtained from dental pulp tissue, which anatomically originated from ectomesenchymal tissue, more precisely from neural crest, which is a mass of tissue present in the early formation of an embryo. It eventually forms the hard and soft tissues of the neck and cranium.

IDPSCs, which are of neural crest origin, are known to migrate pre-natally into various, mainly ectodermal tissues and have the capacity to self-renewal and display a developmental potential almost the same as embryonic stem (ES) cells, but without risk of formation of embryonic bodies in vitro and teratomas in vivo (Kerkis and Caplan, 2012). The postmigratory stem cells of neural crest origin generate all craniofacial bones, the majority of cells and tissues of the central and peripheral nervous systems, as well as several non-neural cell types, such as smooth muscle cells of the cardiovascular system, pigment cells in the skin, cartilage, connective tissue, corneal epithelium and dental pulp among them. Although postmigratory postnatal stem cells of neural crest origin are of restricted developmental potential, they maintain functional characteristics resembling their embryonic counterparts and an ability to differentiate into a broad spectrum of cell types (Le Douarin et al., 2004, 2007, 2008; Dupin et al., 2007; Le Douarin & Dupin, 2003, 2012).

In vitro IDPSCs undergo uniform differentiation into neurons and glial cells. In vivo transplantation of human IDPSCs showed dense engraftment in various tissues, including neurons. Neuronal fate differentiation is based upon epigenetic "memory" of orofacial bones, including dental pulp, compared with those in axial and appendicular bone (bone marrow and ileac crest) based on their different embryological origins. Maxillas, mandible, including the alveolar bone (i.e. dentine, dental pulp and periodontal ligament), are formed exclusively by neural crest cells while axial and appendicular bones develop from mesoderm. Thus IDPSCs have the potential for neural regeneration and neuroprotection.

Logan A et al. described that multiple NTFs (neurotrophic factors) should be produced by cells in order to result in synergistic effect on neuroprotection. Therefore it is important that hIDPSCs cells are expressing and releasing multiple NTFs. Recent publications report the evidence for a paracrine mechanism of dental pulp stem cells (DPSC) action in neural support, with the gene expression of many NTFs, such as NGF (nerve growth factor), BDNF and NT3, the results demonstrated that hIDPSC promoted significantly more neuroprotection and neurogenesis of axotomised RGC than either hBMSC (bone marrow derived MSC) or hAMSC (adipose tissue derived MSC) (Mead B et al. 2013; Mead B et al., 2014; Martens W et al., 2013). Intravitreally transplanted DPSCs were suggested as a more appropriate cell type than BMSCs for retinal therapy (Mead B et al., 2014). These studies used DPSC (=SHED) enzymatically derived from adult rats using trypsin.

In addition, it has recently been strengthened by the results of an study using a rodent model of spinal cord injury with transplantation of SHED by direct dura transplantation in proximity and directly to the lesion site, wherein SHED was superior to three human skin fibroblast lines in terms of neuroprotection and neuroregeneration through both cell-autonomous and paracrine neuroregenerative activities (Sakai et al., 2012). These studies used cultured DPSC enzymatically derived from immature and adult wisdom using collagenase. During transplantation of DPSCs, animals were also treated with cyclosporine for immunosuppression.

Safety of Systemically Administering Stem Cells

Unless the transplant is an autograft, there is always a risk that the host's immune system will attack the transplant. Even a well-matched allograft requires immunosuppression pretreatment. This remains true for stem cell transplantation.

In order to avoid the host's immune system attacking the transplanted cells, the therapeutic stem cell population should be not be immunogenic. Immunogenicity is the ability of allogeneic stem cells to provoke an immune response when facing the host immune system after transplantation (Schu S et al., 2012). The transplantation of NPCs with mismatched major histocompatibility complex (MHC) into mice with mouse hepatitis virus-induced CNS demyelination resulted in increased T cell infiltration and NPC rejection (Weinger J G et al., 2012). However, recent evidence supports the possibility that undifferentiated adult stem cells are endowed with an immunologically privileged status and are capable of escaping the normal processes of allogeneic rejection (Bifari F et al. 2010). Immunologically privileged status is possible for a population of cells if the cells lack the expression of MHCs. For example, no immunogenicity in humans can occur by the population of stem cells being essentially negative for human leukocyte antigen (HLA), which is the human version of MHC. Therefore, the absence of HLA-DR, which is a quality control characteristic of IDPSCs (see Example 1), is an essential marker for cell to be used in for systemic cell therapy without need of toxic immunosuppression pre-treatment to the patient.

Another risk of stem cell transplantation is the increased risk of tumor development, especially for undifferentiated cells, because of these cell's potential for differentiation into other cell types. Pluripotent stem cells, especially hESCs and iPSCs cells are able to form spheres that resemble embryoid bodies in vitro and teratomas in vivo. All currently available technologies to apply pluripotent cells hold tumorigenicity risk. Expression and lack of expression of certain genes reduces risks to enable systemic administration of a population of stem cells.

Nanog is transcription factor associated with the maintenance of the pluripotent cells of the inner cell mass and the formation of embryonic stem cells. Nanog is a leukemia inhibitory factor (LIF) and activator of transcription-independent factor-3 (STAT-3). It is regulated by OCT4 and SOX2 and in turn positively regulates the expression of OCT4, SOX2 and itself by binding to the respective promoter gene regions (Boyer et al, 2005; Loh et al., 2006; Li, 2010). Together, these three transcription factors play an essential role in preventing differentiation of pluripotent stem cells (Boyer et al., 2005). The transfection cellular nucleus with OCT3/4, SOX2, NANOG was previously to be sufficient for inducing pluripotency in adult somatic cells (the creation of iPSC) and then lead to full pattern of embryonic stem cells theoretical characteristics: differentiation into 200 types of cells in the body, unlimited expansion, renewal potential, embryonic body formation, teratoma formation. Teratoma formation is a main threat of safety in cellular therapy. However, absence expression of nanog in nucleus is an essential safety marker to determine whether a population of stem cell is suitable for systemic administration. The lack of tumorigenicity of undifferentiated stem cells in vivo requires the absence of nanog in nucleus. Thus undifferentiated stem cells expressing inactive nanog, i.e. nanog localized in the cytoplasm, also lack tumorigenicity in vivo.

Another important safety marker for a population of stem cells suitable for systemic administration is the expression of p53. This protein is crucial in multicellular organisms, where it regulates the cell cycle and thus prevents cancer by functioning as a tumor suppressor.

ABCG2 protein expression is also safety marker that indicates a population of stem cells is suitable for systemic administration. ATP-binding cassette (ABC), ABCG2 protein (BCRP) expression is an important determinant of the MSC undifferentiated population phenotype. ABCG2 might serve as a marker for undifferentiated stem cells from various sources, as its expression is sharply downregulated with differentiation. Notably, ABCG2 transporters with Alzheimer's disease (AD), actively transport AP as confirmed histopathologically in AD cases and controls. Genome-wide association studies (Bertram L et al., 2007) have implicated a have identified genes the modulate AD risk, including genetic variants in ABCA7, a variant of ABC gene. It was concluded that increase in ABCA7 expression reduces AD risk, though increased ABCA7 expression during AD is insufficient to block disease progression (Jared B et al., 2014).

Thus some embodiments of the pharmaceutical composition of the invention comprises stem cells from tissue of neural crest origin expressing at least one safety markers selected from the group consisting of ATP-binding cassette sub-family G member 2 (ABCG2), inactive nanog, p53, and SOX2. In some aspects, the at least one safety marker is elected from the group consisting of ATP-binding cassette sub-family G member 2 (ABCG2), inactive nanog, and p53. The IDPSC have high expression of ABCG2 and p53 but low expression of inactive nanog and SOX2. For example, when the at least one safety marker is ABCG2 or p53, at least 75%, 80%, 85%, 90%, 95% or 98% of the stem cells of the pharmaceutical composition express the at least one safety marker. On the other hand, if the at least one safety marker is inactive nanog or SOX2, no more than 30%, 25%, 20%, 15%, 10%, 5%, or 5% of the stem cells express the at least one safety marker. In some aspects, the stem cells of the pharmaceutical composition coexpress ABCG3, p53, inactive nanog, and SOX2, wherein at least 75% of the stem cells express ABCG2, at least 75% of the stem cells express p53, no more than 5% of the stem cells express inactive nanog, and no more than 30% of the stem cells express SOX2.

Another embodiment of the pharmaceutical composition comprises stem cells from tissue of neural crest origin expressing at least one neuroepithelial stem cell marker selected from the group consisting of brain-derived neurotrophic factor (BDNF), neutrotrophin-3 (NT3), neutrotrophin-4 (NT4), neutrotrophin-5 (NT5), and p75. In some aspects, the stem cells have high expression of the at least one neuroepithelial stem cell marker. For example, at least 75%, 80%, 85%, or 90% of the cells express at least one neuroepithelial stem cell marker. In some embodiments, the stem cells of the pharmaceutical composition coexpress BDNF, NT3, NT4, NT5, and p75.

In some aspects, these embodiments pharmaceutical composition comprise stem cells from tissue of neural crest origin that are negative for HLA-DR. The stem cells of the pharmaceutical composition may also be negative for certain MSC markers selected from the group consisting of c-Myc, KU-4, and REX-1. In preferred embodiments, the stem cells of the pharmaceutical composition are negative for HLA-DR, c-Myc, KU-4, and REX-1.

The various embodiments of the pharmaceutical composition may also be combined. For example, the pharmaceutical composition may comprise stem cells from tissue of neural crest origin expressing at least one safety markers selected ABCG2, inactive nanog, and p53 and further express at least one neuroepithelial stem cell marker selected from the group consisting of BDNF, NT3, NT4, NT5, and p75. As another example, the pharmaceutical may comprise stem cells from tissue of neural crest origin expressing express at least one neuroepithelial stem cell marker selected from the group consisting of BDNF, NT3, NT4, NT5, and p75 while further expressing at least one safety markers selected ABCG2, inactive nanog, p53 and SOX2.

Methods of Using the Pharmaceutical Compositions

The present invention provides for methods for treating neurological diseases and conditions comprising systemically administering the pharmaceutical composition of the invention to a subject. In some implementations, these methods of treating neurological diseases and condition promote neurogenesis and are protective in models of neurodegenerative diseases. In some embodiments, systemic administration the population of stem cells, such as by IV administration, results in direct delivery of the cells to the brain. In some aspects, neurogenesis occurs by the population of stem cells self-differentiating and/or activating intrinsic stem cells to migrate and differentiate. In some aspects, neurogenesis is preferably dopamine-associated.

In some embodiments of the methods, the neurological disease or condition is treated by the stem cells crossing the blood/brain barrier (BBB) and inducing neurogenesis. In some aspects, the stem cells are directly transplanted into the brain parenchyma, including striatum, following crossing of the BBB. In some embodiments, the induced neurogenesis is dopamine-associated. For example, dopamine-associated neurogenesis occurs through self-differentiation of the stem cells or activation of migration and differentiation of intrinsic stem cells by the extrinsic stem cells. In some aspects, massive dopamine-associated neurogenesis takes place in the subventricular zone (SVZ).

In some implementations, the methods further comprise measuring the amount of DA receptor in the subject. In some embodiments, measuring the amount of DA receptor in the subject comprises imaging the subject to detect DA receptor. In most preferred embodiments of the methods, neurogenesis is mediated by dopamine receptor D2, thus in some embodiments, the DA receptor measured is receptor D2.

In some embodiments of the methods, the pharmaceutical composition provides neuroprotection. For example, systemic neuroprotection is provided with the high basal level of neurotrophic and immunoprotective factors expression and release pattern of the stem cells of the pharmaceutical composition. In some aspects, these stem cells of the pharmaceutical composition are IDPSCs.

The neurological diseases and conditions include, for example, autism, schizophrenia, epilepsy, stroke and ischemia, a neurodegenerative disease or condition, a motor disorder, or a convulsive disorder. The neurodegenerative disease or condition may be, for example, Parkinson's disease, multiple sclerosis, amyotrophic lateral sclerosis (ALS), stroke, autoimmune encephalomyelitis, diabetic neuropathy, glaucomatous neuropathy, Alzheimer's disease, and Huntingdon's disease. Motor disorders include, for example, Tourette syndrome, amyotrophic lateral sclerosis (ALS), progressive bulbar palsy, spinal muscular atrophy (SMA), post-polio syndrome (PPS). Convulsive disorders include, for example, epilepsy.

In some implementations, the methods for treating neurological diseases and conditions support the natural neuroprotective mechanism in subjects diagnosed with early HD. In other implementations, the methods for treating neurological diseases and conditions repairs lost DA neurons in subjects diagnosed with PD.

The present invention also provides for methods of using the pharmaceutical composition as a preventive therapy for subjects at risk of HD.

In one embodiment, the present invention is directed to a pharmaceutical composition for systemic administration to a subject to treat a neurological condition comprising undifferentiated stem cells from tissue of neural crest origin expressing at least one safety markers selected from the group consisting of ATP-binding cassette sub-family G member 2 (ABCG2), inactive nanog, and p53. In certain aspects, inactive nanog is expressed nanog localizing predominantly in the cytoplasma of the undifferentiated stem cell. In another aspect, at least 75% of the undifferentiated stem cells express the at least one marker when the at least one marker is ABCG2 or p53. In yet another aspect, no more than 5% of the undifferentiated stem cells express the at least one marker when the at least one biomarker is nanog.

In some embodiments, the undifferentiated stem cells express ABCG2, inactive nanog, and p53. In one aspect, at least least 75% of the undifferentiated stem cells express ABCG2, at least least 75% of the undifferentiated stem cells express p53, and no more than 5% of the undifferentiated stem cells express inactive nanog. In another aspect, the undifferentiated stem cells further express SOX2, and wherein no more than 30% of the undifferentiated stem cells express SOX2. In yet another aspect, the undifferentiated stem cells further express at least one neuroepithelial stem cell marker selected from the group consisting of brain-derived neurotrophic factor (BDNF), neutrotrophin-3 (NT3), neutrotrophin-4 (NT4), neutrotrophin-5 (NT5), and p75.

In other embodiments, the undifferentiated stem cells express BDNF, NT3, NT4, NT5, and p75. In one embodiment, the present invention is directed to a pharmaceutical composition for systemic administration to a subject to treat a neurological condition comprising undifferentiated stem cells from tissue of neural crest origin at least one neuroepithelial stem cell marker selected from the group consisting of BDNF, NT3, NT4, NT5, and p75.

In certain aspects, the undifferentiated stem cells express BDNF, NT3, NT4, NT5, and p75. In other aspects, the undifferentiated stem cells further express at least one safety markers selected from the group consisting of ABCG2, inactive nanog, p53, and SOX2. In certain aspects, inactive nanog is expressed nanog localizing predominantly in the cytoplasma of the undifferentiated stem cell.

In yet other embodiments, at least 75% of the undifferentiated stem cells express the at least one marker when the at least one marker is ABCG2 or p53. In certain aspects, the undifferentiated stem cells are negative for HLA-DR. In one embodiment, the tissue of neural crest origin is dental pulp. In yet other aspects, the undifferentiated stem cells from tissue of neural crest origin are immature dental pulp stem cells (IDPSCs).

In another aspect, the present invention provides a method of treating a neurological disease or condition comprising systemically administering to a subject a pharmaceutical composition comprising undifferentiated stem cells from tissue of neural crest origin expressing at least one safety marker selected from the group consisting of ABCG2, inactive nestin, and p53. In some aspects, the undifferentiated stem cells of the pharmaceutical composition further express at least one neuroepithelial stem cell marker selected from the group consisting of BDNF, NT3, NT4, NT5, and p75.

In yet another embodiment, the present invention is directed to a method of treating a neurological disease or condition comprising systemically administering to a subject a pharmaceutical composition comprising undifferentiated stem cells from tissue of neural crest origin expressing at least one neuroepithelial stem cell marker selected from the group consisting of BDNF, NT3, NT4, NT5, and p75.

In certain embodiments, the undifferentiated stem cells of the pharmaceutical composition further express at least one safety marker selected from the group consisting of ABCG2, inactive nestin, p53, and SOX2.

In other aspects, the subject is intravenously administered the pharmaceutical composition. In some embodiments, the neurological disease or condition is treated by the population of undifferentiated stem cells crossing the blood/brain barrier and inducing neurogenesis. In one aspect, the neurological disease or condition is treated by the undifferentiated stem cells inducing neurogenesis via dopamine-associated neurogenesis. In another aspect, the dopamine-associated neurogenesis is through self-differentiation of the undifferentiated stem cells or activation of migration and differentiation of intrinsic stem cells by the undifferentiated stem cells.

In certain embodiments, the undifferentiated stem cells of the pharmaceutical composition provide neurotrophic factors and immunoprotective factors. In other embodiments, the undifferentiated stem cells of the pharmaceutical composition provides systemic neuroprotection. In one embodiment, the undifferentiated stem cells are autologous and/or allogeneic to the subject.

In certain aspects, the neurological disease or condition is a neurodegenerative disease or condition. The neurodegenerative disease or condition may be selected from the group consisting of Parkinson's disease (PD), multiple sclerosis, amyotrophic lateral sclerosis (ALS), stroke, autoimmune encephalomyelitis, diabetic neuropathy, glaucomatous neuropathy, Alzheimer's disease, and Huntington's disease (HD).

In some aspects, the method comprises systemically administering the pharmaceutical composition to the subject, wherein the subject is diagnosed with early HD, supports the natural neuroprotective mechanism in the subject. In other aspects, the method comprises systemically administering the pharmaceutical composition to the subject, wherein the subject is diagnosed with PD, repairs lost dopaminergic neurons in the subject. In another embodiment, the neurological disease or condition is selected from the group consisting of autism, schizophrenia, stroke, and ischemia. In other embodiments, the neurological disease or condition is selected from the group consisting of a motor disorder and a convulsive disorder.

In certain aspects, the subject is administered a single administration of the pharmaceutical composition. In one embodiment, the subject is administered a single intravenous injection of the pharmaceutical composition. In yet other embodiments, the subject is administered a first and a second administration of the pharmaceutical composition.

In other embodiments, the subject is administered a first and a second intravenous injection of the pharmaceutical composition. In some aspects, the second administration or intravenous injection of the pharmaceutical composition takes place at least 7 days after the first administration or intravenous injection.

In one aspect, the method further comprises measuring the amount of DA receptor in the subject. In another aspect, the method comprises measuring the amount of DA receptor in the subject comprises imaging the subject to detect DA receptor. In one aspect, the DA receptor is receptor D2.

The present invention is further illustrated by the following examples that should not be construed as limiting. The contents of all references, patents, and published patent applications cited throughout this application, as well as the Figures, are incorporated herein by reference in their entirety for all purposes.

EXAMPLES

Example 1

Batch Release Process for Industrial Scale-Up of Multiharvest Organ and Tissue Explant Culture of hIDPSC—CELLAVITA™ (Stem Cells) Product by Late Population Method Nomenclature CELLAVITA™ (stem cells) is the bulk material prior to final formulation. CELLAVITA™ (stem cells) is referred to as Drug Substance (DS). CELLAVITA™ (stem cells) for IV infusion is referred to as Drug Product (DP). The Process for the CELLAVITA™ (stem cells) Substance initiates at donor screening and testing and finishes prior to final formulation and cryopreservation of the cell stock. Preparation of the Drug Product involves formulation of the CELLAVITA™ (stem cells) substance with additional excipients.

General Properties

In one embodiment, CELLAVITA™ (stem cells) is a stem cell expressing neural crest/mesenchymal stem/progenitor cell markers, such as CD13, CD105 (Endoglin), CD73, CD29 (integrin b-1), CD44, and nestin (Kerkis et al., 2009; Kerkis et al., 2006) obtained using multiharvest orgão and tissue explant culture.

In another embodiment, CELLAVITA™ (stem cells) are MSC-like cells, which possess all basic properties of these cells. The cells are defined in accordance with minimal criteria for defining multipotent mesenchymal stromal cells established by the Mesenchymal and Tissue Stem Cell Committee of the International Society for Cellular Therapy. This definition includes being plastic-adherent when maintained in standard culture conditions, expressing CD105, CD73 and CD90, and lack expression of CD45, CD34, CD14 or CD11b, CD79alpha or CD19 and HLA-DR surface molecules, and ability to differentiate to osteoblasts, adipocytes and chondroblasts in vitro (Dominici et al., 2006).

Manufacturing Method of Investigational Product CELLAVITA™ (Stem Cells)

Only healthy teeth of children aged 6-12 years will be used for the cultivation of Cellavita™. Children's legal guardians will answer an eligibility questionnaire about the child's health and blood samples will be collected for serological testing to detect infectious diseases, as recommended by the European Commission guidelines for donor eligibility (COMMISSION DIRECTIVE 2006/17/EC). The mandatory testing includes tests for HIV-1 and -2 (Anti-HIV-1 and -2), HTLV-1 and -2, HBV (specifically HBsAg, Anti-HBc), HCV (specifically anti-HCV-Ab), and Treponema pallidum (syphilis) (COMMISSION DIRECTIVE 2006/17/EC).

Only healthy teeth without dental diseases such as dental caries will be collected after natural loss or surgical extraction. To avoid unnecessary testing, only donors whose teeth have viable pulp for cultivation (a process determined in the laboratory after two weeks of cell culture) will be asked to return to the center for the donor eligibility test (blood collection).

Tooth Collection, Container, Transportation

Immediately after spontaneous exfoliation, the tooth will be immersed into 3 mL of sterile transporting solution composed of DMEM (Dulbecco's Modified Eagle Medium) and 500 mM Gentamycin in a 15 mL sterile centrifuge tube. The tooth will be stored at 4° C. and processed within 48-72 hours.

Pulp Isolation and Washing Procedure

A freshly exfoliated deciduous tooth from a healthy subject will be washed repeatedly in sterile solution containing 50% pen/strep solution (100 units/mL penicillin, 100 units/mL streptomycin) and 50% Phosphate Buffered Saline (PBS). Dental pulp will be removed from the tooth with the aid of a sterile needle.

Selection of Viable Pulps as a Raw Material for hIDPSC Stem Cell Expansion

Freshly obtained dental pulp (DP) will be washed in a solution containing 3% Pen/strep solution (100 units/mL penicillin, 100 units/mL streptomycin). Initial plating and viability testing of the dental pulp will be performed in dental pulp Maintenance Medium supplemented with 15% fetal bovine serum (FBS, Hyclone), 100 units/mL penicillin, 100 units/mL streptomycin, 2 mM L-glutamine, and 2 mM nonessential amino acids. This procedure usually takes up to one week. Once the DP will be determined as viable it will be harvested and hIDPSC will be passaged. The resulting hIDPSC will be cryopreserved under GTP conditions for future clinical research Pharmaceutical Development A small scale, non-GMP batch of CELLAVITA™ (stem cells) was produced in Dr. Irina's lab for obtaining patent and generating nonclinical data. The technology was transferred to a semi-industrial, non-GMP facility in Israel (Sheba Hospital). The CMC content in this briefing document describes the manufacturing process in Israel, and is also representative of the plan to manufacture clinical batches in a GMP facility in Brazil, to where the technology will be transferred.

In one aspect, the production process comprises the steps illustrated in FIG. 1 which demonstrates the initial process of CELLAVITA™ (stem cells) isolation and batch formulation. The vertical pathway shows the process of dental pulp mechanical transfer (harvest) of early population-hIDPSC (isolated from dental pulp before 5 harvests) and late population—hIDPSC (isolated from dental pulp after 5 harvests). The horizontal pathway shows the traditional enzymatic method of cell cultures when cells are replaced through repetitive passages. The final batch product is a sum of hIDPSC obtained from dental pulp harvests and passages (no more then 5).

Figure 2:
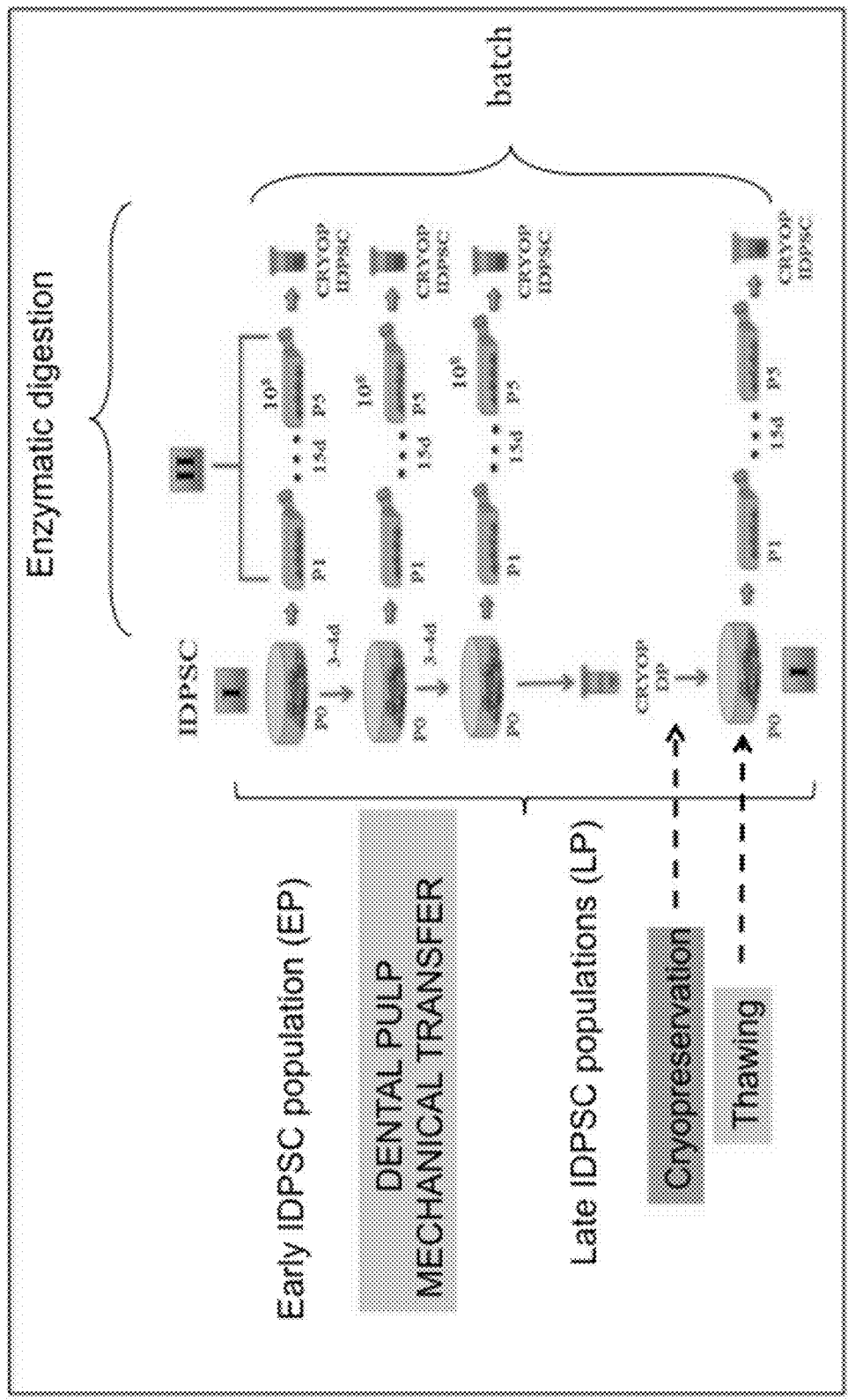
FIG. 2 depicts an early phase development process for CELLAVITA™ (stem cells) isolation and batch formulation.
Figure 3:
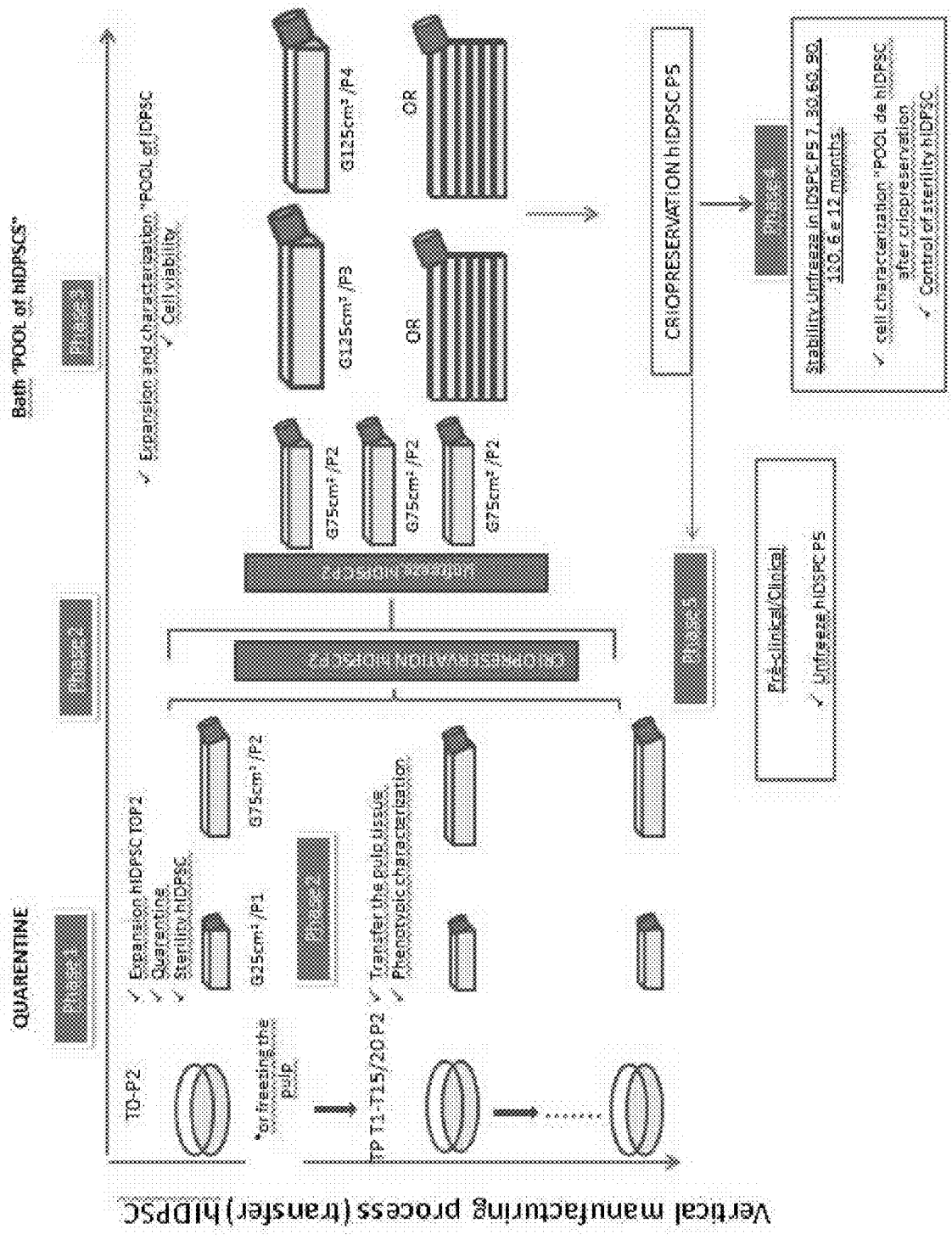
FIG. 3 depicts another early phase development manufacturing process for CELLAVITA™ (stem cells).

In another aspect, the production process comprises the steps illustrated in FIG. 2 and/or FIG. 3. The production process includes CELLAVITA™ (stem cells) isolation and batch formation. The vertical pathway shows the process of dental pulp (DP) mechanical transfer (harvest) for early population-hIDPSC isolated from dental pulp before 5 harvests and late population—hIDPSC isolated from DP after 5 DP harvests; the horizontal pathway shows traditional enzymatic method of cells culturing, when cells are replaced through repetitive passages. Final batch—product is a sum of hIDPSC obtained from DP harvest and passages (no more then 5).

Description of the Proposed Manufacturing Process Controls for the Clinic

Figure 4:
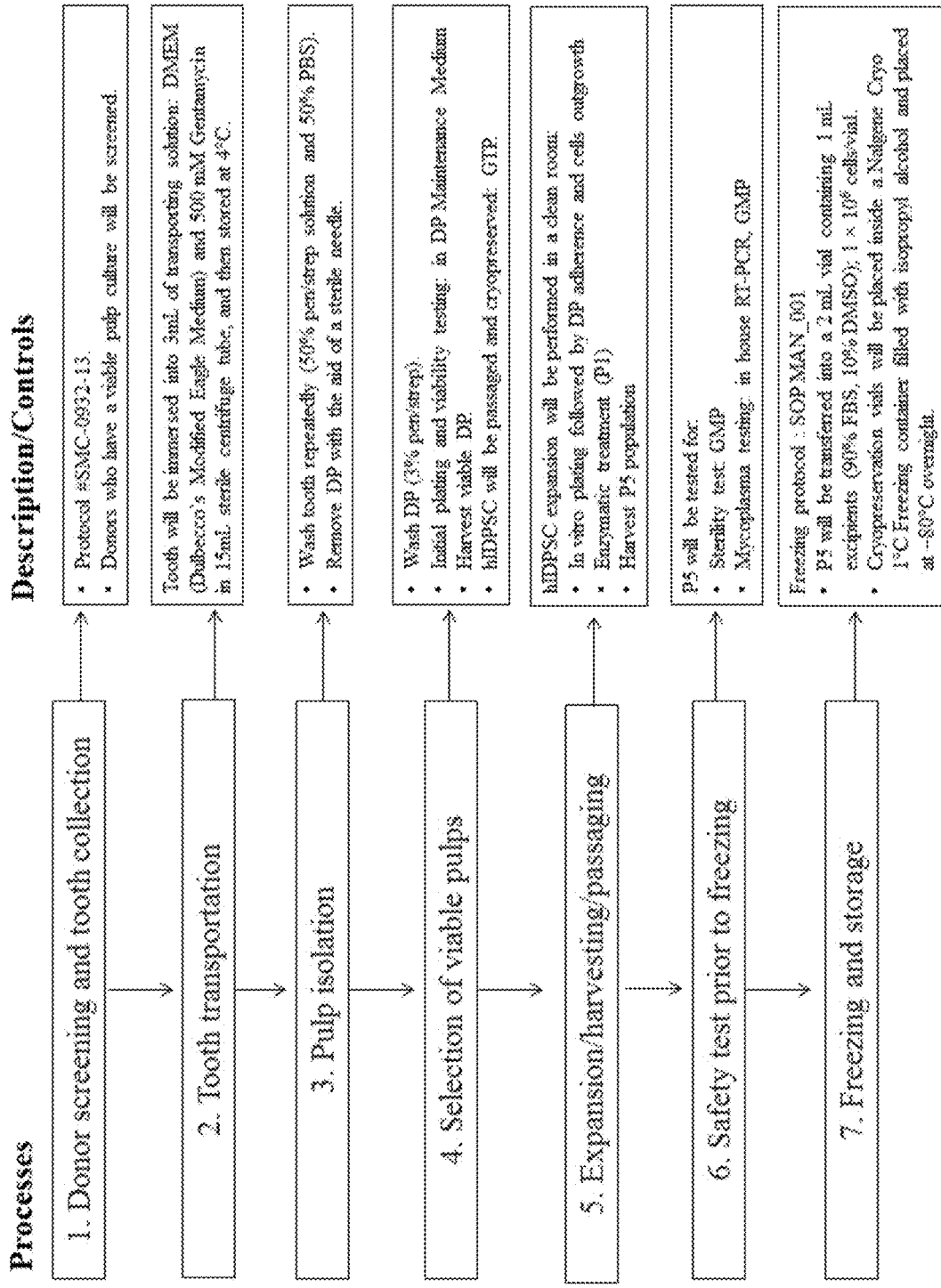
FIG. 4 depicts a CELLAVITA™ (stem cells) production process composed of several major steps.

The production of CELLAVITA™ (stem cells) will be performed in a state of the art clean room facility and the process will be performed according to GMP regulations. In one embodiment, this production process follows the steps outlined in FIG. 4.

hIDPSC Harvesting

When the semi-confluent colony formation of hIDPSC will be detected around the dental pulp explant, DP will be transferred into a new cell culture vessel for continued growth in DP Maintenance Medium.

hIDPSC Passaging hIDPSC will be washed with sterile PBS, removed with TrypLE solution and centrifuged. The pellet will be resuspended in DP Maintenance Medium and thereafter will be seeded in the tissue culture flask (Passage 1-P1). When the cells reach about 80% confluency they will be passed to the new flask (Passage 2-P2). Cells will be incubated in a humidified 5% CO2 incubator.

Safety Tests Prior to Freezing hIDPSC from P5 will be maintained in culture for at least 3-5 days in order to collect cell conditioned medium for sterility and mycoplasma testing.

Sterility test will be performed by ISO, GMP certified

Mycoplasma testing will be performed using an in-house RT-PCR test (EZ-PCR Biological Industries) and by ISO, GMP certified.

Freezing and Storage

The hIDPSC freezing protocol will be adapted to the standard freezing repository protocol hIDPSC from P5 will be transferred into a 2 mL cryopreservation vials containing 1 mL of freezing media, composed of: 90% FBS and 10% DMSO (GMP/US pharmaceutical grade). 1×106 cells per vial will be cryopreserved.

Cryopreservation vials will be placed inside a Nalgene Cryo loC Freezing Container filled with isopropyl alcohol and will be placed at −80° C. overnight. Thereafter, vials will be transferred to the vapor phase of a liquid nitrogen storage tank and their locations will be recorded.

Control of Materials

Table 1 depicts the process, which will be used for control of materials.

Tooth Collection, Container, Transportation

Immediately after spontaneous exfoliation, the tooth will be immersed into 3 mL of sterile transporting solution composed of DMEM (Dulbecco's Modified Eagle Medium) and 500 mM Gentamycin in a 15 mL sterile centrifuge tube. The tooth will be stored at 4° C. and processed within 48-72 hours in the GTP laboratory.

The hIDPSC freezing protocol will be adapted to the standard freezing repository protocol hIDPSC from P5 will be transferred into a 2 mL cryopreservation vials containing 1 mL of freezing media, composed of: 90% FBS and 10% DMSO (GMP/US pharmaceutical grade). 1×106 cells per vial will be cryopreserved.

Cryopreservation vials will be placed inside a Nalgene Cryo loC Freezing Container filled with isopropyl alcohol

TABLE 1

Control of Materials

| Reagent | Concentration at Use | Source/Country of Origin | Manufacturer | Manufacturing Step |
|---|---|---|---|---|
| Deciduous Tooth | 1 tooth | Brazil | NA | Raw material |
| Dulbecco Modified Eagle Medium-F12 (DMEM-F12) | 500 mL | Beit Haemek, Israel | Biological Industries (BI) | Transporting solution |
| Dulbecco's Phosphate Buffered Saline without Calcium and Magnesium (DPBS) | 500 mL | Beit Haemek, Israel | Biological Industries (BI) | Sterile solution |
| Gentamycin | 500 mM | Beit Haemek, Israel | Biological Industries (BI) | Sterile solution |
| Fetal Bovine Serum | 90% | Washington | HyClone | Maintenance medium; freezing media. |
| L-Glutamine Solution | 2 mM | Beit Haemek, Israel | Biological Industries (BI) | Maintenance medium |
| Penicillin-Streptomycin Solution | 100,000 U/mL penicillin and 100 mg/mL streptomycin | Beit Haemek, Israel | Biological Industries (BI) | Sterile solution |
| Non-essential amino acids | 2 mM | Beit Haemek, Israel | Biological Industries (BI) | Maintenance medium |
| TrypLE | 1X | | Gibco | Cell-dissociation enzymes |
| DMSO | 10% | | Sigma | Cryopreservation |

Tissue (Dental) Criteria

Spontaneously exfoliated deciduous teeth will be collected. Only healthy teeth without dental decay will be accepted. In order to prevent unnecessary donor testing, only donors which have a viable pulp culture (as determined by the study laboratory staff after initial plating and culture establishment, stages which take approximately two weeks) will be requested to make a second study visit in order to have blood samples drawn for donor eligibility screening. The Sponsor estimates that viable pulp cultures will be established from approximately 50% of recruited donors.

The parents/guardians of the subjects will answer a donor eligibility questionnaire concerning the health of their child. In addition, blood samples (total volume of 10 mL) will be drawn in order to test the donors for the following pathogens according to guidelines for eligibility screening:

HIV 1&2 (specifically Anti-HIV-1,2)

HTLV I & II

HBV (specifically HBsAg, Anti-HBc)

HCV (specifically Anti-HCV-Ab)

Treponema pallidum (syphilis)

The total amount of blood to be drawn for these tests will not exceed 0.8 mL/kg body weight for one blood draw.

and will be placed at −80° C. overnight. Thereafter, vials will be transferred to the vapor phase of a liquid nitrogen storage tank and their locations will be recorded.

Thawing and Administration of CELLAVITA™ (stem cells)

Prior to administration of CELLAVITA™ (stem cells) in patients, the cryopreserved product after thawing must be assessed for cell viability. This will be done with a kit that will be sent along with the CELLAVITA™ (stem cells). The kit and the method to be performed must be followed as described below.

Composition of Thawing Kit

Conical falcon tube containing 15 ml thawing substance;

Two conical 15 ml falcon tubes containing 5 ml PBS;

Six sterile Pasteur pipettes

Thawing Protocol

The CELLAVITA™ (stem cells) product should be thawed in a laminar flow system.

The Cryotubes containing CELLAVITA™ (stem cells) will be transferred to a bath of water at 37° C. (2-3minutos).

After thawing, the product of cryotubes must be removed with a sterile Pastuer pipette and immediately transferred to a 15 ml conical tube containing 5 ml defrosting substance. The solution should be thoroughly mixed slowly for 5 to 10 times with a Pasteur pipette. Centrifuge product for 5 minutes at 1000 rpm.

The supernatant should be discarded. The precipitated cells must be added to a Falcon tube with PBS solution. The cells are homogenized slowly for 5 to 10 times. Centrifuge the cells for 5 minutes at 1000 rpm. Repeat this procedure twice.

At the end of this procedure the cells are ready to be administered to the patient. Administration to the Patient For administration of CELLAVITA™ (stem cells) product, enough cells/kg body weight will be transferred to a bag of 250 ml of 0.9% saline. This solution will be infused intravenously (peripheral vein) over a period of 10 to 40 minutes.

Example 2

Batch Numbering System

Each donor IDPSC culture will be defined as a separate batch of raw material for future stem cell expansion process. hIDPSC will be individually coded and labeled, in an anonymous fashion. Cryotubes boxes will be double-packed to reduce risk of cross contamination, according to process.

The purpose of the batch definition is to ensure consistency and traceability. The following label will be attached to cryopreservation vial:

Lot Number of hIDPSC: _____
Number of Harvest: _____
Collection Date: _____
Freezing Date: _____

Example 3

Characterization of Early and Late Harvests IDPSCs and Derivation of Neural and Glial Cells from the Early and Late Harvest IDPSCs Characterization of Early and Late Harvests IDPSCs To characterize the properties of the hIDPSC, from the early (n=8) and late (n=4) harvests (Table 2), flow cytometric analyses for the mesenchymal markers CD13, CD105, CD73, CD90, CD44 was performed. FACS experiments were performed with $2\times10^5$ cells. Cells were washed twice with PBS (without calcium and magnesium) and the tested antibodies were added for 15 minutes at room temperature. The cells were then washed twice with cold PBS and analyzed with a Becton-Dickinson flow cytometer. The fluorescence of PE (FL2), FITC (FL1), APC (FL4) were detected in 575 nm, 53 nm, and 600 nm emission wavelengths, respectively.

TABLE 2

List of cells used in the FACS experiments

| Batch Number | Harvest Number (H) | Passage Number (P) |
|---|---|---|
| Early Harvests: | | |
| 1 | 0 | 3 |
| 6 | 0 | 3 |
| 10 | 0 | 3 |
| 11 | 0 | 3 |
| 17 | 0 | 3 |

TABLE 2-continued

List of cells used in the FACS experiments

| Batch Number | Harvest Number (H) | Passage Number (P) |
|---|---|---|
| 22 | 0 | 3 |
| 24 | 0 | 3 |
| 26 | 0 | 4 |
| Late Harvests: | | |
| 11 | 13 | 3 |
| 11 | 16 | 9 |
| 24 | 13 | 3 |
| 26 | 10 | 2 |

Cells from both early and late harvests expressed high levels of mesenchymal markers. Both populations were negative for HLA-DR and HLA-ABC antigen expression which allows for allogenic transplantation of these populations of cells. Both populations were double immunopositive for mesenchymal stem cell markers, such as, CD13 and CD44 and others, as well as expressed nestin, P75 (CD271), neuroepithelial stem cell markers, and nerve growth factor (NGF) (see FIGS. 5 and 6A-6L and Table 3) and they were negative for CD146 and HLA-ABC.

Figure 7:
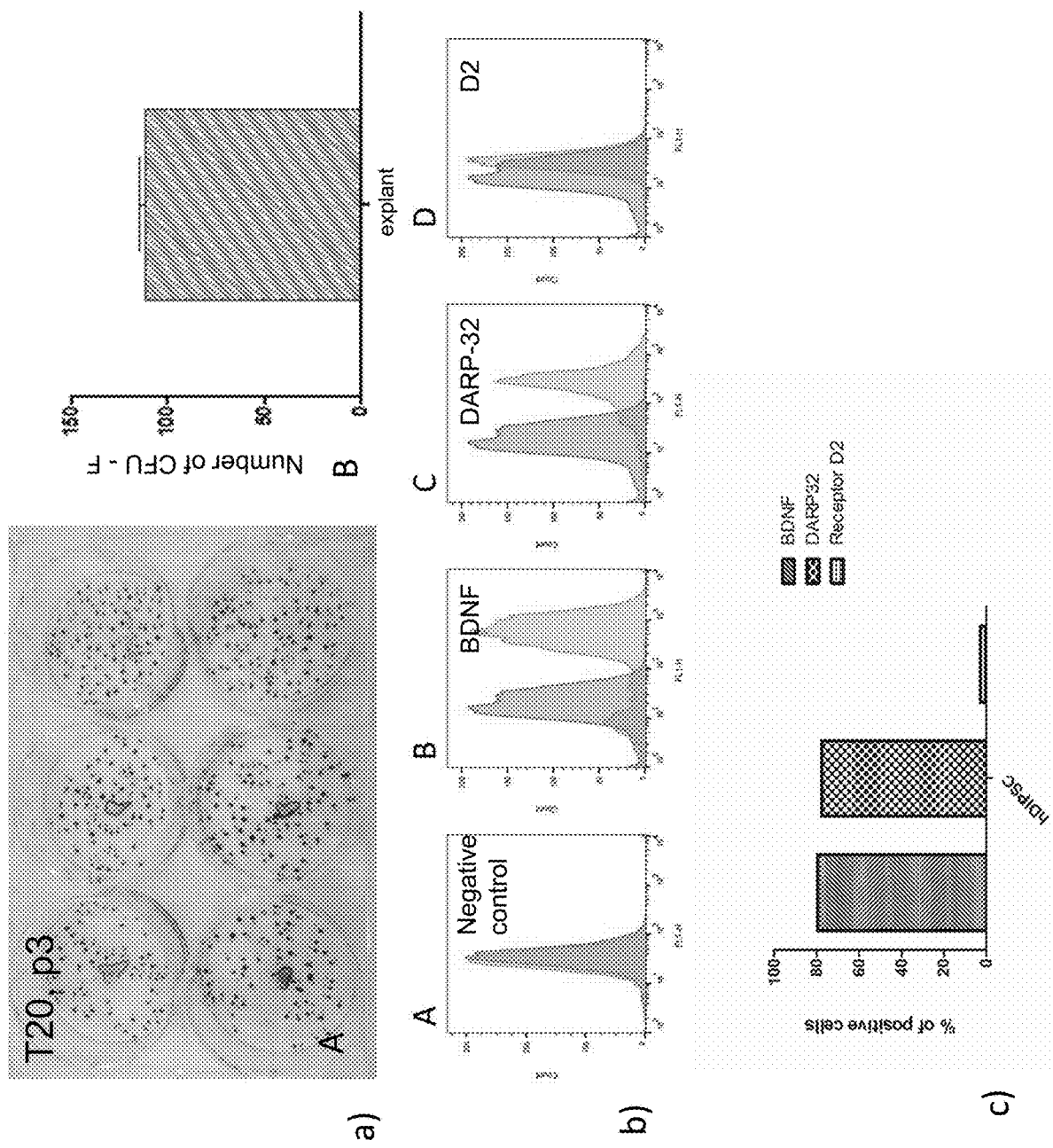
FIG. 7 depicts in a) CFU-F assay performed in triplicate at T20, passage 3, demonstrating high clonogenic capacity of a LP population of IDPSCs. In b) and c) FACS analysis performed to show that LP of IDPSCs (batch #11) comprise approximately 80% cells that express BDNF and DARP 32 while EP is negative for these markers (data not shown) and comprises a very low number of the cells which express D2.
Figure 8B:
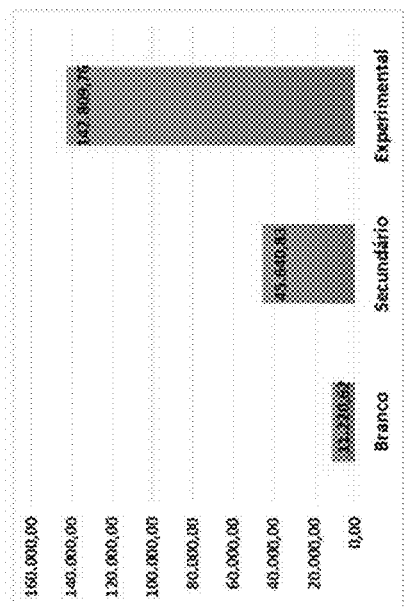
FIGS. 8B and 8C depict quantification of LP IDPSC which reacted positively with an BrdU antibody. (A)—Epi-fliorescence, (B) and (C)—FACS analysis. Magnification (A)—200×. (B, E and H)—400×. (C, F, I, D, G and J)—1000×.
Figure 8C:
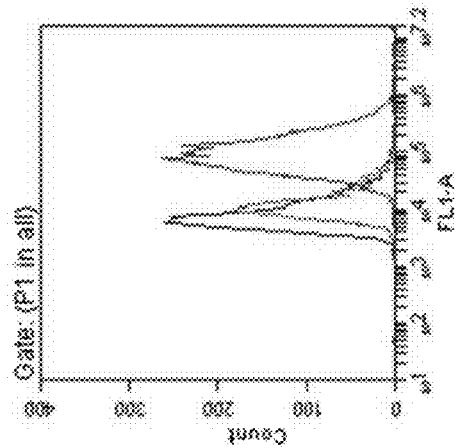
Figure 8A:
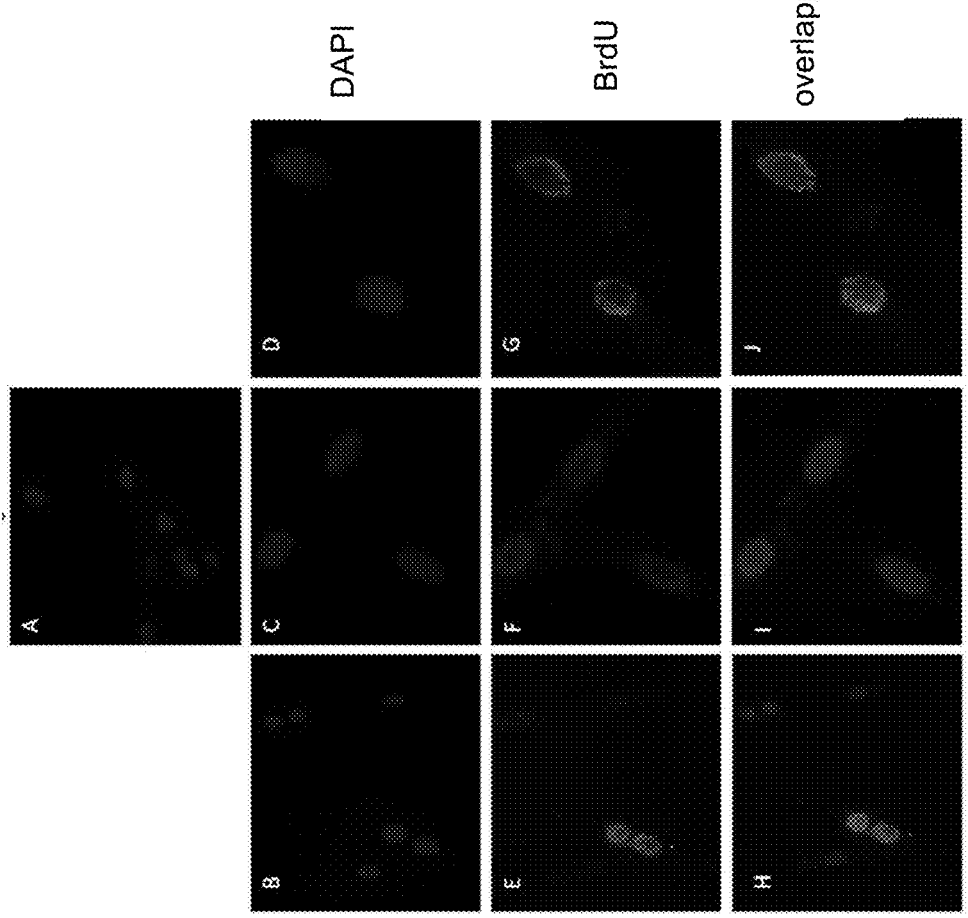
FIG. 8A depicts positive immunostaining for BrdU (B-J) in control cells with a secondary antibody.

After mutiharvest of DP tissue and explant culture, IDPSC demonstrate capacity to form colonies (FIG. 7). The colony forming assay (CFU-F) assay was performed in triplicate at T20, P3 using 480 cells seeded in each plate, at day 8 multiple colonies colonies appeared and approximately 100 colonies were formed in each plate (FIG. 7). Colony forming capacity is one of the principal characteristics of stem cell. Therefore, we conclude that this capacity was maintained when the cells were obtained using the disclosed multiharvest organ and tissue explant method. Additionally, the proliferative activity of LP IDPSC was evaluated as shown on FIG. 8, and these cells demonstrated a very high proliferative rate.

TABLE 3

Comparison of the cell marker expression from the hIDPSC derived from the same donor by FACS analysis.

| | % of Fluorescence | | |
|---|---|---|---|
| Markers | H0P3 | H13P3 | H16P9 |
| CD105 | 99.4 | 99.76 | 99.6 |
| CD13 | 99.5 | 99.1 | 99.3 |
| CD73 | 95.1 | 99.88 | 85.3 |
| CD90 | 99.9 | 99.9 | 99.7 |
| CD44 | 99.12 | 99.45 | 96.4 |
| HLA-DR | 0.8 | 3.03 | 0.4 |
| HLA-ABC | 0.2 | 0.1 | 0.3 |
| NGF | 18.7 | 55.96 | 49.5 |
| Nestin | 54.5 | 66.57 | 30 |
| ABCG2 | 1.88 | ND | 8.1 |
| ABCB1 | 24.8 | ND | 45.6 |

Table 3 compares the cell marker expression from the different harvests of hIDPSC derived from the same donor (i.e., H0P3=first harvest; H13P3=later harvest; H16P9=last harvest). Late harvest populations had greater levels of NGF than the early harvest population. Expression of adenosine triphosphate binding cassette (ABC) transporters was also tested in the cells. ABC transporters are involved in the active transport of an extremely diverse range of substrates across biological membranes. These transporters are commonly implicated in the development of multidrug resistance and are also involved in numerous physiological and homeostatic processes, including lipid transport, cell migration and differentiation. Moreover there is evidence that ABC transporters serve as phenotypic markers and functional regulators of stem cells (Bunting 2002). Both early and late harvests populations expressed ABCB1 protein, the product of MDR1 gene, but expression was higher in the late harvest. According to Islam et al. (2005), ABCB1 is expressed in human fetal neural stem/progenitor cells (hNSPCs).

FACS analysis show that LP of IDPSCs (batch #11) comprises approximately 80% cells that express BDNF and DARP 32, while EP is negative for these markers (data not shown) and very low number of the cells, which express D2 (FIG. 7). To further characterize hIDPSC early and late harvests, total brain-derived neurotrophic factor (BDNF) levels represented by the amount of BNDF in medium was determined using ELISA (Table 4). BDNF levels were quantified by using a human BDNF Quantikine ELISA kit according to the manufacturer's protocol (R&D Systems, Minneapolis, Minn.). Cells ($1 \times 10^6$) from different harvests were inoculated in 75 cm plastic flasks. The supernatants were harvested approximately 4 days after inoculation. The results were expressed as the BDNF concentration. BDNF was secreted in all cell subsets, but the levels were 4-10 folds higher in the late harvests.

TABLE 4

Total BDNF levels in early and late harvests of hIDPSC

| Batch number | Harvest (H) and Passage (P) Number | BDNF levels (pg/ml) |
| --- | --- | --- |
| 11 | H0 P3 | 13 |
| 24 | H10 P2 | 154 |
| 26 | H13 P3 | 43 |

Comparison with Other MSCs Shows that hIDPSCs Secrete Much More BDNF.

The average level of BDNF secreted by $1 \times 10^6$ hIDPSCs is 6589 pg, which is many times higher than other types of MSCs that secrete BNDF, such as the MSCs of Gothelf et al. in 2014 (Clin Transl Med. 2014 3:21). Gothelf et al. induced bone marrow-derived MSCs (BM-MSC) to differentiate into neurotrophic factor-secreting cells (BM-MSC-NTF) by incubating the BM-MSCs for 72 hours in medium containing 1 mM dibutyryl cyclic 15 AMP (cAMP), 20 ng/ml human Basic Fibroblast Growth Factor (hbFGF), 5 ng/ml human platelet derived growth factor (PDGF-AA), and 50 ng/ml human Heregulin β1. Although the induction medium nearly doubled BDNF secretion (827 pg BNDF/$10^6$ BM-MSC compared to 1640 pg BNDF/$10^6$ BM-MSC-NTF cells), hIDPSCs still secreted four times more BDNF than BM-MSC-NTF. Accordingly, the hIDSPCs have much greater neuroprotective potential than bone marrow-derived MSC induced to secrete neurotrophic factors.

Expression of Oct4, Nanog, Sox2 and p53

Figure 9:
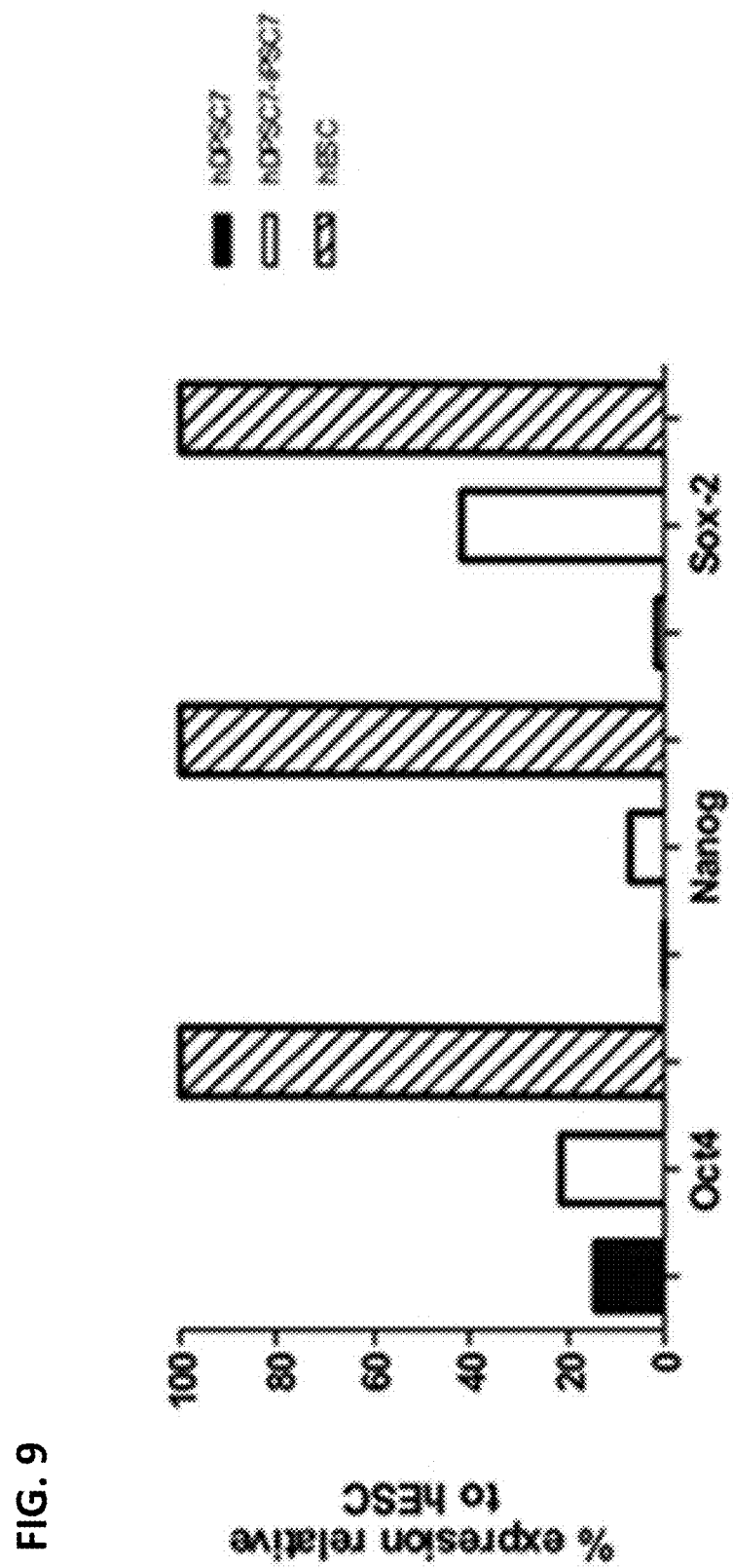
FIG. 9 depicts quantitative PCR for expression of endogenous Oct4, Nanog and Sox2 genes observed in hIDPSCs before (black color) and after reprogramming (white color) as well as in human embryonic stem cells (hESC) (striped).

It is known that MSCs generally express pluripotent markers such as Oct4, Nanog and Sox2 at low levels as described in the literature (Jiang et al., 2002; Guillot et al., 2007). We showed that hIDPSC express very low levels of such markers in comparison with human embryonic stem cells and even induced pluripotent stem cells obtained from hIDPSCs (see FIG. 9). More importantly, we demonstrated that hIDPSC express a high level of p53. The tumor suppressor gene p53 is well known as a master regulator that helps keeps cancer at bay. Blocking the p53 pathway vastly improves the ease and efficiency of transforming differentiated cells into induced pluripotent stem cells (Dolgin, 2009).

Derivation of Neural and Glial Cells from the Early and Late Harvests IDPSCs

The neuronal system consists of two classes of neural precursor cells: neuronal NPCs that differentiate into neurons and glial NPCs that differentiate into glia. Both neuronal and glial NPCs descend from the same neuroectodermal precursor. A third class of neural precursor cells, neuroglioblast, was also suggested. This third class of cells include radial glial cells also can act as neuronal precursors and only later, after neurogenesis, do they shift towards an exclusive generation of astrocytes.

The ability to distinguish whether a population of cells in cell therapy are neuronal NPSs or glial NPCs is of extreme importance for developing an efficient cell therapy strategy for treating neurodegenerative diseases, which mainly involve the damage or loss of both glia and neurons. It is possible to test known cell populations for the potential to differentiate into neurons or glia by inducing these cells to differentiate.

Figure 10:
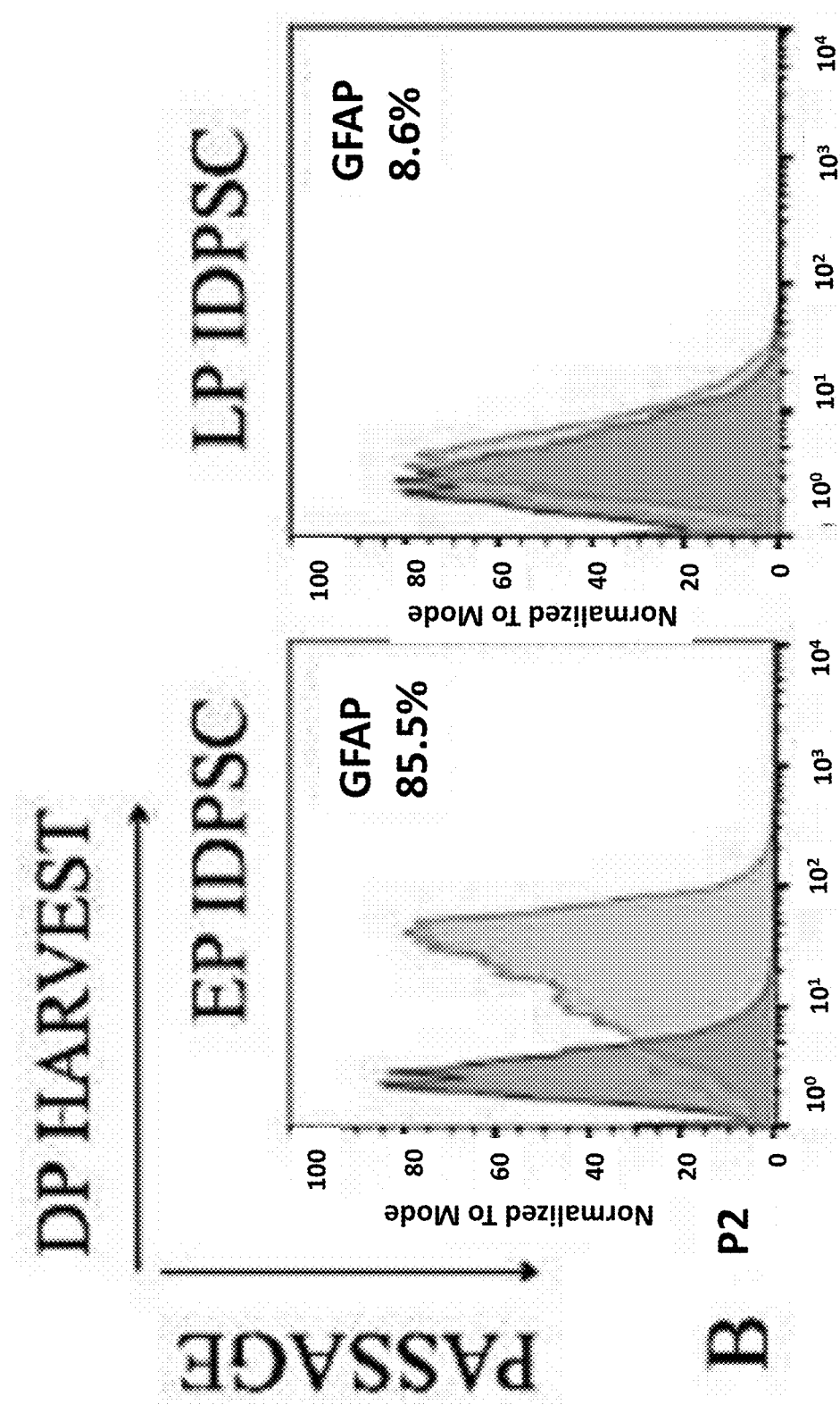
FIG. 10 depicts quantification of expression of GFAP (glial fibrillary acidic protein) and beta-III-tubulin in EP (early population) and LP (late population) IDPSC with flow cytometry.
Figure 10:
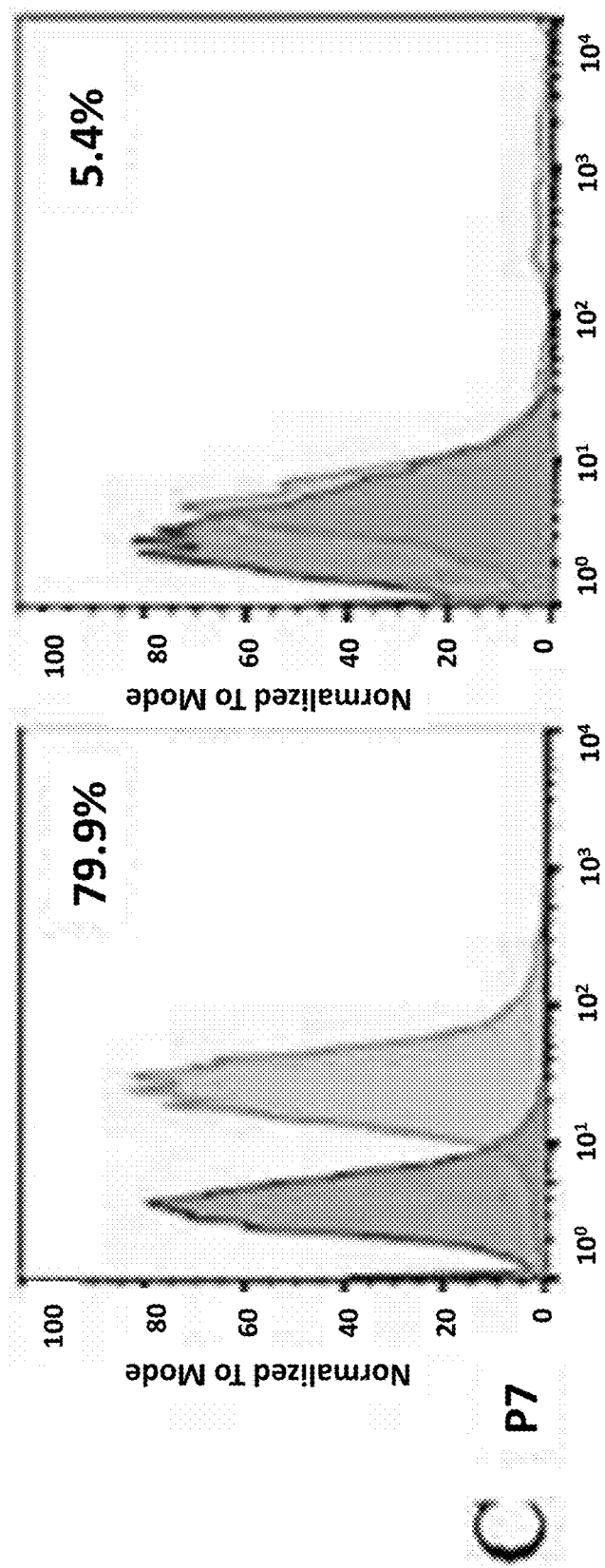
Figure 10:
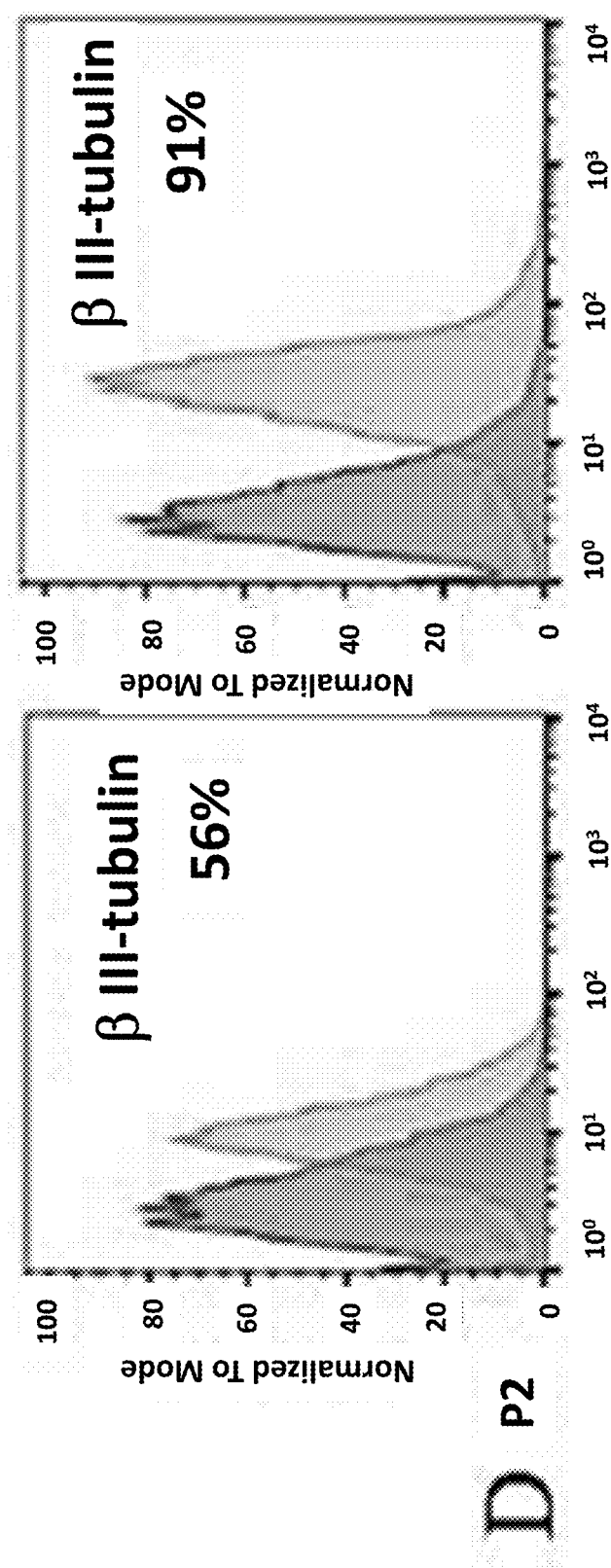
Figure 10:
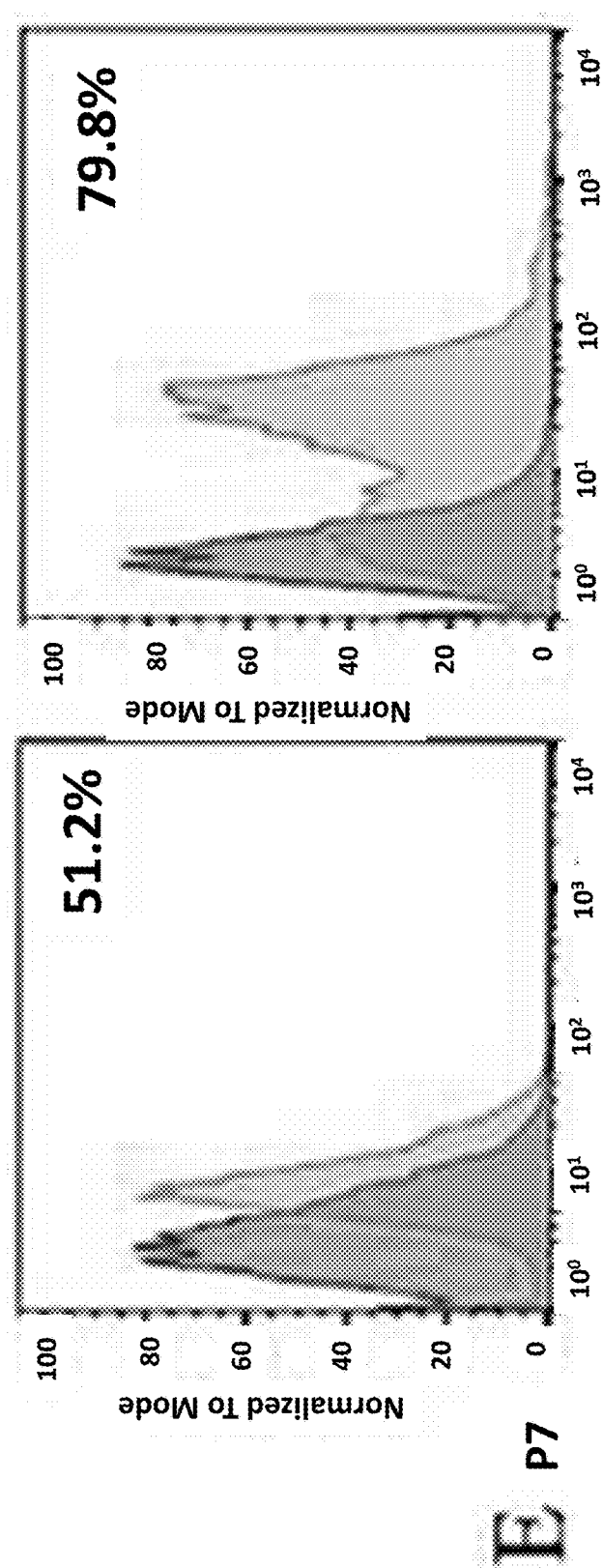

The capacity of EP (early population) and LP (late population) IDPSC to produce neurons and glias was tested by inducing neuronal differentiation in EP and LP IDPSC at early (P2) and late passages (P7) according to the previously described protocol (Kerkis et al., 2006) (FIG. 10). After 7 days, the cells were collected and analyzed by flow cytometry using GFAP (glial fibrillary acidic protein) and beta-III-tubulin antibodies, respectively. A significant difference exists in the number of cells that express these markers between EP (B-E, left) and LP (B-E, right), which were established following a dental pulp (DP) harvesting protocol. On the other hand, no significant difference in expression of both proteins was detected between different passages (P2 and P7) obtained following enzymatic digestion, (FIG. 10). Surprisingly, IDPSCs can be neuronal and glial NPCs. Early DP harvesting (EP IDPSC) leads to isolation of neural progenitor cells committed mainly to glial differentiation while late DP harvesting (LP IDPSC) leads to isolation of neural progenitor cells committed mainly to neuronal differentiation.

Thus DP harvesting is important for establishing a population of NPCs with the potential to develop into neurons and glia. SHED, which are stem cells from human deciduous teeth, cannot be categorized as an early population or late population because they are stem cells isolated from dental pulp cells without DP harvesting. The single SHED population contains neuron-committed and not glial-committed progenitors. In Miura et al. (2003) neuronal differentiation of SHED resulted in increased expression of beta-III-tubulin, GAD, and NeuN while the expression of nestin, GFAP, CNPase, and NFM remained the same after the induction of differentiation (see FIG. 4I of Miura).

Example 4

Comparison of IDPSC with SHED and with Other Therapeutic Stem Cells which Can Be Potentially Used for the Treatment of Neurological Conditions 1. Comparison of IDPSC and SHED MSCs from different sources (e.g. bone marrow and adipose tissue) can respond differently to various stimuli (Fraser J K et al., 2006). Culture conditions (e.g., media supplemented with either human serum or fetal calf serum (FCS), or serum-free) may also affect the differentiation potential of even MSCs of the same origin (Lindroos et al., 2011; Lizier et al., 2012). Different isolation and culture protocols used by different groups may account for the predominance of a particular MSC subpopulation with a distinct differentiation potential (Ho et al., 2008; Pevsner-Fischer et al., 2011; Rada et al., 2011).

SHED and IDPSCs have different methods of isolation and come from different stem cell niches. So it is unsurprising that SHED and IPSCs also have different expression of stem cell markers (see Table 5). SHED originated from a perivascular environment and STRO-1 and CD146 positive cells were found to be located around blood vessels of the remnant pulp by immunohistochemical staining. Only a minor proportion (9%) of ex vivo expanded SHED stained positive for the STRO-1 antibody using FACS.

derived spheres created by a combination of EGF and bFGF for 7 days in vitro) were transplanted into Parkinsonian rats. The cell suspension (200,000/µL) was injected into 2 DA-depleted striatum sites in rats (2.5 per site). Modest differentiation into DA neurons was observed (Wang et al, 2010). In a third study, SHED were injected in injured brain of postnatal day 5 mice, which were induced with in perinatal hypoxia-ischemia (HI) that has high rates of neurological deficits and mortality. Cyclosporine A was used to protect engrafted cells from the xenogeneic host immune response, nevertheless eight weeks after transplantation the engrafted SHED, had no or few cells differentiated into neurons, oligodendrocytes, or astrocytes (Yamagata et al. 2013).

The common theme across all three experiments is that SHED were administrated together with Cyclosporine A.

TABLE 5

Differences between SHED and IDPSCs

| SHED | IDPSC |
|---|---|
| Perivascular niche | Perivascular niche |
| | Nerve plexus |
| | Subodontoblastic plexus niche |
| | Cell-free and cell-rich zones |
| whole dental pulp (DP) | minced pulp |
| Enzymatic digestion: 1 hour | Organ culture, explant method, stem cell migration from stem cell niches |
| Can be isolated one time from the same DP, which is descarted after enzymatic digestion | DP is preserved and in vitro transferrable up to 60 times to result in 60 stem cell isolations |
| Culture medium: Alpha modification of Eagle's medium (GIBCO/BRL) supplemented with: | Culture medium: Dulbecco's modified Eagle's medium (DMEM)/Ham's F12 (1:1) supplemented with: |
| 20% FCS | 15% fetal bovine serum |
| 100 µM 1-ascorbic acid 2-phosphate | 100 U/ml penicillin |
| 2 mM 1-glutamine | 100 g/ml streptomycin |
| 100 units/ml penicillin | 2 mM L-glutamine |
| 100 µg/ml streptomycin | 2 mM nonessential amino acids |
| Single-cell suspension | Outgrowth |
| Use of cell strainer | |
| Assess only to outer layer of DP and very close layers | Assess to outer and inner part of DP |
| Principal markers: | Principal markers: |
| Perivascular | Mesenchymal stem cells (MSC) |
| | Embryonic stem cells (ES cells) |
| | Neuronal precursors |
| | Perivascular |
| Osteogenic differentiation required BMP-4 | Not required |
| Neurogenic differentiation required EGF, FGF, and rat serum | Not required |
| Chondrogenic differentiation required TGF-β3 and bFGF or TGF-β | Not required |
| High passages are needed in order to obtain number of SHED sufficient for cell therapy | DP multiple transfer ensure sufficient IDPSC number at low passages |

The requirements for inducing differentiation are also different between SHED and IDPSCs. For example, to induce neuronal differentiation, SHED need EGF 20 ng/ml (BD Bioscience), FGF 40 ng/ml (BD Bioscience) and 3% rat serum. They need four weeks in neural inductive culture in order to show neural morphology and to increase expression of neuronal markers.

In part because of these differences, IDPSCs have advantages over SHED regarding neurogenesis. In one study, SHED were injected into the dentate gyrus of the hippocampus of immunocompromised mice. The data demonstrated that SHED were able to survive for more than 10 days in mice hippocampus and to express NFM, which were expressed also by undifferentiated SHED (Miura et al., 2003). In another study, pre-differentiated SHED (SHED- Cyclosporine A is shown to decreases the size of the ischemic brain infarct in rats and to protects against synaptic dysfunction and cell death in rodent models of traumatic brain infarct as well as to protects striatal neurons from mitochondrial dysfunction in Huntington disease (Matsomoto et al., 1999; Albensi et al. 2000; Leventhal et al., 2003). Therefore, benefits observed in Parkinsonian rats and HI cannot be purely attributed to SHED but also to Cyclosporine A intervention.

2. Comparison with Other Therapeutic Stem Cells for the Treatment of Neurological Conditions As shown in Table 6, hIDPSCs from Avita International LTD are advantageous over other therapeutic stem cells on the market or in clinical trial. Avita International LTD's hIDPSCs have a good safety profile with low risk of immunogenicity and a low cost of production as they can be cryopreserved.

TABLE 6

Comparison of commercially produced stem cells.

| Company (ticker) | BrainStorm Cell Therapeutics Inc. (BCLI) | NeuralStem Inc. (CUR) | Kadimastem (KDST) | Avita International LTD |
|---|---|---|---|---|
| Cell Source | Autologous MSC from bone marrow | Allogenic; 8-week-old fetal spinal cord-derived cells | hESCs (embryo) and iPSCs (adult) | hIDPSCs from dental pulp |
| Modifications | Induction of neurotrophic factor secretion | No | Induction to differentiate into astrocyte precursor cells | No |
| Cell Safety Profile | Good with low risk of immunogenicity | Less safe with risk of unwanted differentiation (teratoma) and/or risk of rejection | Less safe with risk of unwanted differentiation (teratoma) and/or risk of rejection | Good with low risk of immunogenicity |
| Immuno-suppression | Not required | Required | Required | Not required |
| Cryo-preservation | Not yet-studying the feasibility of cryopreservation of MSCNCs during early phase expansion | Cell can be expanded and frozen | Cells can be frozen in differentiated state | Cell can be expanded and frozen |
| Clinical Trials | Compassionate Care: Phase I/II complete (Israel); Phase II underway (US) | Phase I/II begins in 2014 (Mexico); Phase II ends in 4Q2014 (US) | Not yet in clinical trials | On going Phase I (Brazil) |
| Cost | High | Low | Low | Low |

Example 5

Product Description and Specifications

Table 7 depicts CELLAVITA™ (stem cells) specifications.

Analytical Procedure
Safety QC—Mycoplasma Test

Mycoplasma tests will be performed regularly during cultivation of hIDPSC with an in-house RT-PCR test (EZ-PCR Biological Industries, Israel) according to the manufacturer's protocol.

TABLE 7

Drug Product Release Monograph

| Method of Analysis | Characteristics | Specification |
|---|---|---|
| Appearance-Morphological test | Morphology | Normal fibroblast like morphology under inverted microscope inspection |
| Cell viability via Trypan Blue exclusion | Viability | >95% |
| Cell doublings | Cell doublings number | At least doubling of cell number in 24 hours |
| CFU | Cell forming units assay | >5 colonies |
| Sterility (21CFR/EP/USP) | Microbial contamination | No growth detected after 14 days |
| Endotoxins (LAL) | Less than or equal to 1.0 EU/mg A280 protein | <0.005 EU/mg A280 protein |
| PCR Mycoplasma test | Mycoplasma detection Culture-no growth detected | Undetectable |
| Impurities | | |
| FACS analysis | Allogeneic marker | Negative to HLA class II |
| FACS analysis | HSC marker | Negative to CD34 |
| FACS analysis | Phenotype analysis MSC | Positive to CD73, CD105 |
| FACS analysis Assay | Phenotype analysis neuronal factors | Positive to NGF, nestin |
| ELISA assay | Neuronal factors | Positive to BDNF |

Safety Characteristics—Karyotype Analysis

Karyotype analysis will be performed several times showing karyotype stability and these data are already published (Kerkis et al., 2006; Beltrão-Braga, 2011; Lizier et al., 2012). Additionally, independent karyotype analysis will be performed in Cytogenetics.

Safety and Identity QC—Flow Cytometric Analysis of Cell Surface Antigens

Immunostaining of cell surface markers will be carried out with monoclonal antibodies against various surface antigen markers: HLA-DR-FITC, CD44-FITC, CD45-APC, CD105-PE, CD73-FITC, CD90-APC (eBioscience CA, USA), SOX2-PE, Nestin-PE, β-III Tubulin-APC, NGF-PE (R&D systems, MN, USA). $2 \times 10^5$ cells will be used for FACS experiments. Cells will be washed twice with PBS (w/o Ca and Mg) and suspended in 50 µl PBS. Cells will be then incubated with antibodies for 15 min at room temperature. The cells will be washed twice with PBS and analyzed with a Becton-Dickinson flow cytometer. The fluorescence of PE (FL2), FITC (FL1), APC (FL4) will be detected in 575 nm, 530 nm and 600 nm emission wave lengths, respectively.

Activity Bioassay QC—ELISA Assay

BDNF levels will be quantified by using a human BDNF Quantikine ELISA kit, according to the manufacturer's protocol (R&D Systems, Minn., USA).

$1 \times 10^6$ cells from different harvests will be inoculated in 75-cm2 plastic flasks. The supernatants were harvested approximately 4 days after inoculation. The results were expressed as the BDNF concentration.

Batch Analysis

Table 8 depicts batch Number 001H1-30/P1-5/F analysis.

Stability

Figure 11:
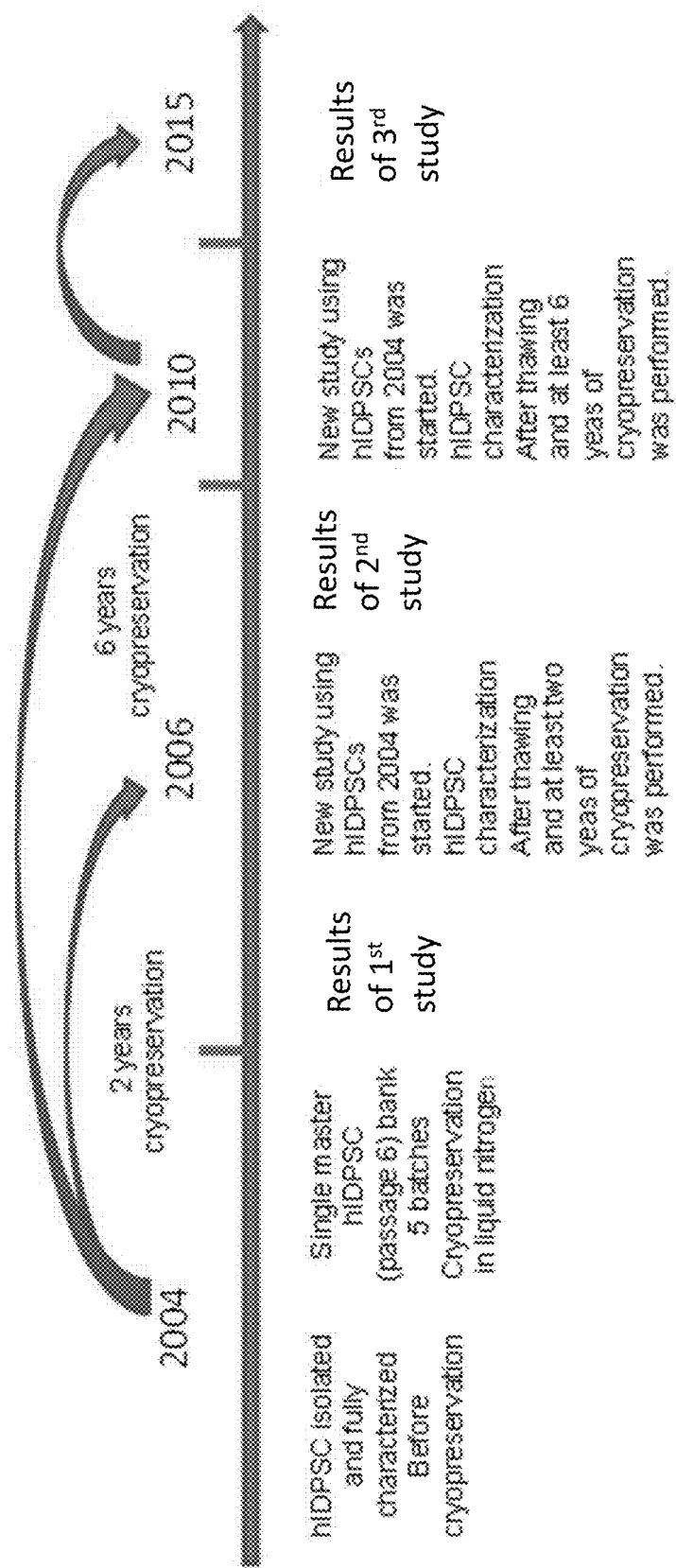
FIG. 11 depicts a time line of stability studies of hIDPSC during long term cryopreservation, following thawing and shipping before local of application in animal models of human diseases.

Avita performed non GMP, non GLP studies regarding hIDPSC stability. For this purpose a single master cell bank, which may mitigate variability of the final batch, was established. It was composed by 5 batches, each derived from Dental Pulp of one individual. The cells were produced as described in FIG. 1. The time line of stability studies of hIDPSC is presented on FIG. 11.

The expression of stem cell markers, dynamics of cell proliferation, and differentiation capacity of hIDPSC derived from four batches before cryopreservation as well as migration and biodistribution in different organs after injection into Nude mice were studied. CELLAVITA™ (stem cells) showed that under standard culture conditions these cells at passage 6 from four independent batches express surface markers of mesenchymal stem cells (MSC) such as CD105, CD73, and CD13. Nevertheless, they lack the expression of CD45, CD34, CD14, CD43, and of HLA-DR. These cells were able to undergo spontaneous and induced in vitro differentiation into osteoblasts, adipocytes and chondroblasts, muscle cells, and into neurons in vitro. After transplantation into normal mice, these cells showed significant engraftment in liver, spleen, brain and kidney, among others.

Stability Program Development

Past experience showed that both the initial cell Poll (primary cells) and its final blend (after P5 expansion and mixing of all transfers) are stable when cryopreserved at −192° C.

The stability program being developed by the company Cellavita Pesquisas Cientificas Ltda. Scientific Research Ltda. for CELLAVITA™ (stem cells) product will be based on:

TABLE 8

| Batch Number 001H1-30/P1-5/F | | | |
|---|---|---|---|
| Method of Analysis | Characteristics | Specification | Result |
| Characteristics | | | |
| Appearance-Morphological test | Morphology | Normal fibroblast like morphology under inverted microscope inspection | Confirms |
| Cell viability via Trypan Blue exclusion | Viability | >95% | Confirms |
| Cell doublings | Cell doublings number | At least doubling of cell number in 24 hours | Confirms |
| CFU | Cell forming units assay | >5 colonies | Confirms |
| Safety | | | |
| Sterility (21CFR/EP/USP) | Microbial contamination | No growth detected after 14 days | Confirms |
| Endotoxins (LAL) | Less than or equal to 1.0 EU/mg A280 protein | <0.005 EU/mg A280 protein | Confirms |
| PCR Mycoplasma test | Mycoplasma detection Culture-no growth detected | Undetectable | Confirms |
| FACS analysis | Allogeneic marker | Negative to HLA-DR | Confirms |
| FACS analysis | HSC marker | Negative to CD34 | Confirms |
| Identity: mesenchymal stem cell markers and neuronal markers | | | |
| FACS analysis | Phenotype analysis MSC | Positive to CD13, CD73, CD105 | Confirms |
| FACS analysis | Phenotype analysis neuronal factors | Positive to NGF, nestin | Confirms |
| Activity Bioassay | | | |
| ELISA assay | Neuronal factors | Positive to BDNF | Confirms |

Time to perform;
Steps to be carried out;
Study Conditions;
Analysis and specifications.
The basic program should be completed before the start of the Phase 2 proof of concept (POC) clinical study.

Example 6

3-Nitropropionic Acid (3-NP) Rat Model of Huntington Disease Ethical Issue

All studies were approved by the ethics committee of the Nuclear and Energy Research Institute (Instituto de Pesquisas Energéticas e Nucleares—IPEN), University of Sao Paulo, São Paulo, Brasil. Protocols concerning the maintenance, care, and handling of experimental animals are in accordance with all Brazilian current legislation and with internationally recognized norms and protocols. All staff working with experimental animals were fully accredited as a staff researcher/technician and were properly trained in the use of animals for experimental scientific purposes in accordance with current Brazilian regulations Main Goal The research group tested the neuroprotective and/or neural tissue remodeling effects of hIDPSC in a 3-NP chemical model of Huntington's disease.

Animal Model

Systemic administration of the mitochondrial toxin 3-nitropropionic acid (3-NP) serves as a chemical model of Huntington's disease in rodents and non-human primates and has been used to test potential drug therapies. 3-NP is an irreversible mitochondrial succinate dehydrogenase (SDH) inhibitor that causes cell death mainly in the striatum and also in GABAergic medium spiny projection neurons and spiny interneurons. Because of its ability to cross the blood-brain barrier, 3-NP can be administered systemically, causing selective neurodegeneration of the striatum or the entire corpus striatum. Depending on the drug regimen, 3-NP administration can simulate different stages of Huntington's disease. Intraperitoneal injections of two 3-NP doses lead to hyperkinetic symptoms in mice in the early stages of disease, whereas four or more doses result in hypoactivity in the late stages of disease (Beal et al., 1993; Brouillet et al., 1995; Yang et al., 2008; Borlogan et al., 1997).

It should be noted that the 3-NP-treated animals (chemical model) has an important limitation if compared to transgenics. In 3-NP model, the striatum lesion can regenerate spontaneously, after 10-12 days because of the presence of normal intrinsic neuronal precursors and an absence of genetic background which provides constant neurodegeneration. Therefore, difference in motor and functional improvements between experimental and control groups can be observed before spontaneous neuroregeneration.

Brief Protocol of hIDPSC Transplantation

Figure 12:
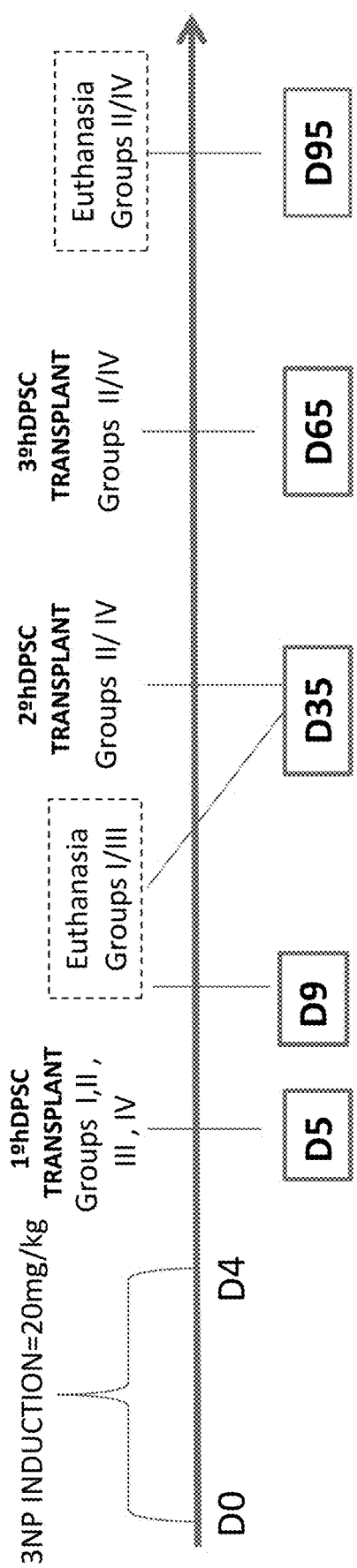
FIG. 12 depicts the timeline of the pilot study in the HD disease model (groups I, II, III, and IV). HD was induced during the first four days, day 0 (D0) to day 4 (D4) by 3-NP. On the fifth day (D5), IDPSC transplantation was administered via intravenous injection. Animals were euthanized on day 9 (D9) followed by brain tissue fixation and histological analysis of lesion for detection of IDPSC biodistribution and engraftment (Vybrant+immunohistochemistry using specific antibodies). Group I and III were euthanized on day 35 (D35) and groups II and IV on day 95 followed by brain tissues fixation and histological analysis of lesion for detection of IDPSC biodistribution and engraftment (Vybrant+immunohistochemistry using specific antibodies).

Lewis rats (n=124) weighing 350-450 g were injected 20 mg/kg 3-NP intraperitoneally (IP) once daily for four days. The animals were kept under a light/dark cycle for 12 h and given free access to food and water. Rats were injected IP with 3-NP to induce brain injuries. Next, they were anesthetized and injected into the caudal vein with either one or three doses of $1\times10^6$ each in 250 µl of saline solution or $1\times10^7$ in 300 µl of saline solution hIDPSCs per animal, which corresponds to $0.35\times10^6$ and to $3.5\times10^6$ per kg, respectively. Multiple doses were administered 30 days apart (FIG. 12).

Each treatment group was paired with a control group that received saline solution only (untreated). Thus, animals were grouped into five groups as shown in Table 9.

TABLE 9

Groups and number of the animals used in the present study.

| Groups | Treatment | Total number | Deaths | Animals composed this study |
|---|---|---|---|---|
| 1 (n = 40) | Treated = 1 × 10$^6$ hIDPSCs in a single administration (n = 19) | 19 | 2 | 17 |
| | Untreated = saline solution (n = 20) | 21 | 0 | 20 |
| 2 (n = 40) | Treated = 1 × 10$^6$ hIDPSCs in three administrations (n = 19) | 19 | 5 | 14 |
| | Untreated = saline solution (n = 21) | 21 | 9 | 12 |
| 3 (n = 21) | Treated = 1 × 10$^7$ hIDPSCs in a single administration (n = 10) | 10 | 0 | 10 |
| | Untreated = saline solution (n = 11) | 11 | 0 | 11 |
| 4 (n = 23) | Treated = 1 × 10$^7$ hIDPSCs in three administrations (n = 14) | 14 | 5 | 9 |
| | Untreated = saline solution (n = 9) | 9 | 3 | 6 |
| 5 (n = 10) | Control = no administration of 3-NP, saline solution, or hIDPSCs (n = 10) | 10 | 0 | 10 |

Functional Analysis

Semi-Quantitative Neurological Scale

Ambulatory abilities were assessed twice a week by one blinded observer for each experimental group using the quantitative neurological scale adapted from Ludolph et al., (1991). This scale measures the ambulatory behavior (scored 0-4) of rats on a flat wooden surface as follows: 0: normal behavior; 1: general slowness; 2: incoordination and gait abnormalities; 3: upper limb paralysis or impairment, inability to move; and 4: inability to leave the lying position.

At baseline, all rats (30) in both groups exhibited normal behavior with no marked gait abnormality before treatment with 3NP, thus receiving a score 0. At the end 3NP administration (4 days) end of the of 3NP induction, a total of the 76 rats presented general slowness (score 1); 2 rats presented difficult to move to move (score 2); 20 rats exhibited incapacity to move resulting from forelimb and hindlimbs impairment (score 3); 24 rats presented recumbence and consequently death (score 4). After 24 hours HIDPSC transplantation, the rats treated with 3NP+hIDPSC (both doses) performed better compared to rats treated with 3NP. However, 5-days after hIDPSC transplantation the rats exhibited better improvement after HDPSC transplantation. Total of 27 rats presented normal score (score 0). Furthermore 20 rats presented score 1, 3 score 2 and 2 score 3 and no rats presented score 4 after HIDPSC transplantation (Table 11). While control group (3NP+saline solution) 38 rats presented score 1, 1 score 2 and 5 score 3 and 1 rat presented score 4 (Table 10).

TABLE 10

Neurological rating scale scores after 5 days end 3NP treatment (4 days). Scores are for rats in the control group (3NP + saline solution).

| Group | Score 0 | Score 1 | Score 2 | Score 3 | Score 4 |
|---|---|---|---|---|---|
| GI | 0 | 16 | 0 | 0 | 0 |
| GII | 0 | 9 | 0 | 3 | 0 |
| GIII | 0 | 10 | 0 | 1 | 0 |
| GIV | 0 | 3 | 1 | 1 | 1 |
| TOTAL | 4 | 38 | 1 | 5 | 1 |

TABLE 11

Neurological rating scale scores after 5 days end 3NP treatment (4 days). Scores are for rats in the treatment group (3NP + hIDPSC).

| Group | Score 0 | Score 1 | Score 2 | Score 3 | Score 4 |
|---|---|---|---|---|---|
| GI | 8 | 11 | 0 | 0 | 0 |
| GII | 10 | 3 | 0 | 1 | 0 |
| GIII | 7 | 3 | 0 | 0 | 0 |
| GIV | 2 | 3 | 3 | 1 | 0 |
| TOTAL | 27 | 20 | 3 | 2 | 0 |

Table 12 depicts neurological score of control group (3NP+ saline solution) and hIDPSC group (3NP+hIDPSC transplant) after 3NP treatment (4 days of administration), 1 day and 5 days after 3NP induction and after HIDPSC transplantation. Normal behavior with no gait abnormalities (score 0); general slowness (score 1); incoordination and gait alterations (score 2); inability to move either the hind limbs or forelimbs (score 3); and inability to leave the lying position. This last group eventually died (score 4). Group 1=Treated=$1\times10^6$ hIDPSCs in a single administration; Group 2=Treated=$1\times10^6$ hIDPSCs in three administrations; Group 3=Treated=$1\times10^7$ hIDPSCs in a single administration Group 4=Treated=$1\times10^7$ hIDPSCs in three administrations.

TABLE 12

Neurological scors of various groups of rats.

| Animal | Treatment | dose and HIDPSC and frequency | neurological score AF 3NP | neurological score AF 1 DAY | neurological score AF 5 DAYS |
|---|---|---|---|---|---|
| GROUP I | | | | | |
| 1 | 3NP + SAL | GI | 1 | 1 | 1 |
| 2 | 3NP + SAL | GI | 1 | 1 | 1 |
| 3 | 3NP + SAL | GI | 1 | 1 | 1 |
| 4 | 3NP + SAL | GI | 1 | 1 | 1 |
| 5 | 3NP + SAL | GI | 1 | 1 | 1 |
| 6 | 3NP + HIDPSC | GI | 1 | 1 | 1 |
| 7 | 3NP + HIDPSC | GI | 1 | 1 | 1 |
| 8 | 3NP + HIDPSC | GI | 1 | 1 | 1 |
| 9 | 3NP + HIDPSC | GI | 1 | 1 | 1 |
| 10 | 3NP + HIDPSC | GI | 1 | 1 | 1 |
| 11 | 3NP + SAL | GI | 1 | 1 | 1 |
| 12 | 3NP + SAL | GI | 1 | 1 | 1 |
| 13 | 3NP + SAL | GI | 1 | 1 | 1 |
| 14 | 3NP + SAL | GI | 1 | 1 | 1 |
| 15 | 3NP + SAL | GI | 1 | 1 | 1 |
| 16 | 3NP + HIDPSC | GI | 1 | 1 | 1 |
| 17 | 3NP + HIDPSC | GI | 1 | 1 | 1 |
| 18 | 3NP + HIDPSC | GI | 1 | 1 | 1 |
| 19 | 3NP + HIDPSC | GI | 1 | 1 | 1 |
| 20 | 3NP + HIDPSC | GI | 1 | 1 | 1 |
| 64 | 3NP + SAL | GI | 1 | 1 | 1 |
| 65 | 3NP + SAL | GI | 1 | 1 | 1 |
| 66 | 3NP + SAL | GI | 1 | 1 | 1 |
| 67 | 3NP + SAL | GI | 3 | 3 | 1 |
| 68 | 3NP + HIDPSC | GI | 1 | 0 | 0 |
| 69 | 3NP + HIDPSC | GI | 1 | 0 | 0 |
| 70 | 3NP + HIDPSC | GI | 1 | 0 | 0 |
| 71 | 3NP + SAL | GI | 1 | 1 | 1 |
| 72 | 3NP + SAL | GI | 1 | 1 | 1 |
| 73 | 3NP + SAL | GI | 1 | 1 | 1 |
| 74 | 3NP + SAL | GI | 1 | 1 | 1 |
| 75 | 3NP + SAL | GI | 1 | 1 | 1 |
| 76 | 3NP + HIDPSC | GI | 1 | 1 | 1 |
| 77 | 3NP + HIDPSC | GI | 1 | 0 | 0 |
| 78 | 3NP + HIDPSC | GI | 4 | 4 | death |
| 79 | 3NP + HIDPSC | GI | 1 | 0 | 0 |
| 80 | 3NP + HIDPSC | GI | 1 | 0 | 0 |
| 81 | 3NP + HIDPSC | GI | 1 | 0 | 0 |
| 82 | 3NP + HIDPSC | GI | 1 | 0 | 0 |
| 83 | 3NP + HIDPSC | GI | 4 | | death |
| GROUP II | | | | | |
| 21 | 3NP + SAL | GII | 4 | 4 | death |
| 22 | 3NP + SAL | GII | 3 | 3 | 3 |
| 23 | 3NP + SAL | GII | 3 | | death |
| 24 | 3NP + SAL | GII | 3 | 4 | death |
| 25 | 3NP + SAL | GII | 4 | 4 | death |
| 26 | 3NP + HIDPSC | GII | 3 | 3 | 3 |
| 27 | 3NP + HIDPSC | GII | 4 | | death |
| 28 | 3NP + HIDPSC | GII | 4 | 4 | death |
| 29 | 3NP + HIDPSC | GII | 3 | 3 | 1 |
| 30 | 3NP + HIDPSC | GII | 3 | 3 | 1 |
| 31 | 3NP + SAL | GII | 4 | 4 | 3 |
| 32 | 3NP + SAL | GII | 4 | 4 | death |
| 33 | 3NP + SAL | GII | 4 | 4 | death |
| 34 | 3NP + SAL | GII | 4 | 4 | death |
| 35 | 3NP + SAL | GII | 3 | 3 | death |
| 36 | 3NP + SAL | GII | 3 | 3 | 3 |
| 37 | 3NP + HIDPSC | GII | 3 | | death |
| 38 | 3NP + HIDPSC | GII | 4 | 4 | death |
| 39 | 3NP + HIDPSC | GII | 3 | 3 | 1 |
| 40 | 3NP + HIDPSC | GII | 4 | 4 | death |
| 21A | 3NP + SAL | GII | 4 | 4 | death |
| 22A | 3NP + SAL | GII | 1 | 1 | 1 |
| 23A | 3NP + SAL | GII | 1 | 1 | 1 |
| 24A | 3NP + SAL | GII | 1 | 1 | 1 |
| 25A | 3NP + SAL | GII | 1 | 1 | 1 |
| 26A | 3NP + HIDPSC | GII | 1 | 0 | 0 |
| 27A | 3NP + HIDPSC | GII | 1 | 0 | 0 |
| 28A | 3NP + HIDPSC | GII | 1 | 0 | 0 |
| 29A | 3NP + HIDPSC | GII | 1 | 0 | 0 |
| 30A | 3NP + HIDPSC | GII | 1 | 0 | 0 |
| 31A | 3NP + SAL | GII | 1 | 1 | 1 |
| 32A | 3NP + SAL | GII | 1 | 1 | 1 |
| 33A | 3NP + SAL | GII | 1 | 1 | 1 |
| 34A | 3NP + SAL | GII | 1 | 1 | 1 |
| 35A | 3NP + SAL | GII | 1 | 1 | 1 |
| 36A | 3NP + HIDPSC | GII | 1 | 0 | 0 |
| 37A | 3NP + HIDPSC | GII | 1 | 0 | 0 |
| 38A | 3NP + HIDPSC | GII | 1 | 0 | 0 |
| 39A | 3NP + HIDPSC | GII | 1 | 0 | 0 |
| 40A | 3NP + HIDPSC | GII | 1 | 0 | 0 |
| GROUP IV | | | | | |
| 84 | 3NP + SAL | GIII | 1 | 1 | 1 |
| 85 | 3NP + SAL | GIII | 1 | 1 | 1 |
| 86 | 3NP + SAL | GIII | 1 | 1 | 1 |
| 87 | 3NP + SAL | GIII | 1 | 1 | 1 |
| 88 | 3NP + SAL | GIII | 1 | 1 | 1 |
| 89 | 3NP + HIDPSC | GIII | 1 | 0 | 0 |
| 90 | 3NP + HIDPSC | GIII | 1 | 0 | 0 |
| 91 | 3NP + HIDPSC | GIII | 1 | 0 | 0 |
| 92 | 3NP + SAL | GIII | 1 | 1 | 1 |
| 93 | 3NP + SAL | GIII | 1 | 1 | 1 |
| 94 | 3NP + SAL | GIII | 1 | 1 | 1 |
| 95 | 3NP + SAL | GIII | 1 | 1 | 1 |
| 104 | 3NP + SAL | GIII | 3 | 3 | 3 |
| 96 | 3NP + SAL | GIII | 1 | 0 | 1 |
| 97 | 3NP + HIDPSC | GIII | 1 | 0 | 1 |
| 98 | 3NP + HIDPSC | GIII | 1 | 0 | 1 |
| 99 | 3NP + HIDPSC | GIII | 2 | 2 | 1 |
| 100 | 3NP + HIDPSC | GIII | 1 | 0 | 0 |
| 101 | 3NP + HIDPSC | GIII | 1 | 0 | 0 |
| 102 | 3NP + HIDPSC | GIII | 1 | 0 | 0 |
| 103 | 3NP + HIDPSC | GIII | 1 | 0 | 0 |
| GROUP III | | | | | |
| 41 | 3NP + HIDPSC | GIV | 4 | 4 | death |
| 42 | 3NP + HIDPSC | GIV | 3 | 3 | 1 |
| 43 | 3NP + SAL | GIV | 3 | 3 | death |
| 44 | 3NP + HIDPSC | GIV | 3 | 3 | 0 |

TABLE 12-continued

Neurological scors of various groups of rats.

| Animal | Treatment | dose and HIDPSC and frequency | neuro-logical score AF 3NP | neuro-logical score AF 1 DAY | neuro-logical score AF 5 DAYS |
|---|---|---|---|---|---|
| 45 | 3NP + SAL | GIV | 4 | 4 | death |
| 46 | 3NP + HIDPSC | GIV | 4 | 4 | 2 |
| 47 | 3NP + HIDPSC | GIV | 3 | 3 | 1 |
| 48 | 3NP + HIDPSC | GIV | 4 | 4 | 3 |
| 49 | 3NP + HIDPSC | GIV | 4 | 4 | death |
| 50 | 3NP + SAL | GIV | 4 | 4 | death |
| 51 | 3NP + HIDPSC | GIV | 4 | 4 | 2 |
| 52 | 3NP + SAL | GIV | 4 | 4 | 4 |
| 53 | 3NP + SAL | GIV | 3 | 3 | 3 |
| 54 | 3NP + HIDPSC | GIV | 4 | 4 | death |
| 55 | 3NP + HIDPSC | GIV | 4 | 4 | death |
| 56 | 3NP + HIDPSC | GIV | 3 | 3 | 1 |
| 57 | 3NP + SAL | GIV | 3 | 3 | 2 |
| 58 | 3NP + HIDPSC | GIV | 4 | 4 | 2 |
| 59 | 3NP + HIDPSC | GIV | 3 | 3 | death |
| 60 | 3NP + SAL | GIV | 1 | 1 | 1 |
| 61 | 3NP + SAL | GIV | 1 | 1 | 1 |
| 62 | 3NP + HIDPSC | GIV | 1 | 0 | 0 |
| 63 | 3NP + SAL | GIV | 1 | 1 | 1 |

Histopathological and Immunohistological Analysis

Histopathological and immunohistological analyses were conducted 7, 30, and 90 days after hIDPSC injection; animals were perfused with 4% paraformaldehyde (prepared in PBS, 0.1 mol/L). Tissue fragments were dehydrated in a decreasing ethanol series (75, 95, and 100%) and stained using Nissl staining with 0.1% cresyl violet. Two antibodies, such as, anti-human nuclei and anti-hIDPSC (1:1000, Abcam Plc) were used to determine the presence of hIDPSC in rat brain. To evaluate the neuroprotective and neuroreparative effects of hIDPSC, anti-GABAergic medium spiny neurons DARPP32 (1:1000, Abcam Plc), dopamine D2 (1:800), and BDNF (1:500) antibodies were used.

hIPDSC Engraftment in Rat Brain

Figure 13:
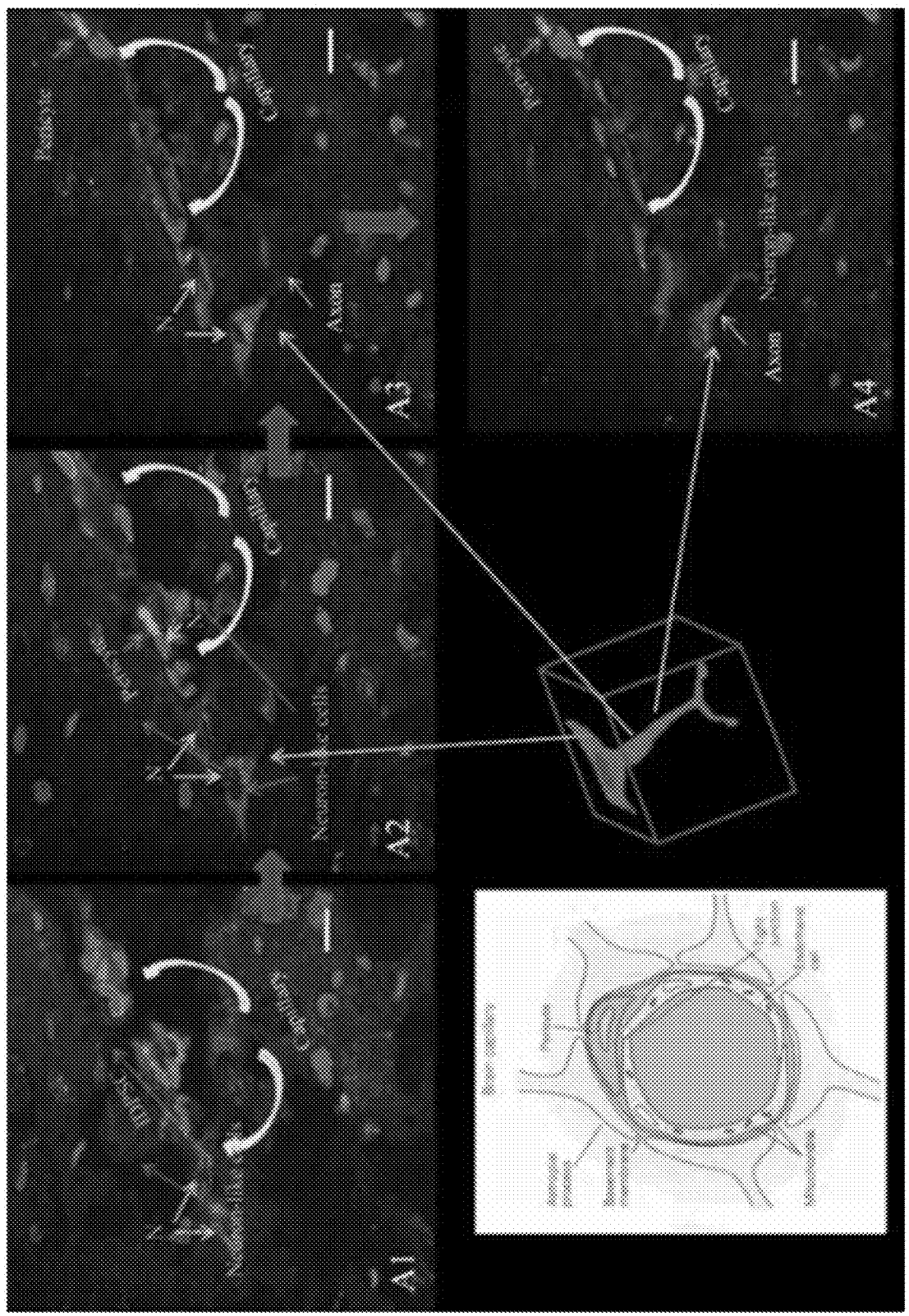
FIG. 13 presents localization of hIDPSC in rat brain tissue four days after hIDPSC administration. hIDPSC cells were stained green (Vybrant) and nuclei were stained red (PI) (A1-A4). Cells were localized mainly in capillaries and two morphological types were observed: neuron-like cells and pericytes. Note the different localization of pericytes in capillaries in A2, A3, and A4; in A4, hIDPSCs are localized in the axon bifurcation. A5: neuron morphology in brain tissues (A2-A4); A6: schematic figure of brain capillary showing pericyte localization. Confocal microscopy. Epifluorescence+Digital interference contrast (DIC) microscopy. Scale bar=10

One of the most relevant findings of the study was that hIDPSCs were detected in the cortex and corpus striatum, indicating that they were able to cross the blood-brain barrier and migrate to the site of injury (FIG. 13). In FIG. 13, optical cuts demonstrate at different depth of focus (A1-A4) the presence of IDPSC stained with Vybrant (green), and nuclei are stained with PI (red). The cells demonstrate capillary predominant association and different morphological types: neuron-like cells and pericytes. On A2, A3, and A4 two pericytes at different locations along capillary can be observed, and both present similar morphology. On A4 embranchment of axons is shown. Neuron nuclei are light with nucleolus, and the difference with perycite nuclei, which are strongly stained, can be observed. Blue is the artificial color of confocal microscope. Microscopy was with epifluorescence+Digital Interference Contrast (DIC), and the scale bar=10 μm.

Figure 14:
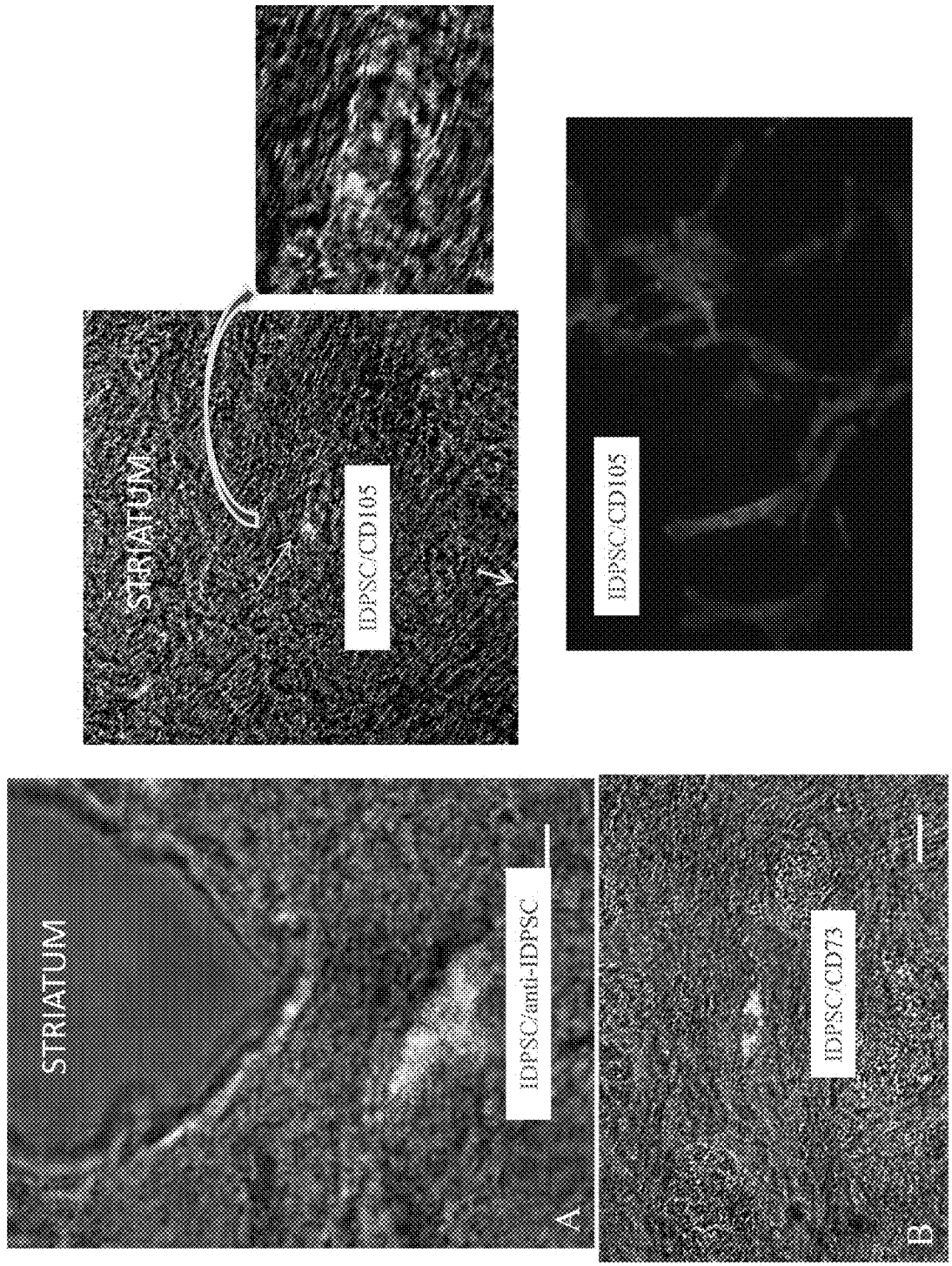
FIG. 14 depicts the engraftment of hIDPSCs four days after IV administration. Optical cut demonstrates hIDPSC stained with Vybrant (green) and positively reacted with anti-hIDPSC antibody (red). Superposition of both produces yellow color. The cells demonstrate near capillary localization. Two markers for MSC were used: CD73 and CD105 demonstrating positive reaction with hIDPSC (A-D). E. Positive control hIDPSC cultured in vitro. Confocal microscope. Epifluorescence+Digital Interference contrast (DIC). Scale bar: A=5 μm; B=10 μm; C=20 μm; D=5 μm.

In addition, four days after hIDPSC administration, a few cells were positive for specific MSC antibodies (anti-CD73 and anti-CD105), indicating that some cells were still undifferentiated at that time (FIG. 14). Nevertheless, hIDPSC-derived neuron-like cells and pericytes (perivascular cells from microvessels) were also observed in the same period (FIG. 13).

Figure 16:
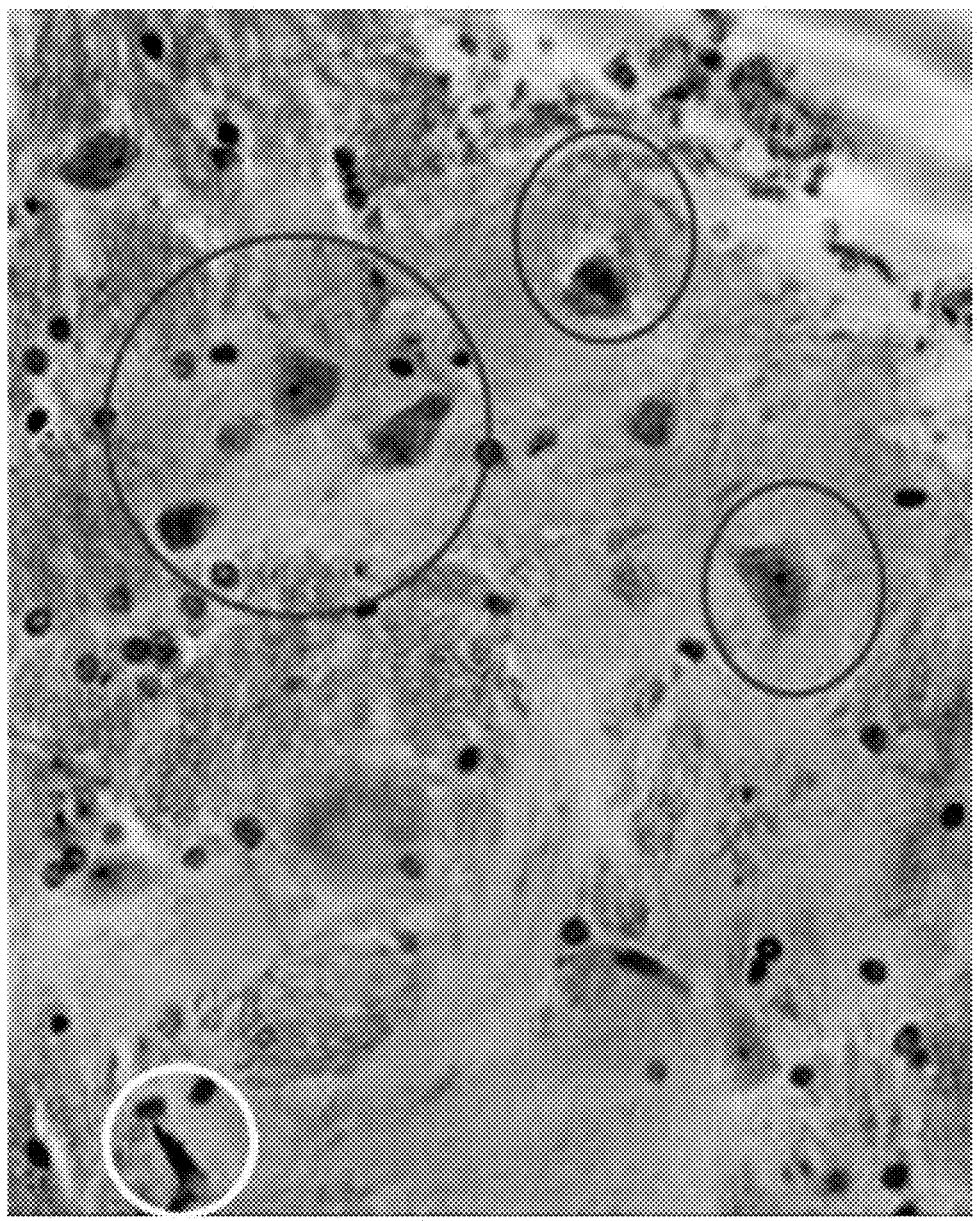
FIG. 16 shows immunohistochemical image of rat brain tissue after 3-NP Injection and hIDPSC administration. Note: positive anti-human nuclei (hNu) immunostaining in cells. Neuron-like cells are circled in blue, and fibroblast-like cells are circled in white. Light microscopy, 90× magnification.

In FIG. 14 the optical cut demonstrates IDPSC stained with Vybrant (green) and positively reacted with anti-IDPSC antibody (red). Superposition of both produce yellow color. The cell demonstrate near capillary localization. Two markers for MSC were used: CD73 and CD105 demonstrating positive reaction with IDPSC. A confocal microscope with epifluorescence+Digital Interference contrast (DIC) was used. Scale bar=A=5 μm; B=10 μm; C=20 μm; D=5 μm Thirty days after hIDPSC transplantation, a few hIDPSCs were observed in the cortex and a large number of cells were observed in the corpus striatum, along the capillaries (FIG. 15). Serial cuts obtained from rat's brain demonstrates neuron like morphology of IDPSC localized in parenchyma (FIG. 15). Additionally, neuron-like and fibroblast-like cells were also observed, confirming that hIDPSCs undergo differentiation (FIG. 16). Unexpectedly the IDPSC were found also in Subventricular zone (SVZ), which is considered a stem cell niche of neurons in the adult brain (FIG. 15).

Figure 17:
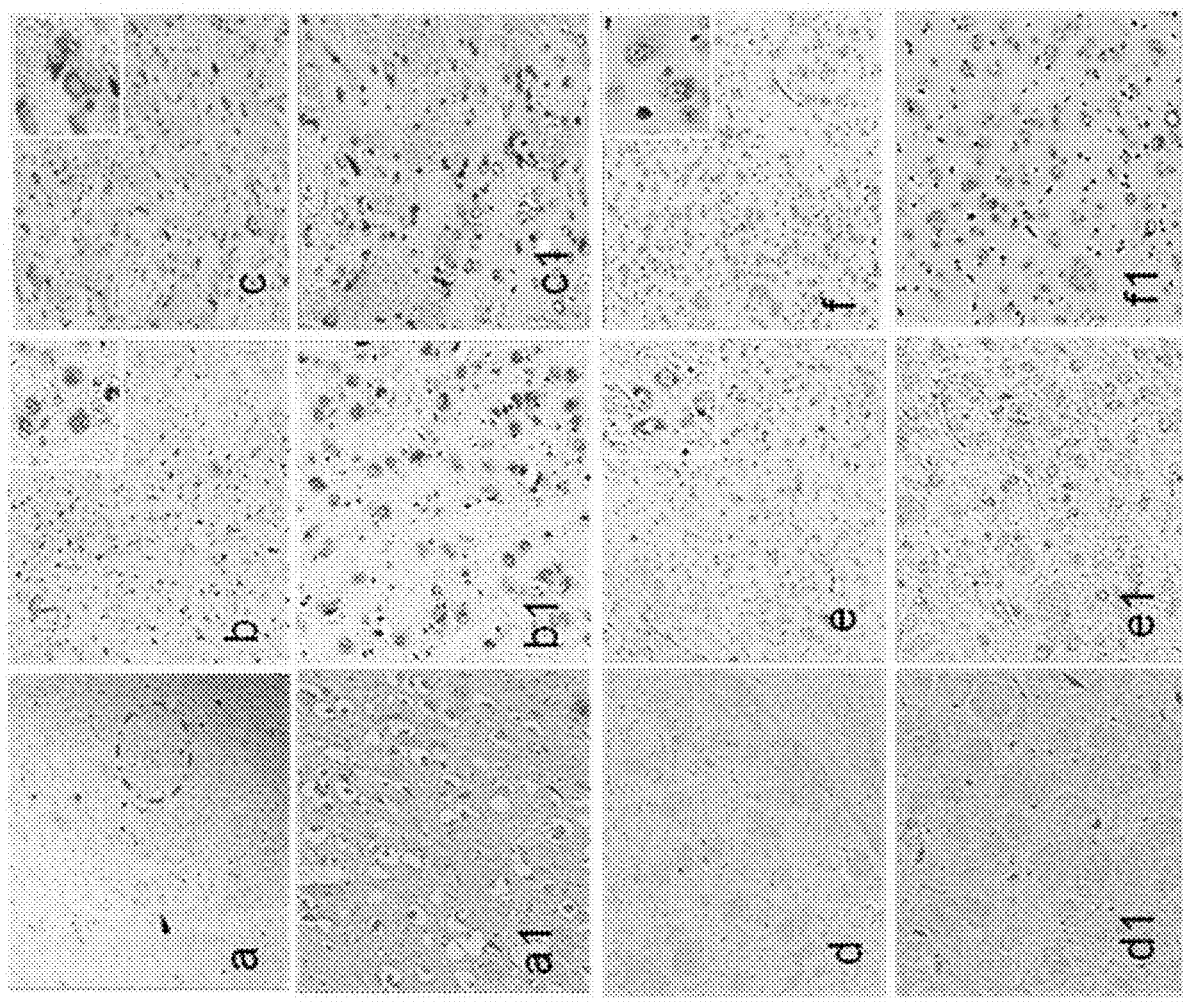
FIG. 17 depicts Nissl Staining in the Striatum of Untreated Animals (3-NP+saline) (a-b1); Control Animals (no 3-NP or hIDPSC) (c, c1); and Treated Animals (3-NP+hIDPSC) (d-f1). Different scores were observed in the experimental groups: score 1 (a, a1, d, and d1); score 2 (b, b1, e, and e1); and score 3 (c, c1, f, and f1). Area of extensive degeneration (a, a1); severe (d, d1); moderate (b, b1, e, and e1), mild (f, f1), and no (c, c1) neuron loss. Magnification: 10× (a-f) and 20× (a-M. Insets in (b, c, e, and f) show typical Nissl-stained neuron morphology (40×). Light microscopy (a-f).
Figure 18:
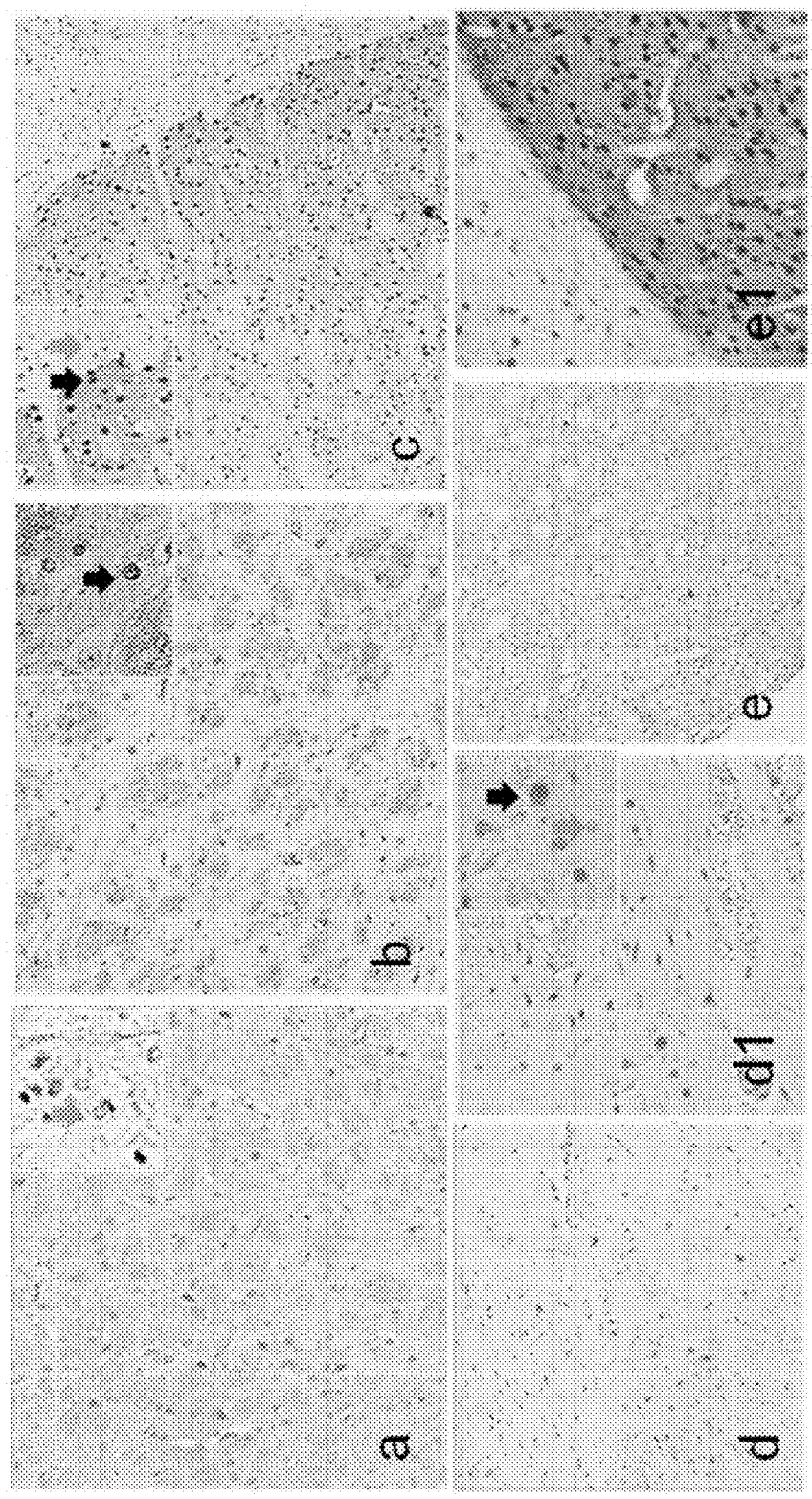
FIG. 18 depicts DARPP32 immunostaining in the corpus striatum of untreated animals (3-NP+saline) (a-b), Controls (no 3-NP or hIDPSC) (c), and Treated Animals (3-NP+hIDPSC) (d-e1). In (a) no immunostaining (blue arrow, score 1), (b) few DARPP32+ cells (score 2), and (c) Control animals (no 3-NP or hIDPSC) showing positive DARPP32 immunostaining (score 3). In (d, d1), neuron loss in Treated animals (3-NP +hIDPSC), with few DARPP32-stained cells (score 2) (black arrow). In (e, e1), strong anti-DARPP-32 immunostaining (score 3). Insets (a, b, c, d1) show DARPP32+ neurons (black arrow) (40×). HE (hematoxylin and eosin)-stained nuclei in blue. Magnification: 10× (a, c, d, and e) and 20× (d, e1).

Neuroprotective and Neuroreparative Effects 3-NP-induced striatal lesions were determined by neuron loss using Nissl staining and DARPP32 expression (FIG. 17 and FIG. 18, respectively). Nissl stains are used to identify neuron structures in the brain and spinal cord (FIG. 17), whereas DARPP32 is a cytoskeleton marker expressed in GABAergic neurons and prevalent in the striatum of healthy mammals (FIG. 18). Using these two markers, neuron loss in the corpus striatum was scored as follows:

Score 1 (severe): severe neuron loss, with areas of degradation, loss of DARPP32 immunostaining in the lateral striatum with little or no cells in the central striatum;

Score 2 (moderate): moderate neuron loss with "dark neurons" (dead or apoptotic neurons) and few DARPP32+ cells; and Score 3 (mild): no neuron loss and intense DARPP32 immunostaining (Vis et al., 2001).

3-NP-treated animals showed complete or partial neuron loss in the striatum compared to controls (no 3-NP or hIDPSC). The two experimental groups (treated and untreated) presented different scores for neuronal loss in the striatum relative to controls. However, morphometric histological analysis revealed that most hIDPSC-treated animals had scores 3 and 2, whereas most untreated animals (3-NP+ saline solution) had neuron loss scores of 2 and 1 (FIG. 18). No animal had visible atrophy (FIG. 17 and FIG. 18).

Figure 19:
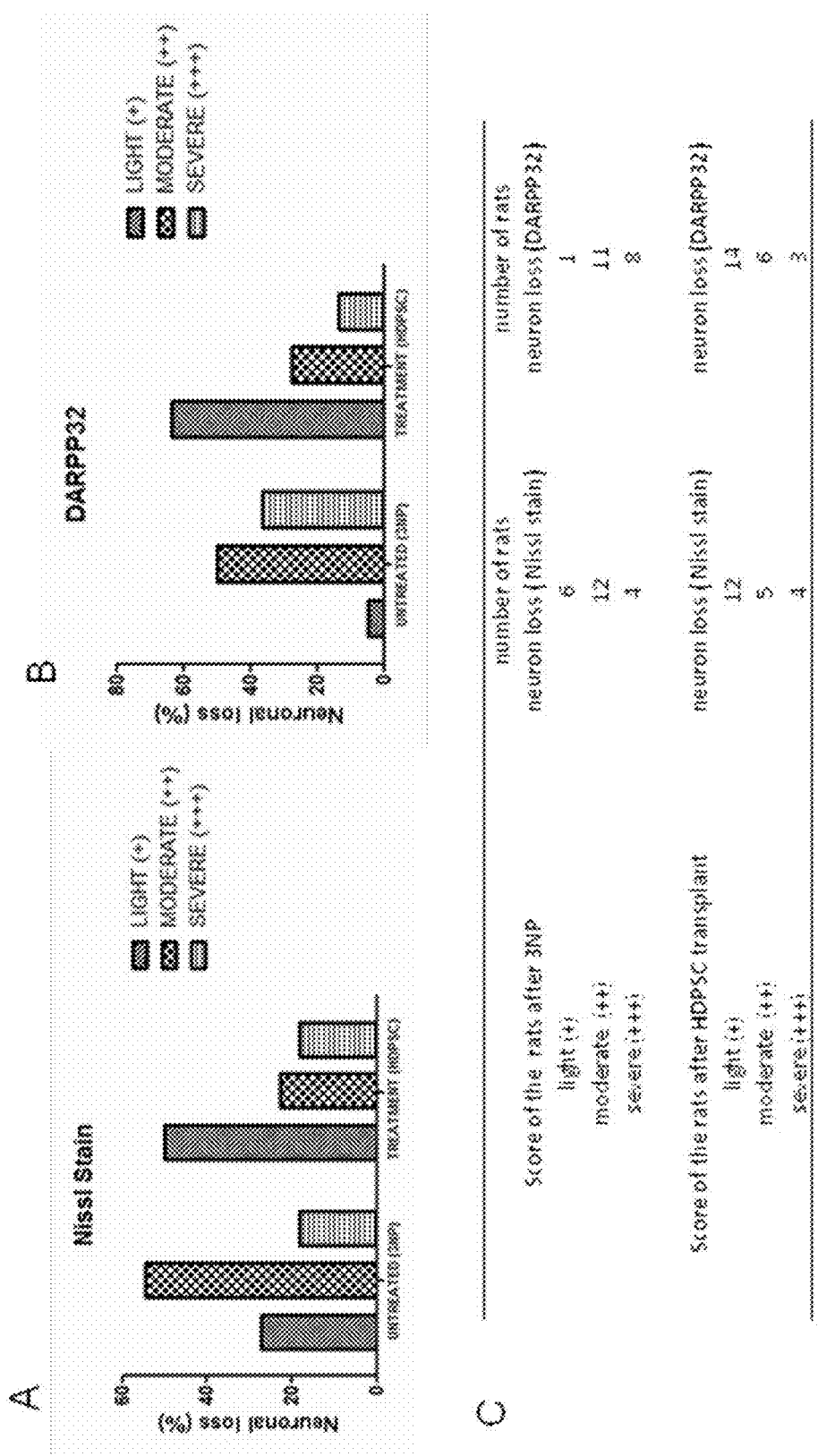
FIG. 19 depicts neuronal growth in the striatum of rats after hIDPSC. Administration of hIDPSC resulted in a neuroreparative effect in hIDPSC-treated animals by (A) Nissl staining and (B) DARPP32 expression. (C) Number of animals showing neuron recovery after hIDPSC administration compared to Controls. Most hIDPSC-treated animals (3-NP+hIDPSC) had scores 3 and 2 (moderate and mild), whereas most Untreated animals (3 NP+saline) had scores 2 and 1 (severe and moderate).

FIG. 19 depicts neuronal growth in the striatum of rats after hIDPSC. Administration of hIDPSC resulted in a neuroreparative effect in hIDPSC-treated animals by (A) Nissl staining and (B) DARPP32 expression. (C) Number of animals showing neuron recovery after hIDPSC administration compared to Controls. Most hIDPSC-treated animals (3-NP+hIDPSC) had scores 3 and 2 (moderate and mild) whereas most untreated animals (3 NP+saline) had scores 2 and 1 (severe and moderate).

Figure 20:
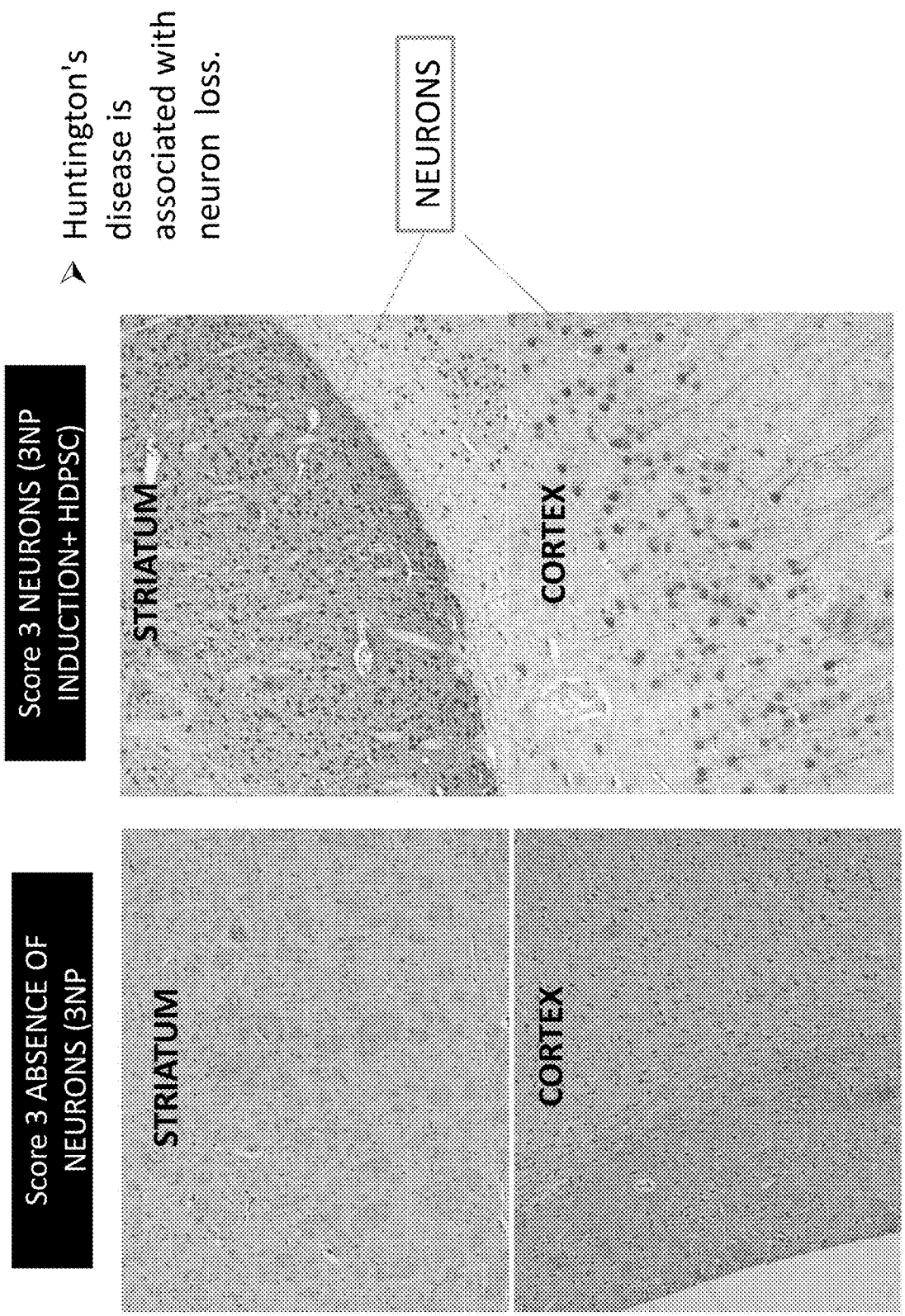
FIG. 20 depicts positive DARPP32 immunostaining for neurons in CELLAVITA™ (stem cells)-treated animals 30 days after hIDPSC transplantation. Untreated animals (3-NP +saline) showed no DARPP32 immunostaining in the striatum or cortex. Rat neuron production was observed in the cortex and striatum of hIDPSC-treated animals. Light microscopy. Magnification: 20× and 90×.

We also observed that DARPP32 expression was higher in hIDPSC-treated animals than in untreated animals (FIG. 20) indicating neuron regeneration. Optical cuts in FIG. 20 demonstrate that neuron positively reacted with DARPP32.

It is reported that dysregulation of dopamine receptor D2 is a sensitive measurement for HD pathology in model mice (Crook et al., 2012). A surprising, unexpected result was obtained in respect to a robust production of DARPP32 positive neurons in rats, which received hIDPSC transplantation. In contrast this was not observed in control groups (FIG. 18). It is important to note that dopamine- and cAMP-regulated neuronal phosphoprotein (DARPP-32), was identified initially as a major target for dopamine and protein kinase A (PKA) in striatum. The regulation of the state of DARPP-32 phosphorylation provides a mechanism for integrating information arriving at dopaminoceptive neurons, in multiple brain regions, via a variety of neurotransmitters, neuromodulators, neuropeptides, and steroid hormones (Svenningsson et al., 2004). HD is associated with severe striatal D1 and D2 receptor loss and taking in consideration that recently it was reported that dysregulation of dopamine receptor D2 as a sensitive measure for Huntington disease pathology in model mice (Crook et al., 2012; Chen et al., 2013), therefore we used this marker to evaluate possible effect of IDPSC in 3-NP induced rats.

Safety

The following physiological parameters were recorded during the experimental period for treated and untreated animals: body weight and feed and water intake. Fewer deaths were observed among hIDPSC-treated animals than 3-NP-injected rats, indicating that hIDPSC administration is safe. In addition, the results suggest that hIDPSC administration improved overall survival by protecting animals from the neurotoxic effects of 3-NP (Table 15).

TABLE 15

The number of survived verus dead animals.

| GROUP | NUMBER OF ANIMALS PER GROUP NP + SAL GROUP | NUMBER OF DEATHS PER GROUP 3NP + 3NP + SAL GROUP | NUMBER OF ANIMALS PER GROUP NP + HIDPSC GROUP | NUMBER OF DEATHS PER GROUP 3NP + HIDPS C GROUP | ANIMALS COMPOSED THIS STUDY |
|---|---|---|---|---|---|
| GI (n = 40) | 19 | 0 | 21 | 2 | 38 |
| GII (n = 40) | 21 | 9 | 19 | 5 | 26 |
| GIII (n = 21) | 11 | 0 | 10 | 0 | 21 |
| GIV (n = 23) | 9 | 3 | 14 | 5 | 15 |
| Control Group GV (1 = 10) | | | 10 | | 10 |
| TOTAL | 60 | 12 | 64 | 12 | 110 |

Figure 21:
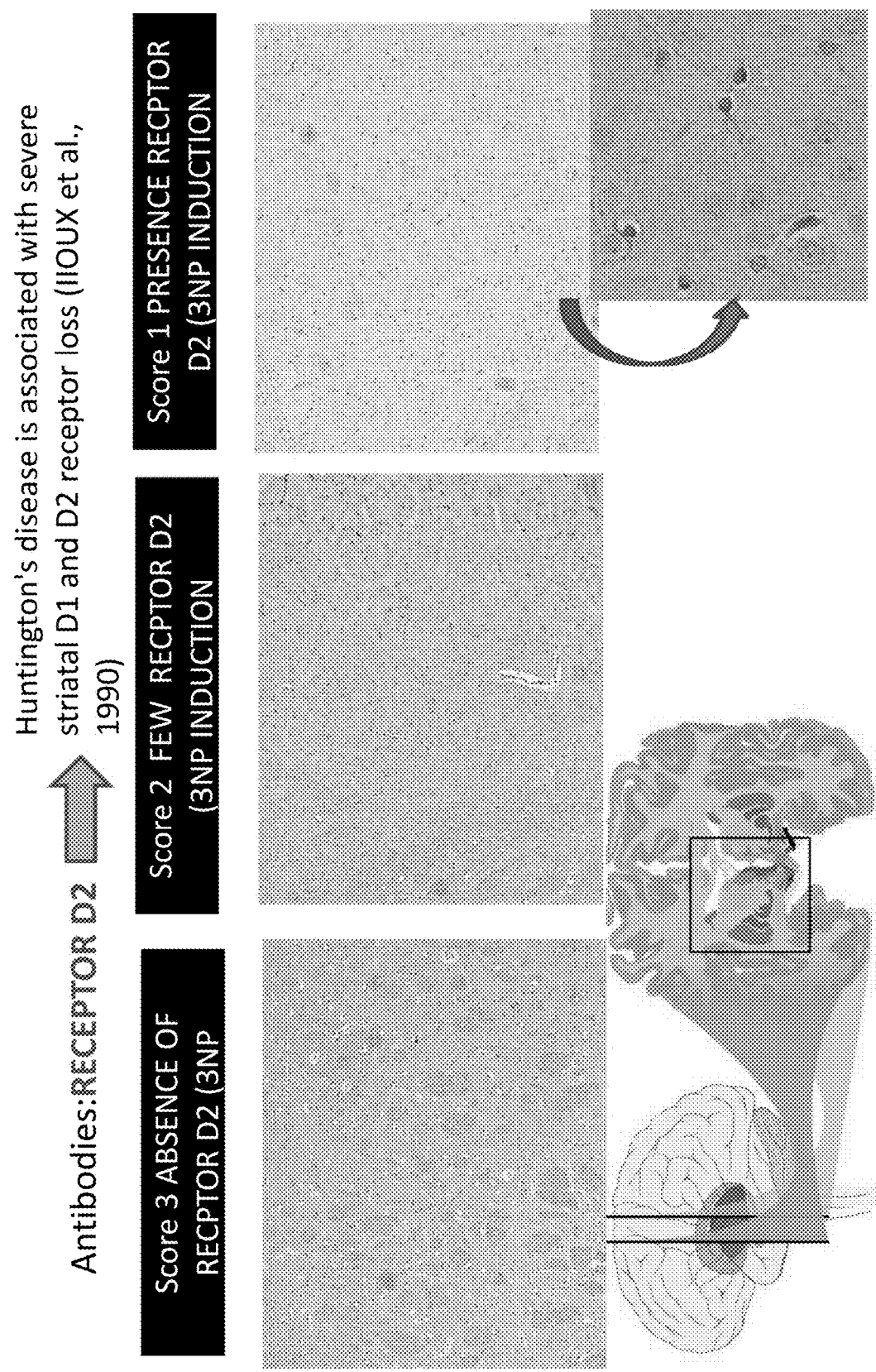
FIG. 21 shows Dopamine Receptor D2 expression in the striatum of rats before and 30 days after hIDPSC Administration; Scores 3 and 2: striatum of untreated animals (3-NP+saline), showing a few D2 receptors in score 2. Score 1: striatum of treated-animals (3-NP+hIDPSC), showing positive receptor D2 immunostaining. Inset: high magnification showing positive D2 immunostaining and neuron morphology.

Surprisingly, we observed significant differences in receptor D2 expression in rats, which received IDPSC in comparison with untreated groups, a few of expression of receptor D2 cells can be observed in the striatum of control animals (FIG. 21).

Figure 22:
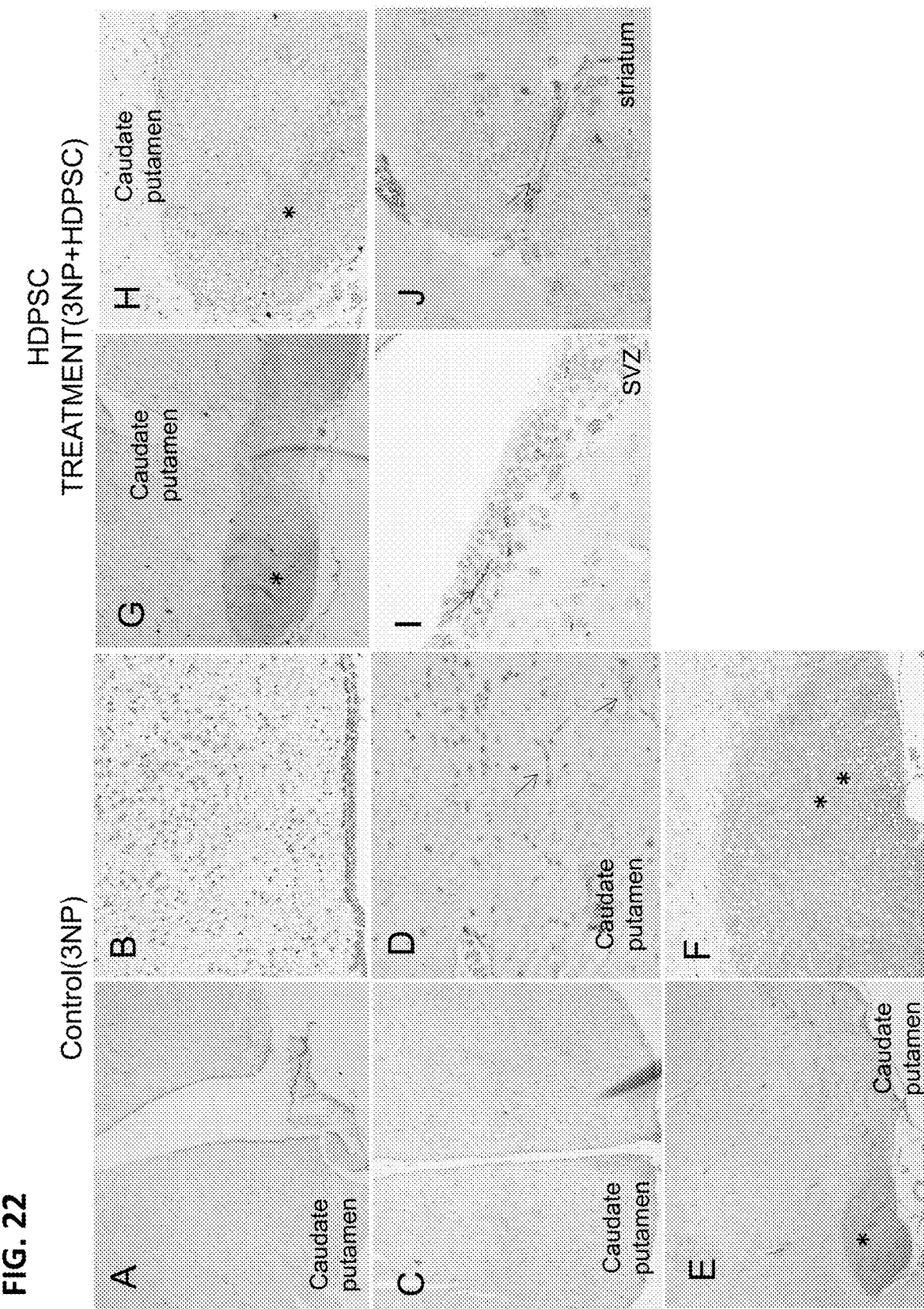
FIG. 22 depicts BDNF expression in rat brain tissue after (a-f) 3-NP Injection and (g j) CELLAVITA™ (stem cells) administration (a, b) Absence of BDNF expression seven days after 3-NP injection and (c, d) low expression after 30 days (e, f). Control animals (no 3-NP or CELLAVITA™ (stem cells)). BDNF expression 7 (g, h) and 30 (i, j) days after CELLAVITA™ (stem cells) administration. Magnification: 10× (a, c, e, f, g, and h) and 20× (b, d, i, and j).

Reduced BDNF's mRNA and protein levels have been observed in the cerebellum, caudate putamen, striatum, and cerebral cortex of HD patients (Adachi et al., 2014). In the current study, BDNF expression was observed in the striatum, caudate, putamen, and subventricular zone of hIDPSC-treated animals 7 and 30 days after hIDPSC administration (FIG. 22). BDNF expression in the subventricular zone indicates that hIDPSC promoted neurogenesis. No BDNF expression was observed in untreated animals (3-NP +saline).

Figure 23:
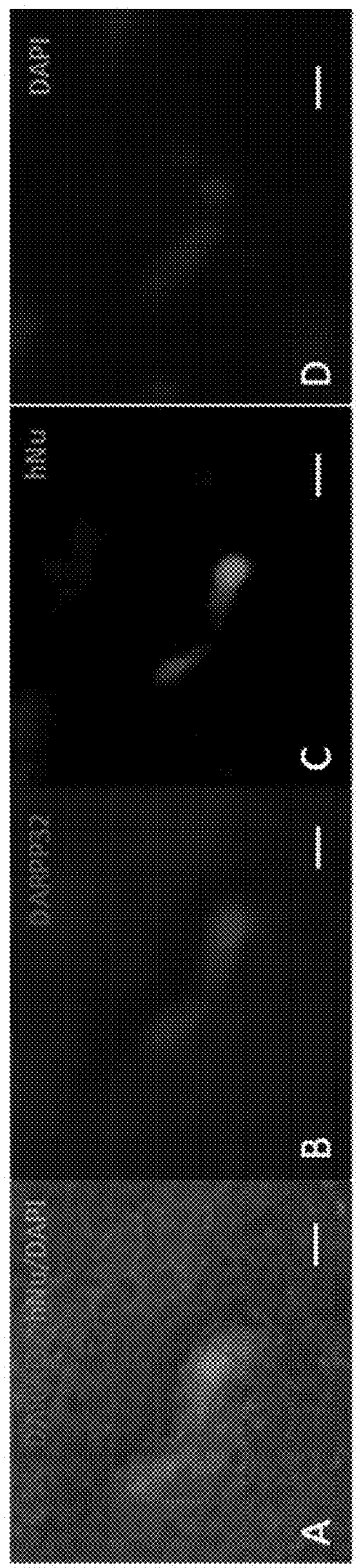
FIG. 23 depicts DARP32 expression in the striatum of rats 30 days after CELLAVITA™ (stem cells) administration in a 3-NP model of HD. Confocal microscopy, overlapping images in A. Epifluorescence+Digital interference contrast (DIC) microscopy. B-D: Epifluorescence. Scale bar: 10 µm.

Co-localization of hIDPSC was observed with the motor neuron marker DARRP32, suggesting that hIDPSCs differentiate into mature neurons. DARPP32 expression was detected in the striatum of hIDPSC-treated animals 30 days after hIDPSC administration in this 3-NP model of HD (FIG. 23). These data indicate that hIDPSCs differentiate into GABAergic spiny neurons in vivo. It should be noted that integration of neurotransmitter and neuromodulator signals in the striatum plays a central role in basal ganglia functions. Moreover, DARPP32 is a key player in the integration of GABAergic medium spiny neurons in response to dopamine and glutamate (Fernandez et al., 2006).

Histological and immunohistochemical analyses revealed that hIDPSCs were able to cross the blood-brain barrier and reach different areas affected by HD, including the striatum and cortex. Morphometric histological analysis revealed that most hIDPSC-treated animals showed mild neuron loss in the striatum compared to untreated animals (3-NP +saline). Moreover, hIDPSCs showed neuroprotective and neuroreparative effects, as revealed by the upregulation of BDNF, DARPP32, and D2 receptor expression, which are down-regulated in Huntington's disease (Van Dellen et al., 2000; Crook and Housman, 2012).

The primary study assessing safety of hIDPSC was the 3-nitropropionic acid (3-NP) rat model of HD study. In this study, two different cell doses were injected: $1 \times 10^6$ and $1 \times 10^7$ cell/transplant or $3 \times 106$ cell/kg and $3 \times 107$ cell/kg, respectively. 3-NP-treated rats received a single IV injection or a total of three IV injections at one month intervals of the cells. Seven deaths occurred in 3-NP induced animals which received $3 \times 106$ cell/kg, and 5 deaths occurred in animals receiving $3 \times 107$ cell/kg. In placebo groups (3-NP induced without the cell transplantation) same number (12) of animals died. All rats that died presented with extremely severe disease manifestation; the deaths occurred within 5 days of 3-NP administration. No additional deaths occurred with repeated hIDPSC doses. Based on these data, probable cause of all early deaths was 3-NP toxicity. Because no deaths occurred after repetitive hIDPSC transplantation, this supports the safety of hIDPSC transplantation (Table 15).

Figure 24:
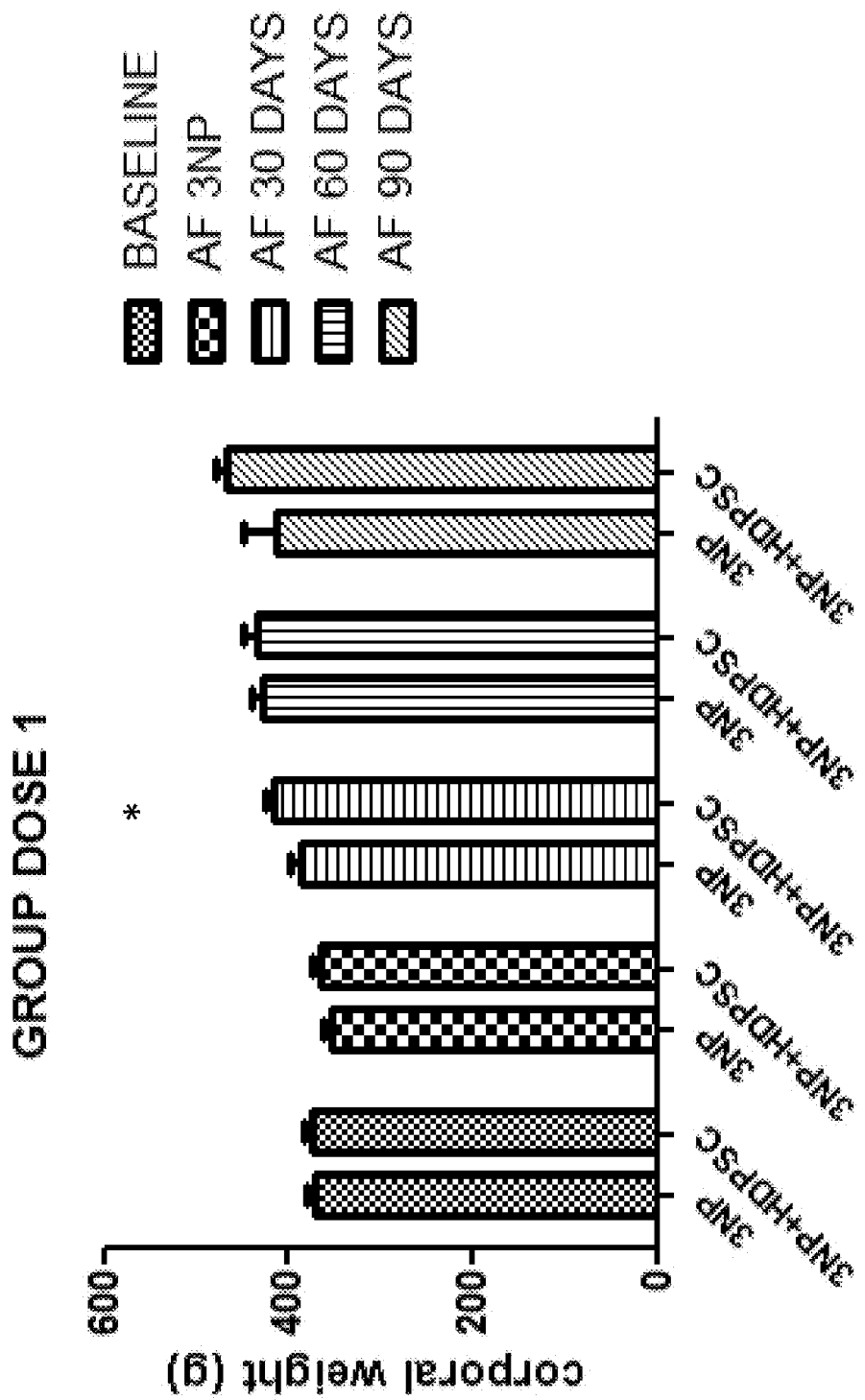
FIG. 24 depicts the effect of hIDPSC administration on body weight in treated (3-NP+hIDPSC) and untreated animals (3-NP+Saline). Body weight was recorded before and 4 days after 3-NP administration and after each hIDPSC administration (every 30 days). No increase in body weight was observed in 3-NP-treated animals 30, 60, and 90 days after 3-NP administration. Body weight in hIDPSC-treated animals ($1\times10^6$ dose) increased after the first hIDPSC administration.

Patients with Huntington's disease often exhibit progressive weight loss despite adequate or high-energy intake. Weight loss may be an indicator of 3-NP neurotoxicity caused by decreased energy metabolism (Saydoff et al., 2003; Colle et al., 2013). No significant weight loss was observed in 3-NP-treated animals four days after 3-NP administration. However 30 days after hDPSC transplant, the hDPSC group ($1 \times 10^6$ cells dose) exhibited significantly weight gain when compared with untreated group (3NP). Thus, hIDPSC attenuated weight loss (p=0.01) (FIG. 24).

HD is a clinically debilitating disease for which there is no available therapy to stop or reverse disease progression. One major obstacle encountered by many therapeutics to treat HD, is that it is a neurodegenerative disorder and some targeted systemically delivered drugs would be unable to reach their target; passage of drugs to the brain is regulated by the blood-brain barrier (BBB). The BBB is a highly selective permeability barrier that separates the circulating blood from the extracellular fluid surrounding the nervous system. Treatment with cell-based therapeutics, therefore, would seem to require localized delivery bypassing the BBB (i.e. injection through the selective permeability barrier) since cells do not generally cross the BBB.

Extensive studies show that hIDPSCs have mesenchymal stem cell (MSC) attributes, can secrete immunomodulating and neurotropic factors. In addition, histological and immunohistochemical analyses in validated HD rat model reveal that hIDPSCs are able to cross the BBB and reach different areas affected by HD, including the striatum and cortex.

Morphometric histological analysis reveals that most hIDPSC-treated animals show mild neuron loss in the striatum compared to untreated animals. Moreover, hIDPSCs show neuroprotective and neuroreparative effects by upregulating BDNF, DARPP32, and D2 receptor expression, which are downregulated in Huntington's disease (Van Dellen et al., 2000; Crook and Housman, 2012).

Finally, studies evaluating the safety profile of hIPDSCs show they do not form teratomas, they do not exhibit chromosomal aberration, and they are able to form human/mouse chimeras. Since the studies suggest hIPDSCs are safe and efficacious in the treatment of HD, we propose to use hIDPSCs to treat HD.

Example 7

Preclinical Pharmacology Studies

FIG. 28 summarizes the preclinical pharmacology studies, which aimed at examining the different clinical applications of the investigational product CELLAVITA™ (stem cells). Although many of the studies were conducted to investigate pharmacological efficacy for various indications, they are all supportive to demonstrate the safety profile of the product as well as for the proposed intravenous route of administration.

Example 8

Figure 25:
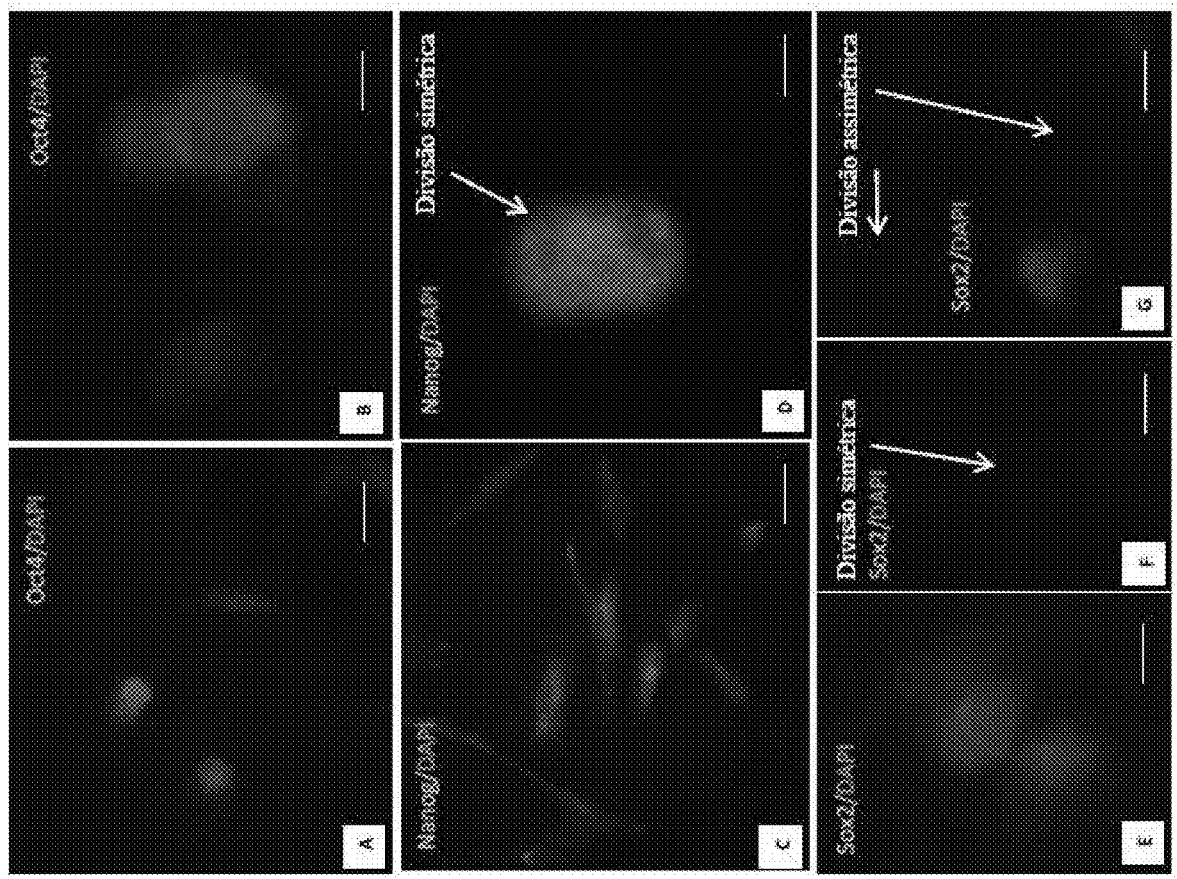
FIG. 25 depicts intracellular expression of Oct4, Nanog, and Sox2. Nuclei were stained with DAPI.

Identification of the Parameters for Safe Systemic Administration of a Stem Cell Treatment IDPSC shows Oct4 nuclear localization (FIG. 25). While a majority of IDPSCs have Nanog in the cytoplasm of cells (FIG. 25), very rarely do cells demonstrate nuclear localization as well. The intracellular localization of Sox2 in IDPSCs is mainly nuclear (FIG. 25) though several cells can show cytoplasmic localization too. Interestingly, we can observe the symmetrical division when Nanog and Sox2 expression in seen in both daughter cells, and observe asymmetric division when after division the daughter cells do not express these markers or loses the characteristic of stem cells and becomes a less potent progenitor or a differentiated cell (FIG. 25).

Our data demonstrate that in contrast to pluripotent stem cells, IDPSC are classified as MSC or adult stem cells. The intracellular localization of Nanog indicates that the protein is mostly inactive. This is a dramatic difference between pluripotent stem cells and adult stem cells, which express pluripotent stem cells markers. These cells are more immature than classic MSC and can differentiate to wider spectrum of the mature cells, but they are not able to produce teratoma due to the inactive state of Nanog. Our data on symmetric and asymmetric division clearly demonstrate that these cells mimic asymmetric neural stem cells division (FIG. 25).

Example 9

In Vivo Tumorigenicity

Teratomas formation is an essential tool in determining the pluripotency of any pluripotent cells, such as embryonic or induced pluripotent stem cells (ES and iPS cells). Established a consistent protocol for assessment of teratoma forming ability of the cells, was used in our studies, similar to protocol published recently by Gropp et al., 2012. Our and recently published methods are based on subcutaneous co-transplantation of defined numbers of undifferentiated mouse or human ES and iPS cells and Matrigel into immunodeficient mice. Our method was shown to be highly reproducible and efficient when $10^6$ cells (different from Gropp et al., 2012, which used $10^5$ cells) of mouse ES cells and human iPS cells were used. In 100% of cases we observed teratoma formation in a large number of animals and in long follow-up (up to 6 months). We also used these methods for bio-safety analysis of other adult MSC, such as those derived from dental pulp of deciduous teeth, umbilical cord, and adipose tissue.

We observed derivation of induced pluripotent stem cells from hIDPSC. The pluripotency of hIDPSC derived iPS cells were tested through teratoma formation, while human embryonic stem (ES) cells and hIDPSC were used as control. Routine protocol for teratomas production for ES cells was used (Hentze et al., 2009). Following this protocol $10^6$ of cells of each line: hIDPSC-iPS cells, ES cells and hIDPSC were inoculated in the rear leg muscle of 4-week-old male, SCID. In animals, which were inoculated with hIDPSC-iPS cells or ES cells teratoma formation was observed after three months. However, hIDPSCs, which were used as a negative control in this study and were inoculated in 10 animals, did not produce teratomas neither after three month nor after six months of follow-up. Five of these animals were maintained alive during one year and even after this time teratomas formation was not observed.

Histologically, teratoma formation in pluripotent stem cells requires the development of tissues derived from the three germ layers. For adult/mesenchymal stem cells, any alterations in the integrity of normal tissue at the site of transplantation were considered. After six months, animals, which were inoculated with hIDPSCs and did not produce teratomas, were killed and histological specimens of the brain, lung, kidney, spleen, and liver were analyzed of the animals. The presence of DNA from hIDPSCs was confirmed in all aforementioned organs but no tumor formation or any morphological alterations were observed. Thus, we established the safety of cell regeneration by investigational product CELLAVITA™ (stem cells) regarding tumor formation and risk of immune rejection.

Additionally, as shown in the aforementioned studies using hIDPSC in animal models of spinal cord injury, cranial bone defects, total limbal stem cell deficiency (TLSCD), muscular dystrophy, and osteonecrosis of the femoral head (ONFH), no teratoma formation and/or risk of immune rejection were observed (Costa et. al., 2008; Kerkis et al., 2008; Monteiro et al., 2009; Gomes et al., 2010; Feitosa et al., 2010; Almeida et al., 2011).

FIG. 29 summarizes additional already published preclinical studies, which support the safety of investigational product CELLAVITA™ (stem cells).

Example 10

Principal Criterion for Teratoma Assay

We evaluated the next criterion for a teratoma assay: sensitivity and quantitatively; definitive cell number and single cell suspension production; immunophenotyping of studied cell in respect of expression on pluripotent cell markers and karyotype; co-transplantation of studied cells together with Matrigel. The cells were transplanted subcutaneously (s.c) into NOD/SCID mice, which allows for simple monitoring of teratoma development.

The development of tumors was monitored from 4 month (~16 weeks). Histological criteria for teratomas is the differentiation of pluripotent cells into the cells derived from three germ layers. Such study usually was performed by pathologist.

For adult/mesenchymal stem cells any type or any changes on normal tissue integrity in the site of cell injection were taken in consideration.

Application of the Teratoma Criterion

A. The Experimental System(s):
a. Mouse embryonic stem cells
b. Mouse 3T3 fibroblasts, permanent mouse cell line Balbc 3T3 cell line, clone A31
c. Human iPS-IDPSC
d. Human ES cells
e. Human IDPSCs We used aforementioned method in diverse studies to characterize different mouse ES cell lines pluripotency established by us as well as to confirm ES cells pluripotency at high 25 or more passages and for characterization of sub-clones obtained from mouse ES cell lines (Sukoyan et al., 2002; Carta et al., 2006; Kerkis et al., 2007; Lavagnolli et al., 2007; Hayshi et al., 2010).

Additionally, this method was used to characterize the pluripotency of iPS cells derived from immature dental pulp stem cells (IDPSC) in more recent publication of our group (Beltrão-Braga et al., 2011). In this publication the human IDPSC were used as a control for iPS-IDPSCs. We showed that iPS-IDPSCs formed nice teratomas with tissues originated from all three germ layers, while hIDPSC were not able to produce any type of teratomas or any other type of neoplasms. In addition, iPS-IDPSCs expressed Nanog in nucleus, and hIDPSCs did not.

Results

Disclosed multiharvest explant like culture used for the isolation of a population of immature dental pulp stem cells (IDPSC), results in expression of embryonic stem cell markers Oct-4, Nanog, SSEA-3, SSEA-4, TRA-1-60 and TRA-1-81 as well as several mesenchymal stem cell markers during at least 15 passages while maintaining the normal karyotype and the rate of expansion characteristic of stem cells. The expression of these markers was maintained in subclones obtained from these cells. Moreover, in vitro these cells can be induced to undergo uniform differentiation into smooth and skeletal muscles, neurons, cartilage, and bone under chemically defined culture conditions. It is important to mentioned that IDPSC although have a small size and cytoplasm poor in cell organelles differ from naïve pluripotent cells presenting typical mesenchymal—fibroblast like morphology. Therefore IDPSC are of mesenchymal type, in contrast to ES and iPS cells, which are of epithelial type. The principle difference between MSC and ES or iPS cells that MSC are migrating and plastic anchoring, they synthetize extracellular matrix and are cell junction free cells.

B. The Experimental System(s):
a. IDPSC three different primary cultures at early (n=10) and late passages (n=10)
b. Human primary fibroblast In addition, this method was validated using dog fetal stem cells from bone marrow, liver, yolk sac, allantois and amniotic liquid which also express pluripotent markers.

The IDPSC are composed by population of MSC with a variable number of stem cells expressing pluripotent markers (1-25% of cells) (Lizier et al., 2012). These cells were transplanted into NOD/SCID mice (n=20) and the development of tumors was monitored from 4 month (~16 weeks). Any type of changes on normal tissue integrity in the site of cell injection were taken in consideration. This protocol was adapted for population of IDPSC, especially in respect of cell number used, which was calculated on the basis that 20% of IDPSC express pluripotent markers. In our previous tests with ES and iPS cells we used $10^6$ cells, while in to test IDPSC and control cells teratogenicity $5 \times 10^6$ cells were used. After 4 month, even if macroscopically the tumors were not observed, the mice were sacrificed and frozen cuts were obtained from diverse organs, such as brain, lung, kidney, spleen, liver and were analyzed by pathologist.

Although presence of DNA of IDPSC within all studied organs were found, no tumor formation or any morphological changes were observed.

Example 11

Cell Culture Conditions to Establish Proper Population of Stem Cells

Culture conditions, such as culture medium and adhesive surface, can affect gene expression of the cells. Such genes include ABCG2 and Vimentin, which are two genes that can indicate suitability of the cells in culture for therapeutic use, particularly systemic cellular systems like the present invention. Most suitable culture medium form tested is DMEM/F12 basal medium supplemented with 5-10-15% of FBS, antibiotics, and Glutamate, and the cells should be cultured without an adhesion layer (e.g. without extracellular matrix (ECM) or scaffold) such that the cells adhere directly to the culture dish or beads plastic. Cells that were grown with epithelial growth media conditions turn into epithelial-like cells. Using various xeno-free medium will require growth factors supplementation and selection of appropriate ECM coating can be useful for scale up of current cells into 3D culture conditions including bioreactors, such as Terumo hollofiber bioreactor, Eppendorf—New Brunswick bioreactors with beads, etc.

Figure 26:
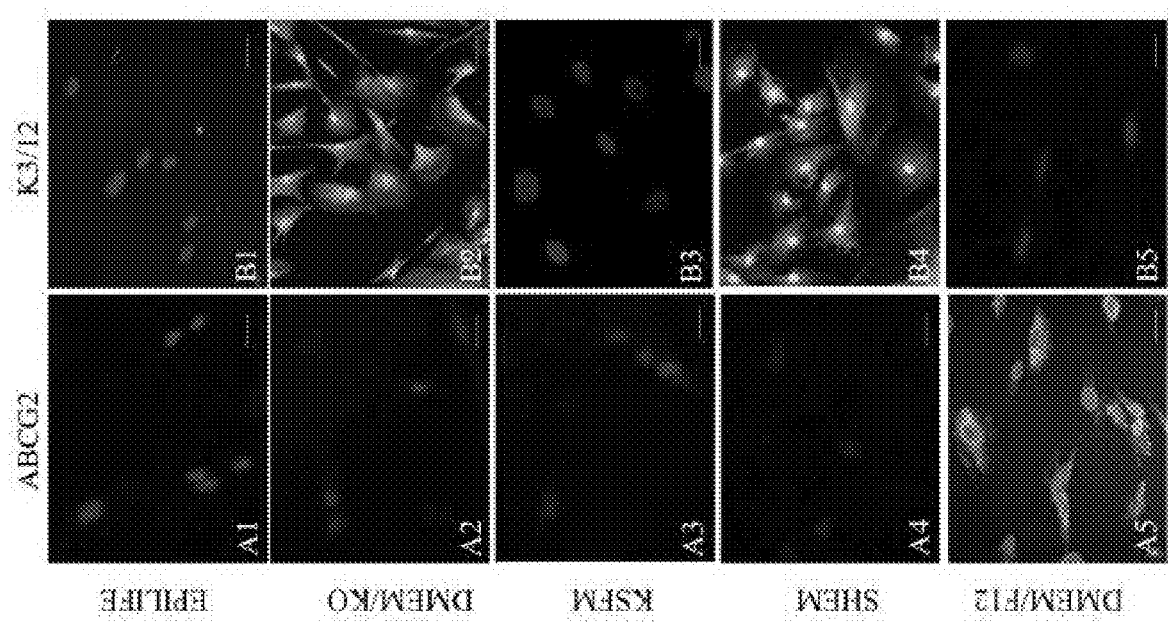
FIG. 26 depicts expression of ABCG2 and K3/12 in IDPSC grown on various types of cell culture media.
Figure 27:
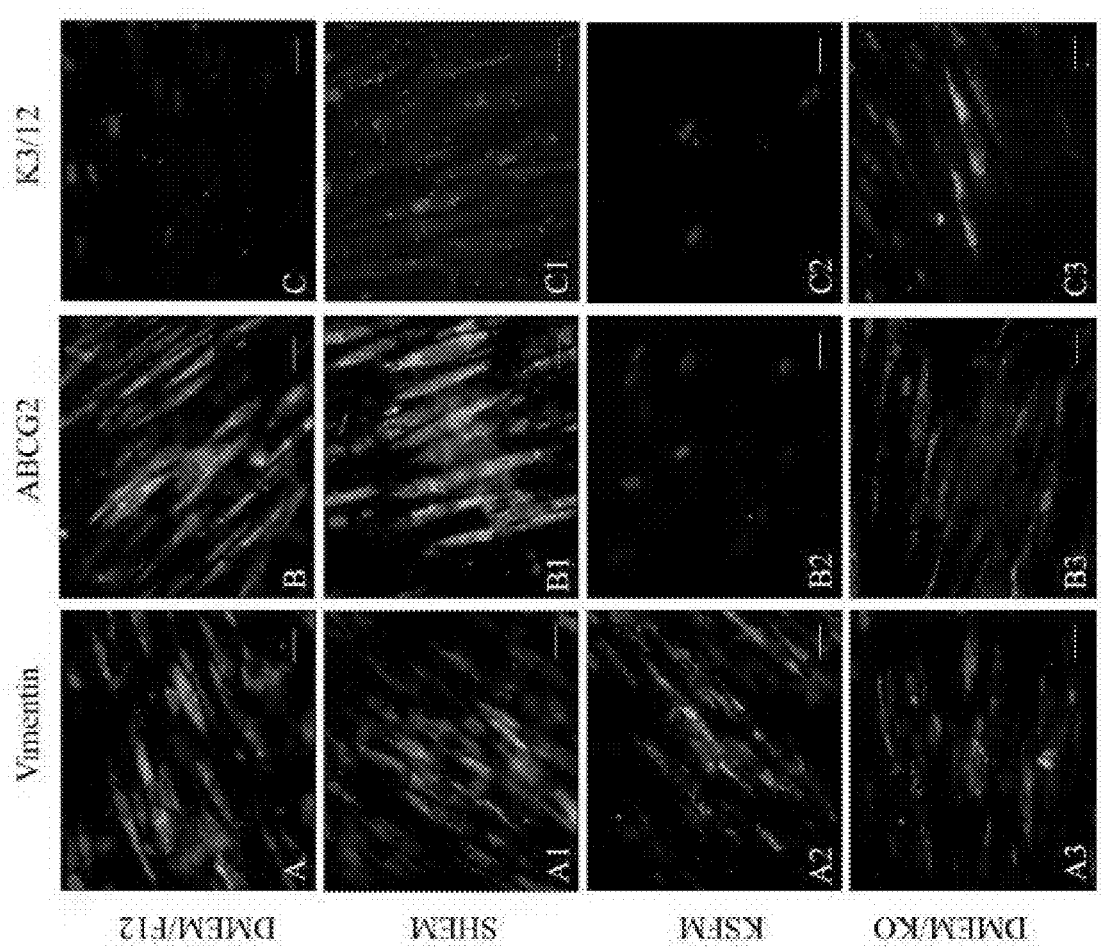
FIG. 27 depicts expression of Vimentin, ABCG2, and K3/12 in IDPSC grown on various types of cell culture media.

The link of ABCG2 expression and undifferentiation status of cells is shown on FIGS. 26 and 27 where we demonstrated that once ABCG2 is not expressed due to changed culture medium or coating layer, then cells have clearly a more fibroblast or epithelial cells-like morphology. Another surprising finding was that a typical medium routinely used in the prior art for maintenance or induction of embryonic stem cells, namely Dulbeccos Modified Eagle Medium (DMEM) serum knockout medium KOSR (KSFM), is not advantageous for generating or maintaining pluripotent cells derived from hDPSC. As demonstrated in FIG. 26, use of this medium with and without fibronectin containing scaffold/ECM matrix coating or scaffold resulted in the differentiation of hIDPSCs into fibroblast-like or epithelial like cells (FIG. 26). In contrast to the use of Dulbeccos Modified Eagle Medium (DMEM) alone, it was found that Dulbeccos Modified Eagle Medium (DMEM) or Neurobasal medium (NB) if supplemented with B27 and, optionally, supplemented with FGF and/or EGF, leads to the formation of neuronal like leneages. Exemplary protocols for differentiation into cells of the neural lineages have also been described in previous patent applications, for example, International Application no. PCT/IB14/59850 and U.S. patent application Ser. No. 14/214,016.

Differentiation into Corneal Cells
Material and Methods
De-Epithelialization of Amniotic Membrane as a Potential Fibronectin-Containing Scaffold for hIDPSC Cell Culture Amniotic membrane (AM) was obtained from placenta of donor and stored at −8° C. (Covre J L at al 2011). Prior AM use, it was thawed at room temperature and washed in three times in PBS. Next, AM was removed from nitrocellulose membrane and washed again. In order to remove the epithelia, AM was incubated with EDTA for two hours. Then, the epithelia were removed mechanically. The AM becomes transparent following the epithelia removal. Completely transparent AM was transferred on inserts (Covre J L at al 2011 and Melo G B at al 2007).

IDPSC Culture

Human IDPSC, (2n=46, XX) were isolated from dental pulp of deciduous teeth and characterized previously (Kerkis et al. 2006). hIDPSC were maintained in Dulbecco's-modified Eagle's medium (DMEM)/Ham's F12 (1:1; Invitrogen, Carls-bad, Calif.), supplemented with 15% fetal bovine serum (FBS; Hyclone, Logan, Utah), 100 units/mL penicillin (Gibco, Grand Island, N.Y.), 100 µg/mL streptomycin (Gibco), 2 mM L-glutamine (Gibco), and 2 mM nonessential amino acids (Gibco). The culture medium was changed daily, and the cells were replaced every 3 days. After they reached 80% confluence, they were washed twice in sterile phosphate-buffered saline (PBS; Gibco; 0.01 M, pH 7.4), enzymatically treated with 0.25% trypsin/EDTA (Invitrogen), and seeded onto amniotic membrane previously prepared.

Culture Media

To select the best culture media for cultivate IDPSC on AM, we tested the following culture media: A) The first was supplemental hormonal epithelial medium (SHEM), a combination of Dulbecco's Modified Eagle's Medium/Ham's F-12 nutrient mixture (DMEM/F12; Invitrogen, Gibco Cell Culture, Port-land, Oreg.; 1:1) containing 1.05 mM calcium supplemented with 5 µg/ml crystalline bovine insulin (Sigma Aldrich, St. Louis, Mo.), 30 ng/ml cholera-toxin (Calbiochem, San Diego, Calif.), 2 ng/ml epidermal growth factor (EGF, R & D Systems, Inc., Minneapolis, Minn.), 0.5% dimethyl sulfoxide (DMSO, Sigma Aldrich), 0.5 µg/ml hydrocortisone, 5 ng/ml sodium selenite, and 5 µg/ml apo-transferrin, and supplemented with 10% fetal bovine serum (FBS). All reagents were obtained from Invitrogen Corporation (Grand Island, N.Y.), except those indicated in the text. B) The second was keratinocyte serum-free medium (KSFM) containing 0.09 mM calcium supplemented with 30 mg/ml pituitary bovine extract, 0.2 ng/ml EGF, 10% FBS, and ampicillin/streptomycin. C) The third was Epilife medium (Cascade Biologics, Portland, Oreg.), containing 0.06 mM calcium supplemented with 1% "human corneal growth supplement" (Cascade Biologics), containing 0.2% pituitary bovine extract, 5 g/ml bovine insulin, 0.18 mg/ml hydrocortisone, 5 µg/ml bovine transferrin, 0.2 ng/ml EGF, added 1% penicillin G sodium (Penicillin G sodium 10,000 g/ml, streptomycin sulfate 25 mg/ml, amphotericin B in 0.85% NaCl), and 5% FBS. D) Knockout media Antibodies Mouse anti-human monoclonal antibodies: ABCG2 (Chemicon) and cytoplasmic/nuclear monoclonal antibodies: mouse anti-cytokeratin 3/12 (K3/12) (RDI, Flanders, N.J., USA), reacts with human and rabbit. Mouse anti-human IDPSC antibody was obtained as described (Kerkis et al., 2006) and successfully used by us in previous studies (Fonseca et al., 2009; Monteiro et al., 2009).

Immunofluorescence Staining

Cells were grown on glass cover-slips up to 70% confluence and also, were grown on AM, washed in PBS (Gibco) and fixed overnight with 4% paraformaldehyde (Sigma). Coverslips were washed three times in tris buffered saline (TBS), containing 20 mm Tris-HCl pH 7.4 (Vetec, Duque de Caxias, RJ, Brazil), 0.15 m NaCl (Dinâmica Reagent, Sao Paulo, SP, Brazil), and 0.05% Tween-20 (Sigma). Permeabilization was performed using 0.1% Triton X-100 for 15 min (Santa Cruz Biotechnology). Cells were washed three times and incu-bated for 30 min in 5% bovine serum albumin (Sigma) in PBS pH 7.4 (Gibco). Primary antibodies were added for 1 h on each slide at different dilutions (ABCG2 and K3/12 (1:100), and anti-hIDPSC (1:1000)), which were incubated at room temperature. Following washing in TBS (three times), cells were incubated in the dark for 1 h with secondary anti-mouse antibody-conjugated fluorescein isothiocyanate (FITC) at a dilution of 1:500. Microscope slides were mounted in antifade solution (Vectashield mounting medium, Vector Laboratories, Hercules, Calif., USA) with 4',6-diamidino-2-phenylindole (DAPI) and analysed using a confocal microscope. Control reactions were incubated with PBS instead of primary antibody, followed by washing and incubation with respective secondary antibody. All experiments have been done in triplicate.

Results

Figure 5:
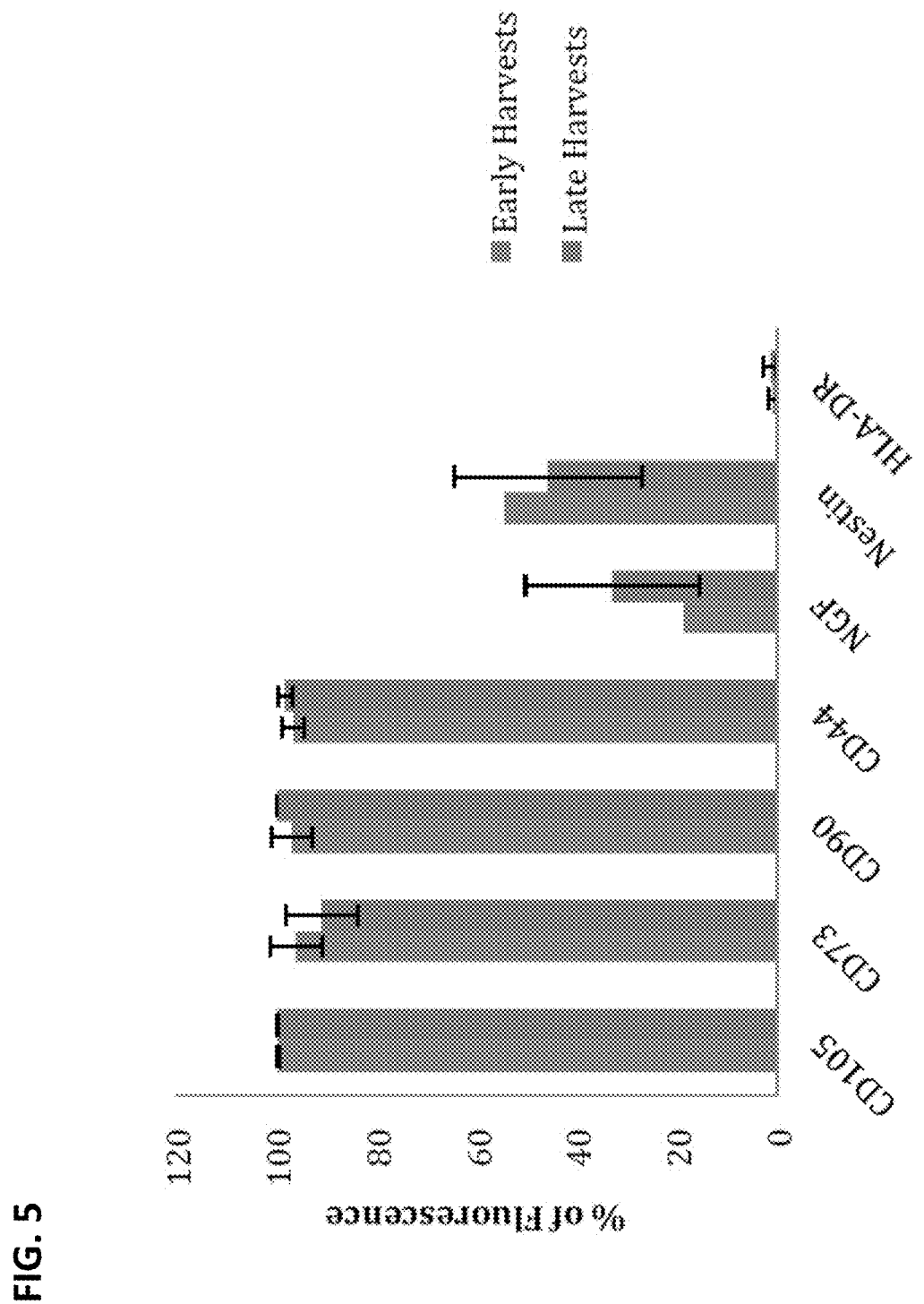
FIG. 5 depicts immunophenotyping of hIDPSC from early and late harvests. Harvests 0-10 were defined as early harvests. All harvests after 10 were defined as late harvests.
Figure 6:
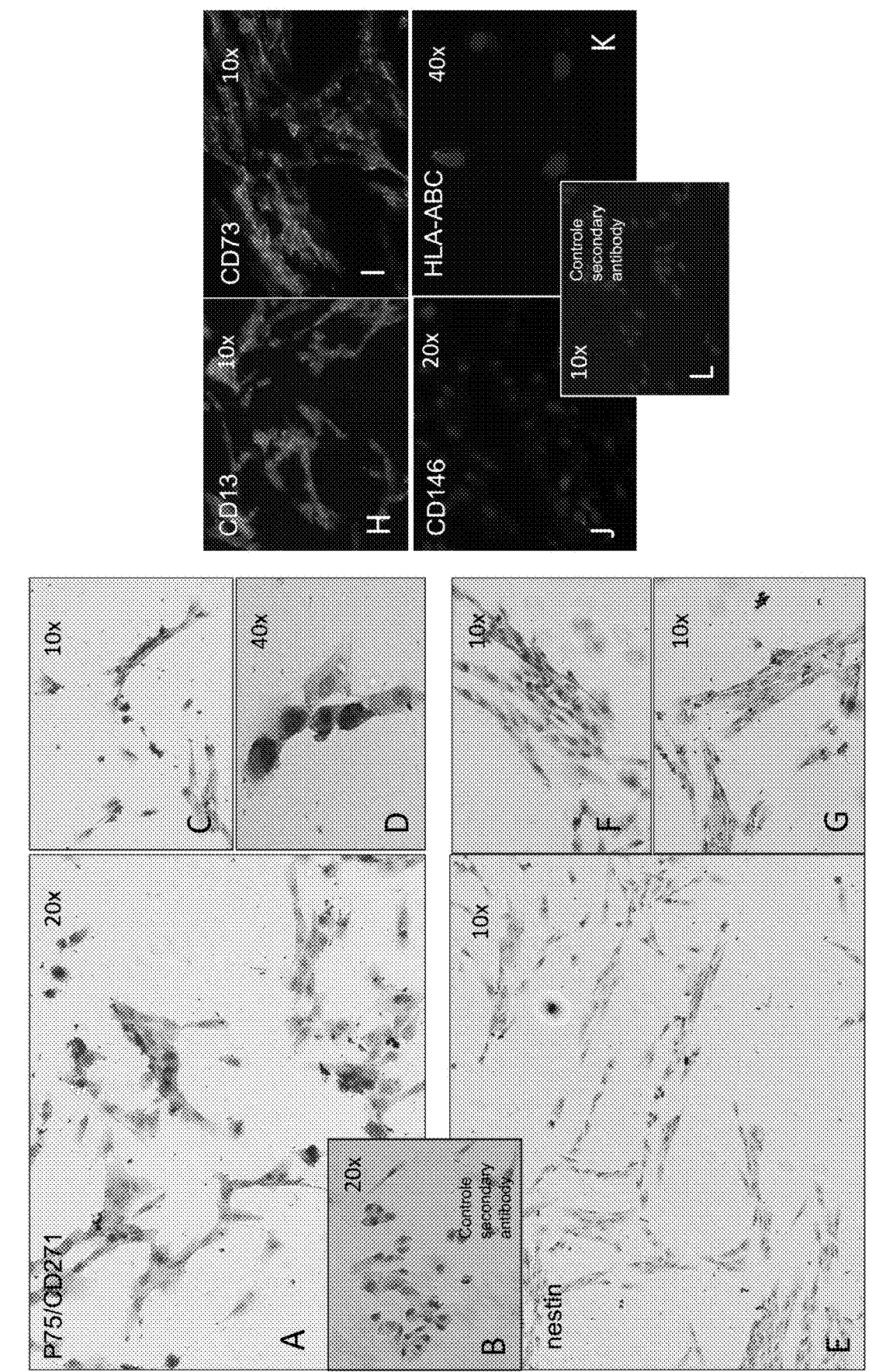
FIG. 6 depicts IDPSC at late harvest (13) at passage 3 were immunopositive for P75 (CD271) (A, C, D), nestin (E-G), CD13 (H) and CD73 (I), and they did not react with CD146 (J) and HLA-ABC (K). Insets, demonstrate control for respective secondary antibodies. A-G Light Microscopy. H-L Epi-Fluorescence. Magnification: A,J-20×; C,E-G,H,I, L-10×; D,K-40×

Expression of Undifferentiated LSCs and Differentiated Corneal Cells Proteins in IDPSCs Grown in Different Culture Media on Plastic Substrate The expression pattern of ABCG2 protein (ATP-binding cassette sub-family G member 2), which are commonly used for LSCs characterization and CK3 (cytokeratin 3) and cytokeratin 12 that encodes the type I intermediate filament chain and both expressed in corneal epithelia were analyzed. FIG. 26 depicts that IDPSC had differential response in respect of expression of studied proteins when cultured in distinct culture medium during 7 days. The IDPSCs grown on plastic surfaces did not express ABCG2 when cultured in SHEM, KSFM, Epilife and DMEM/KO (FIG. 26), this protein was expressed in IDPSCs only when they were cultured in basal culture medium (FIG. 22A5). Interestingly, that IDPSCs cultured in SHEM and DMEM/KO, after seven days changed their morphology fibroblast like (FIG. 26) to epithelial like (FIG. 26) and start to express CK3/12, while IDPSC cultured in Epilife and KSFM and DMEM/F12 did not start to express K3/12 (FIG. 26).

Expression of Undifferentiated LSCS and Differentiated Vimentin Markers in IDPSCs Grown in Different Culture Media on AM Next, the expression of these markers and additionally vimentin was verified in IDPSC grown on AM during 7 days (FIG. 27). Epilife was excluded from this study due to very low survival of the cells (less then 50%), when grown in this medium and low adherence of the cells on AM in combination with Epilife. Vimentin expression was observed in all samples (FIG. 27), it was positive in IDPSCs cultured in DMEM/F12 and SHEM (FIG. 27) and showed weak positivity with IDPSCs cultured in KSFM and DMEM/KO (FIG. 27). ABCG2 antibody showed strong immunopositivity with IDPSC cultured in SHEM and DMEM/F12 (FIG. 27) and did not express in IDPSC cultured in KSFM (FIG. 27) and showed weak immunoreactivity with IDPSC cultured in DMEM/KO (FIG. 27). IDPSCs did not react with IDPSCs cultured in DMEM/F12 e KSFM (FIG. 27) and showed very weak immunopositivity with K3/12 when cultured in SHEM and DMEM/KO (FIG. 27).

Example 12

Expression of CD146 and CD13 in Early Phase (EP) and Late Phase (LP) hIDPSC

Figure 30:
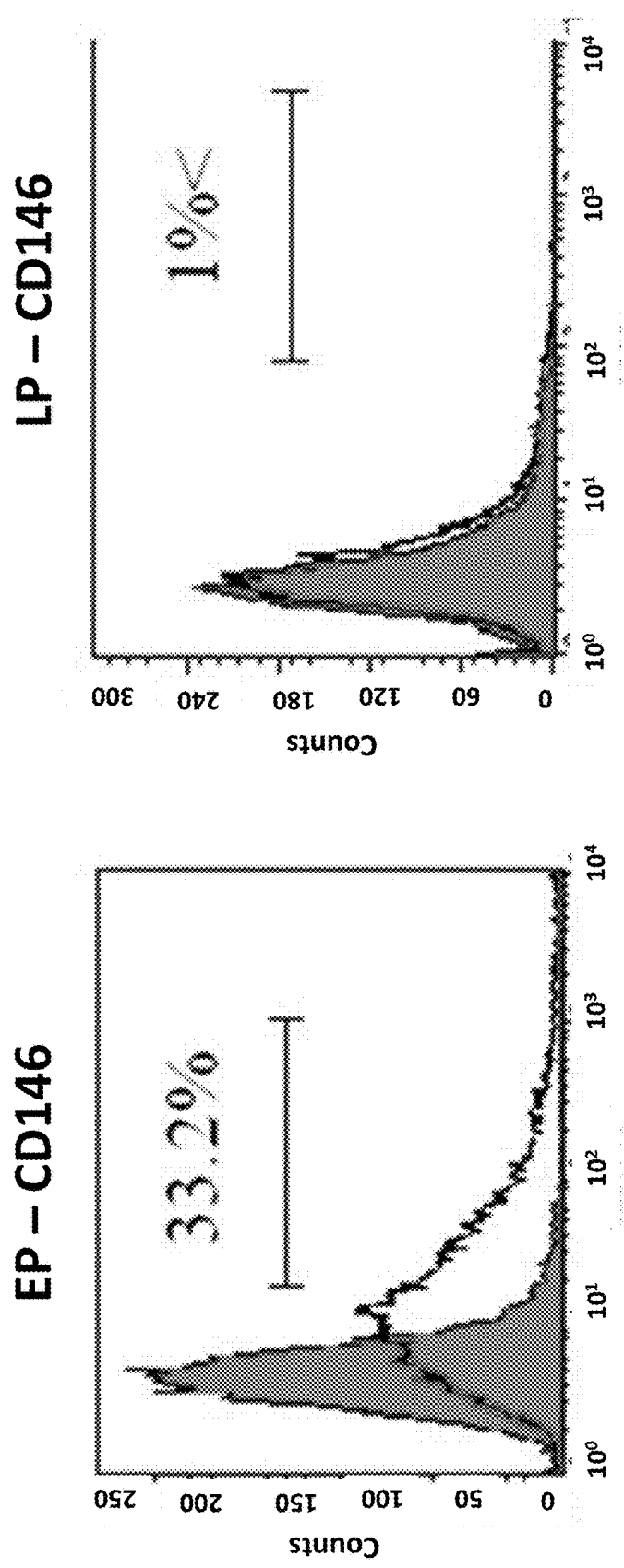
FIG. 30 depicts a flow cytometry analysis of early phase (EP) and late phase (LP) hIDPSC. Changes in CD146 and CD13 expression were observed following in vitro DP harvesting and hIDPSC passing. For EP-hIDPSC ~33% of CD146 positive cells were observed, while for LP-hIDPSC less than 1% of the cells were positive for this marker. For EP-hIDPSC ~52% of CD13 positive cells were observed, while for LP-hIDPSC 95% of the cells were positive for this marker.
Figure 30:
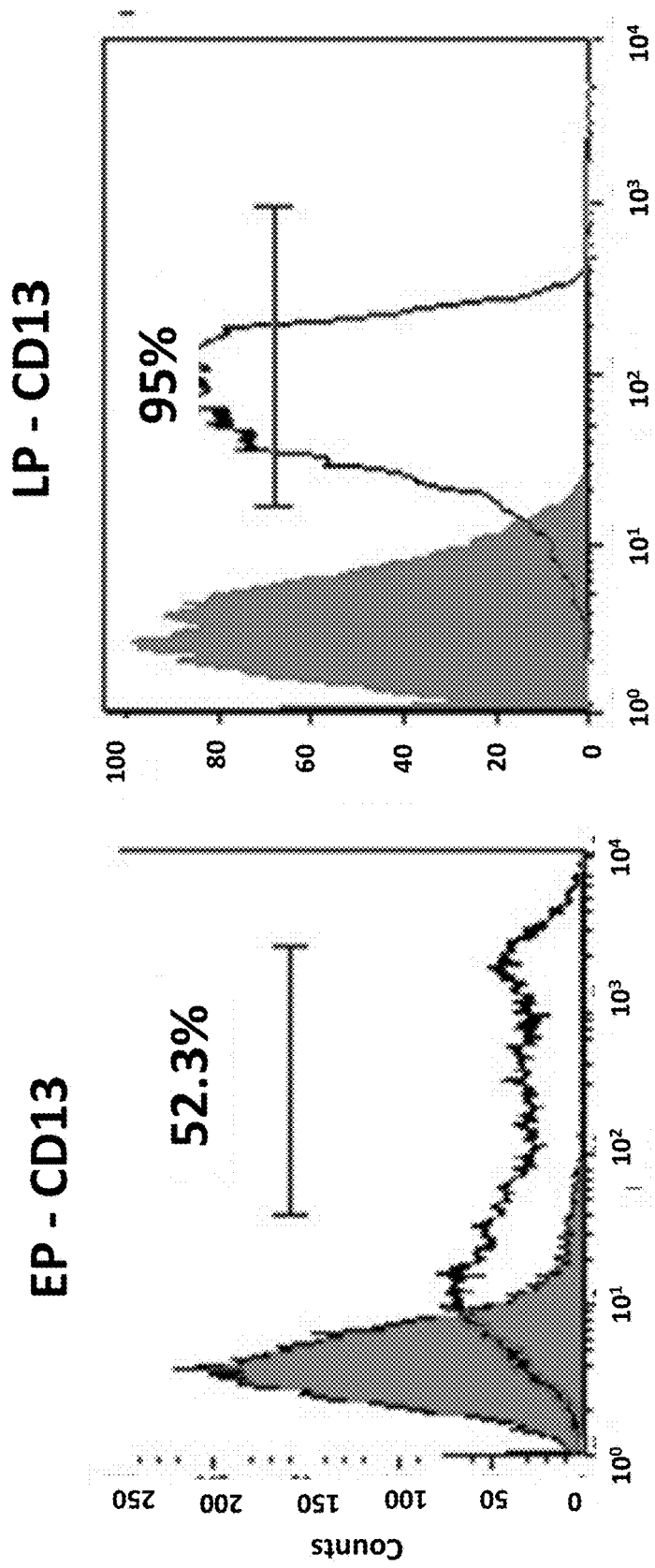

CD146 and CD13 expression were analyzed by flow cytometry in EP-hIDPSC and LP-hIDPSC. The results in FIG. 30 show that CD13 was expressed in 52% of EP-hIDPSC and 95% of LP-hIDPSC. These results demonstrate that in vitro DP harvesting and hIDPSC passing produce increased quantities of hIDPSC expressing CD13 and lacking expression of CD146.

REFERENCES

1. Altman J and Das G D. Post-natal origin of microneurones in the rat brain. Nature 1965; 207: 953-956
2. Bachoud-Levi A C, Gaura V, Brugieres P, et al. Effect of fetal neural transplants in patients with Huntington's disease 6 years after surgery: a long-term follow-up study. Lancet Neurol 2006; 5: 303-09.
3. Baker S A, Baker K A and Hagg T. Dopaminergic nigrostriatal projections regulate neural precursor proliferation in the adult mouse subventricular zone. Eur J Neurosci 2004; 20: 575-579
4. Brito et al., Imbalance of p75NTR/TrkB protein expression in Huntington's disease: implication for neuroprotective therapies. Cell Death and Disease (2013) 4, e595; doi:10.1038/cddis.2013.116
5. Lescaudron L, Unni D, Dunbar G L. Autologous adult bone marrow stem cell transplantation in an animal model of huntington's disease: behavioral and morphological outcomes. Int J Neurosci 2003; 113:945-956.
6. Vatzey E M, Chen K, Hughes S M, Connor B: Transplanted adult neural progenitor cells survive, differentiate and reduce motor function impairment in a rodent model of Huntington's disease. Exp Neurol 2006; 199:384-396.
7. C. Uboldi, A. Doring, C. Alt, P. Estess, M. Siegelman, and B. Engelhardt, "L-Selectin-deficient SJL and C57BL/6 mice are not resistant to experimental autoimmune encephalomyelitis," European Journal of Immunology, vol. 38, no. 8, pp. 2156-2167, 2008.
8. B. Engelhardt, "Immune cell entry into the central nervous system: involvement of adhesion molecules and chemokines," Journal of the Neurological Sciences, vol. 274, no. 1-2, pp. 23-26, 2008.
9. S. Kim, K. A. Chang, J. Kim et al., "The preventive and therapeutic effects of intravenous human adipose-derived stem cells in Alzheimer's disease mice," PLoS ONE, vol. 7, no. 9, Article ID e45757, 2012.
10. D. Jeon, K. Chu, S. Lee et al., "A cell-free extract from human adipose stemcells protects mice against epilepsy," Epilepsia, vol. 52, no. 9, pp. 1617-1626, 2011.
11. Mullen R J1, Buck C R, Smith A M. NeuN, a neuronal specific nuclear protein in vertebrates. Development. 1992 September; 116(1):201-11.
12. Shuo Liu, Dritan Agalliu, Chuanhui Yu and Mark Fisher. The Role of Pericytes in Blood-Brain Barrier Function and Stroke. Current Pharmaceutical Design, 2012, 18, 3653-3662.
13. De Miguel M P, Fuentes-Julian S, Blazquez-Martinez A, Pascual C Y, Aller M A, Arias J, Arnalich-Montiel F. Immunosuppressive properties of mesenchymal stem cells: advances and applications. Curr Mol Med. 2012 June; 12(5):574-91.
14. Le Blanc K, Ringden O. Mesenchymal stem cells: properties and role in clinical bone marrow transplantation. Curr Opin Immunol. 2006 October; 18(5):586-91. Epub 2006 Aug. 1.
15. Karen English Mechanisms of mesenchymal stromal cell immunomodulation. Immunol Cell Biol 91: 19-26; advance online publication, Oct. 23, 2012; doi:10.1038/icb.2012.56
16. Matthew D Griffin, Aideen E Ryan, Senthilkumar Alagesan, Paul Lohan, Oliver Treacy and Thomas Ritter Anti-donor immune responses elicited by allogeneic mesenchymal stem cells: what have we learned so far? Immunol Cell Biol 91: 40-51; advance online publication, Dec. 4, 2012; doi:10.1038/icb.2012.67
17. Svenningsson P, Nishi A, Fisone G, Girault J A, Nairn A C, Greengard P. DARPP-32: an integrator of neurotransmission. Annu Rev Pharmacol Toxicol. 2004; 44:269-96.
18. Crook Z R, Housman D E. Dysregulation of dopamine receptor D2 as a sensitive measure for Huntington disease pathology in model mice. Proc Natl Acad Sci USA. 2012 May 8; 109(19):7487-92. doi: 10.1073/pnas.1204542109. Epub 2012 Apr. 23.
19. Chen J Y, Wang E A, Cepeda C, Levine M S. Dopamine imbalance in Huntington's disease: a mechanism for the lack of behavioral flexibility. Front Neurosci. 2013 Jul. 4; 7:114. doi: 10.3389/fnins.2013.00114. eCollection 2013.
20. Parent M, Bedard C, Pourcher E. Am J Neurodegener Dis. 2013 Sep. 18; 2(3):221-7.
21. Hoglinger G U, Rizk P, Muriel M P, Duyckaerts C, Oertel W H, Caille I and Hirsch E C. Nat Neurosci 2004; 7: 726-735).
22. Wernig M, et al. Proc Natl Acad Sci USA. 2008; 105:5856-5861; Caiazzo M, et al. Nature. 2011; 476:224-227;
23. Lindvall, O. & Kokaia, Z., J Clin Invest., 2010 120, 29.
24. Calissano P, Matrone C, Amadoro G: Nerve growth factor as a paradigm of neurotrophins related to Alzheimer's disease. Dev Neurobiol 2010, 70:372-383.
25. M, Togari A, Kondo T, Mizuno Y, Komure O, Kuno S, Ichinose H, Nagatsu T: Brain-derived growth factor and nerve growth factor concentrations are decreased in the substantia nigra in Parkinson's disease. Neurosci Lett 1999, 270:45-48;
26. Gauthier L R, Charrin B C, Borrell-Pages M, Dompierre J P, Rangone H, Cordelieres F P, De Mey J, MacDonald M E, Lessmann V, Humbert S, Saudou F: Huntingtin controls neurotrophic support and survival of neurons by enhancing BDNF vesicular transport along microtubules. Cell 2004, 118:127-138;
27. Strand A D, Baguet Z C, Aragaki A K, Holmans P, Yang L, Cleren C, Beal M F, Jones L, Kooperberg C, Olson J M, Jones K R: Expression profiling of Huntington's disease models suggests that brain-derived neurotrophic factor depletion plays a major role in striatal degeneration. J Neurosci 2007, 27:11758-11768;
28. Wictorin K, Bjorklund A, Williams L R, Varon S, Gage F H: Amelioration of cholinergic neuron atrophy and spatial memory impairment in aged rats by nerve growth factor Nature 1987, 329:65-68
29. Sukoyan M A, Kerkis A Y, Mello M R, Kerkis I E, Visintin J A, Pereira L V. Establishment of new murine embryonic stem cell lines for the generation of mouse models of human genetic diseases. Braz J Med Biol Res. 2002 May; 35(5):535-42.
30. Carta L, Pereira L, Arteaga-Solis E, Lee-Arteaga S Y, Lenart B, Starcher B, Merkel C A, Sukoyan M, Kerkis A, Hazeki N, Keene D R, Sakai L Y, Ramirez F. Fibrillins 1 and 2 perform partially overlapping functions during aortic development. J Biol Chem. 2006 Mar. 24; 281(12): 8016-23

31. Kerkis A, Fonseca S A, Serafim R C, Lavagnolli T M, Abdelmassih S, Abdelmassih R, Kerkis I. In vitro differentiation of male mouse embryonic stem cells into both presumptive sperm cells and oocytes. Cloning Stem Cells. 2007 Winter; 9(4):535-48.

32. Lavagnolli T M, Fonseca S A, Serafim R C, Pereira V S, Santos E J, Abdelmassih S, Kerkis A, Kerkis I. Presumptive germ cells derived from mouse pluripotent somatic cell hybrids. Differentiation. 2009 September-October; 78(2-3):124-30

33. Hayashi M A, Guerreiro J R, Cassola A C, Lizier N F, Kerkis A, Camargo A C, Kerkis I. Long-term culture of mouse embryonic stem cell-derived adherent neurospheres and functional neurons. Tissue Eng Part C Methods. 2010 December; 16(6):1493-502.

34. Lima B L, Santos E J, Fernandes G R, Merkel C, Mello M R, Gomes J P, Soukoyan M, Kerkis A, Massironi S M, Visintin J A, Pereira L V A new mouse model for marfan syndrome presents phenotypic variability associated with the genetic background and overall levels of Fbnl expression. PLoS One. 2010 Nov. 30; 5(11):e14136.

35. Beltrão-Braga P C, Pignatari G C, Maiorka P C, Oliveira N A, Lizier N F, Wenceslau C V, Miglino M A, Muotri A R, Kerkis I. Feeder-free derivation of induced pluripotent stem cells from human immature dental pulp stem cells. Cell Transplant. 2011; 20(11-12):1707-19.

36. Bunting K D ABC transporters as phenotypic markers and functional regulators of stem cells. Stem Cells. 2002; 20(1):11-20.

37. Islam M O et al. Characterization of ABC transporter ABCB1 expressed in human neural stem/progenitor cells. FEBS letters. 2005 579(17): 3473-3480.

38. Mead B, Logan A, Berry M, Leadbeater W, Scheven B A. Intravitreally transplanted dental pulp stem cells promote neuroprotection and axon regeneration of retinal ganglion cells after optic nerve injury. Invest Ophthalmol Vis Sci. 2013; 54:7544-7556.

39. Mead B, Logan A, Berry M, Leadbeater W, Scheven B A. Paracrine-mediated neuroprotection and neuritogenesis of axotomised retinal ganglion cells by human dental pulp stem cells: comparison with human bone marrow and adipose-derived mesenchymal stem cells. PLoS One. 2014 Oct. 7; 9(10).

40. Martens W, Sanen K, Georgiou M, Struys T, Bronckaers A, et al. Human dental pulp stem cells can differentiate into Schwann cells and promote and guide neurite outgrowth in an aligned tissue-engineered collagen construct in vitro. (2013) The FASEB Journal.

41. Sakai K, Yamamoto A, Matsubara K, Nakamura S, Naruse M, Yamagata M, Sakamoto K, Tauchi R, Wakao N, Imagama S, Hibi H, Kadomatsu K, Ishiguro N, Ueda M. Human dental pulp-derived stem cells promote locomotor recovery after complete transection of the rat spinal cord by multiple neuro-regenerative mechanisms. J Clin Invest. 2012; 122: 80-90.

42. Rampon C, Weiss N, Deboux C, Chaverot N, Miller F, Buchet D, Tricoire-Leignel H, Cazaubon S, Baron-Van Evercooren A, Couraud P O. Molecular mechanism of systemic delivery of neural precursor cells to the brain: assembly of brain endothelial apical cups and control of transmigration by CD44. Stem Cells. 2008 July; 26(7): 1673-82.

43. Schu S, Nosov M, O'Flynn L, Shaw G, Treacy O, Barry F, Murphy M, O'Brien T, Ritter T. Immunogenicity of allogeneic mesenchymal stem cells. J Cell Mol Med. 2012; 16:2094-2103.

44. Weinger J G, Weist B M, Plaisted W C, Klaus S M, Walsh C M, Lane T E. MHC mismatch results in neural progenitor cell rejection following spinal cord transplantation in a model of viral-induced demyelination. Stem Cells. 2012 November; 30(11):2584-950

45. Bifari F, Pacelli L, Krampera M. Immunological properties of embryonic and adult stem cells. World J Stem Cells. 2010; 2:50-60.

46. Bertram L, McQueen M B, Mullin K, Blacker D, Tanzi R E. (2007) "Systematic meta-analyses of Alzheimer disease genetic association studies: the AlzGene database." Nat Genet 39(1): 17-23.

47. Jared B. Vasquez, a David W. Fardo, b and Steven Estusa,* ABCA7 expression is associated with Alzheimer's disease polymorphism and disease status. Neurosci Lett. Nov. 27, 2014

48. Yamagata et al. Human Dental Pulp-Derived Stem Cells Protect Against Hypoxic-Ischemic Brain Injury in Neonatal Mice. Stroke. 2013; 44:551-554.

49. Albensi, B. C., Sullivan, P. G., Thompson, M. B., Scheff, S. W. & Mattson, M. P. Cyclosporine ameliorates traumatic brain injury-induced alterations of hippocampal synaptic plasticity. Exp. Neurol. 162, 385-389 (2000).

50. Matsumoto, S., Friberg, H., Ferrand-Drake, M. & Wieloch, T. Blockade of the mitochondrial permeability transition pore diminishes infarct size in the rat after transient middle cerebral artery occlusion. J. Cereb. Blood Flow Metab. 19, 736-741 (1999).

51. Leventhal L, Jeffrey H. Kordower Cyclosporine A Protects Striatal Neurons from Mitochondrial Dysfunction. Immunosuppressant Analogs in Neuroprotection. 2003, pp 159-174.

52. Lee, R. H., Pulin, A. A., Seo, M. J., Kota, D. J., Ylostalo, J., Larson, B. L., Semprun-Prieto, L., Delafontaine, P., Prockop, D. J., 2009. Intravenous hMSCs improve myocardial infarction in mice because cells embolized in lung are activated to secrete the anti-inflammatory protein TSG-6. Cell Stem Cell 5 (1), 54-63.

53. GRIGORIADIS N, LOURBOPOULOS A, LAGOUDAKI R, FRISCHER J M, POLYZOIDOU E, TOULOUMI O, SIMEONIDOU C, DERETZI G, KOUNTOURAS J, SPANDOU E, KOTTA K, KARKAVELAS G, TASCOS N, LASSMANN H (2011) Variable behavior and complications of autologous bone marrow mesenchymal stem cells transplanted in experimental autoimmune encephalomyelitis. Experimental neurology 230: 78-89.

54. E. Y. Snyder. The risk of putting something where it does not belong: Mesenchymal stem cells produce masses in the brain Experimental Neurology 230 (2011) 75-77.

55. Dagur P K, McCoy J P Jr. Endothelial-binding, proinflammatory T cells identified by MCAM (CD146) expression: Characterization and role in human autoimmune diseases. Autoimmun Rev. 2015 May; 14(5):415-22.

What is claimed is:

1. A cryopreserved pharmaceutical composition comprising undifferentiated human immature dental pulp stem cells (hIDPSCs),
    wherein at least 80% of the hIDPSCs express DARPP32 and BDNF;
    at least 90% of the hIDPSCs express CD44 and CD13; and the hIDPSCs maintain the capacity to form multiple cell types including neuronal cells, fibroblast cells, and perivascular cells.

2. The pharmaceutical composition of claim 1, wherein expression of CD44 and CD13 enables the hIDPSCs to cross the blood brain barrier (BBB).

3. The pharmaceutical composition of claim 1, wherein the hIDPSCs express dopamine receptor D2.

4. The pharmaceutical composition of claim 1, wherein the hIDPSCs maintain colony forming capacity after multiple passages.

5. The pharmaceutical composition of claim 1 formulated for intravenous (IV) injection.

6. The pharmaceutical composition of claim 1, wherein the hIDPSCs are cryopreserved with dimethyl sulfoxide (DMSO).

7. A method of treating a neurological disease or condition comprising systemically administering to a subject the cryopreserved pharmaceutical composition of claim 1.

8. The method of claim 7, wherein the hIDPSCs are cryopreserved with DMSO.

9. The method of claim 7, wherein the pharmaceutical composition is intravenously administered to the subject.

10. The method of claim 7, wherein the hIDPSCs are autologous and/or allogeneic to the subject.

11. The method of claim 7, wherein the neurological disease or condition is selected from the group consisting of Parkinson's disease (PD), multiple sclerosis, amyotrophic lateral sclerosis (ALS), stroke, autoimmune encephalomyelitis, diabetic neuropathy, glaucomatous neuropathy, Alzheimer's disease, and Huntington's disease (HD).

12. The method of claim 11, wherein the neurological disease or condition is Huntington's disease (HD).

13. The method of claim 12, wherein the subject is diagnosed with early HD and administering the hIDPSCs to the subject supports a neuroprotective mechanism in the subject.

14. The method of claim 11, wherein the neurological disease or condition is Parkinson's disease (PD).

15. The method of claim 14, wherein the subject is diagnosed with PD and administering the hIDPSCs to the subject repairs lost dopaminergic neurons in the subject.

16. The method of claim 7, wherein the neurological disease or condition is selected from the group consisting of autism, schizophrenia, stroke, ischemia, a motor disorder, and a convulsive disorder.

17. The method of claim 7, wherein the hIDPSCs express dopamine receptor D2.

18. The method of claim 7, wherein the neurological disease or condition is treated by the hIDPSCs crossing the BBB.

* * * * *